United States Patent
Wu et al.

(10) Patent No.: US 10,937,968 B2
(45) Date of Patent: Mar. 2, 2021

(54) COMPOUND AND ORGANIC ELECTRONIC DEVICE USING THE SAME

(71) Applicant: Shanghai Nichem Fine Chemical Co., Ltd., Shanghai (CN)

(72) Inventors: Hui-Ling Wu, Hsinchu County (TW); Po-Chen Tseng, Hsinchu County (TW); Shwu-Ju Shieh, Hsinchu County (TW); Chi-Chung Chen, Hsinchu County (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 354 days.

(21) Appl. No.: 15/972,792

(22) Filed: May 7, 2018

(65) Prior Publication Data
US 2019/0341552 A1    Nov. 7, 2019

(51) Int. Cl.
*H01L 51/00*    (2006.01)
*H01L 51/50*    (2006.01)
(Continued)

(52) U.S. Cl.
CPC ........ *H01L 51/0061* (2013.01); *C07D 307/91* (2013.01); *H01L 51/001* (2013.01);
(Continued)

(58) Field of Classification Search
CPC .................. H01L 51/0061; H01L 51/0073
See application file for complete search history.

(56) References Cited

FOREIGN PATENT DOCUMENTS

| CN | 108623545 A | * 10/2018 | |
|---|---|---|---|
| JP | 2012089777 A | * 5/2012 | .............. H01L 51/50 |

(Continued)

OTHER PUBLICATIONS

Computer-generated English-language translation of JP-2012089777-A.*

(Continued)

*Primary Examiner* — Vu A Nguyen
(74) *Attorney, Agent, or Firm* — WPAT, PC

(57) ABSTRACT

Provided are a novel compound and an organic electronic device using the same. The novel compound is represented by Formula (I):

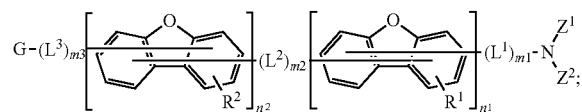

Formula (I)

wherein n1, n2, m1, m2 and m3 are each an integer, the sum of n1 and n2 is 2 or 3; $L^1$, $L^2$ and $L^3$ are each an arylene group; $R^1$ and $R^2$ are each selected from the group consisting of: H, D, an alkyl group, and an aryl group; G is selected from the group consisting of: H, D, —$N(Z^3)(Z^4)$ group, an alkyl group, an alkenyl group, an alkynyl group, a cycloalkyl group, a heterocycloalkyl group, an aryl group, and a heteroaryl group; and $Z^1$ to $Z^4$ are each selected from the group consisting of: an alkyl group, an alkenyl group, an alkynyl group, a cycloalkyl group, a heterocycloalkyl group, an aryl group, and a heteroaryl group.

16 Claims, 10 Drawing Sheets

(51) Int. Cl.
*C07D 307/91* (2006.01)
*H01L 51/56* (2006.01)
(52) U.S. Cl.
CPC ...... *H01L 51/0073* (2013.01); *H01L 51/5064* (2013.01); *H01L 51/5088* (2013.01); *H01L 51/56* (2013.01); *H01L 2251/558* (2013.01)

(56) References Cited

FOREIGN PATENT DOCUMENTS

KR   10-2017-0082459       7/2017
WO   WO-2017196081 A1 *  11/2017  ............. C09K 11/06

OTHER PUBLICATIONS

Computer-generated English-language translation of CN-108623545-A.*
STN Search (Jun. 16, 2020).*
SciFinder Search (Jun. 9, 2020).*

* cited by examiner

COMPOUND AND ORGANIC ELECTRONIC DEVICE USING THE SAME

BACKGROUND OF THE INVENTION

1. Field of the Invention

The present invention relates to a novel compound and an organic electronic device using the same, more particularly to a novel compound as a material for a hole transport layer or a hole injection layer and an organic electronic device using the same.

2. Description of the Prior Arts

With the advance of technology, various organic electronic devices that make use of organic materials have been energetically developed. Examples of the organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching W. Tang and Steven VanSlyke of Kodak Company deposited an electron transport material such as tris(8-hydroxyquinoline)aluminum(III) (abbreviated as Alq$_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to adopt an amine derivative with a carbazolyl group as a hole transport material of the HTL. However, even using the foresaid hole transport materials of HTL, the current efficiency and luminous efficacy of OLEDs still needs to be improved.

Another approach is to adopt a diamine derivative as a hole injection material of the HIL. However, even using the foresaid hole injection materials of HIL, the current efficiency and luminous efficacy of OLEDs still needs to be improved.

Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

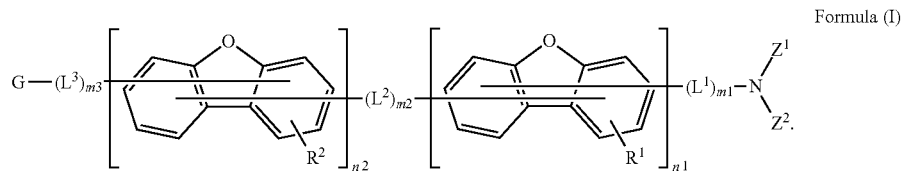

Formula (I)

In Formula (I), n1 and n2 are each independently an integer from 0 to 3, and the sum of n1 and n2 is 2 or 3.

In Formula (I), m1, m2 and m3 are each independently an integer 0 or 1. That is, m1, m2 and m3 can be the same or different.

In Formula (I), $R^1$ and $R^2$ are each independently selected from the group consisting of: a hydrogen atom, a deuterium atom, an alkyl group having 1 to 12 carbon atoms, and an aryl group having 6 to 30 ring carbon atoms, and $R^1$ and $R^2$ are the same or different.

In Formula (I), $L^1$, $L^2$ and $L^3$ are each independently an arylene group having 6 to 60 ring carbon atoms, and L, $L^2$ and $L^3$ are the same or different.

In Formula (I), G is selected from the group consisting of: a hydrogen atom, a deuterium atom, —N($Z^3$)($Z^4$) group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms.

In Formula (I), $Z^1$ to $Z^4$ are each independently selected from the group consisting of: an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms. $Z^1$ to $Z^4$ may be the same or different.

In accordance with the present invention, the compound may be represented by the following Formula (I'):

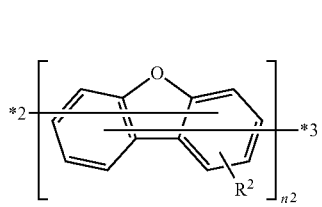

Formula (I')

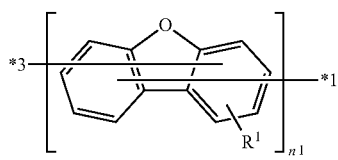

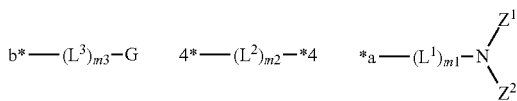

wherein *1 is bonded to *a, *2 is bonded to *b, and two *3s are bonded to two *4s, respectively.

In the case that both bonding groups of dibenzofuranyl are bonded on the same benzene ring, for example, the group of

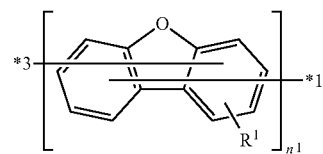

in Formula (I') may be represented by

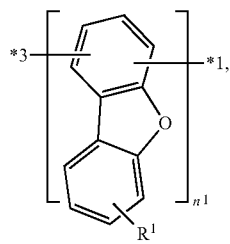

or the group of

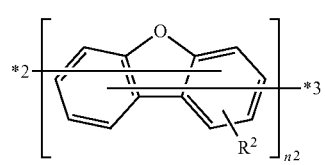

in Formula (I') may be represented by

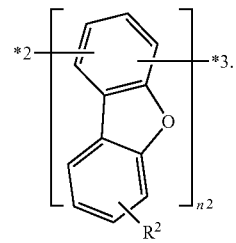

More specifically, the group of

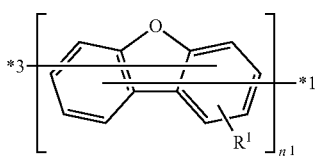

in Formula (I') may be represented by any one of the following formulae:

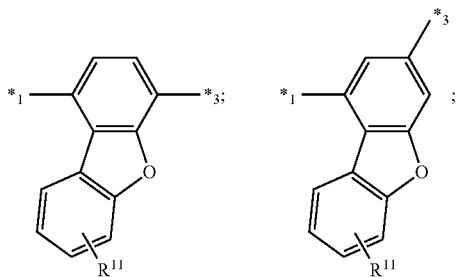

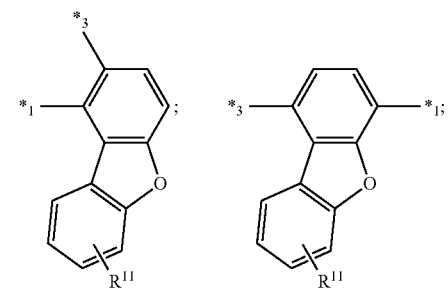

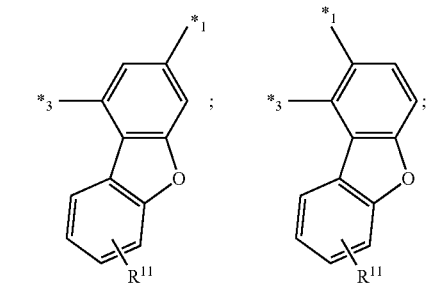

-continued
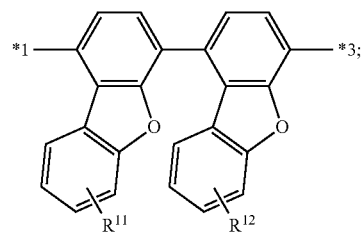
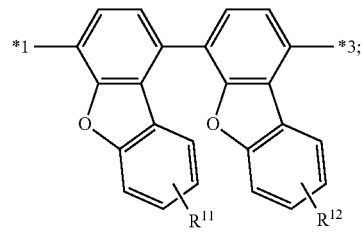
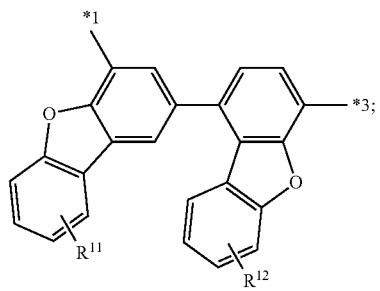
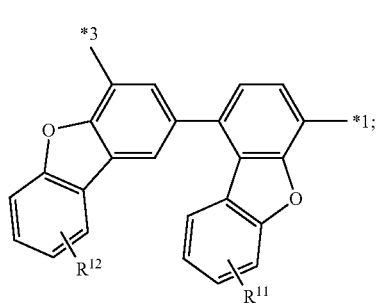
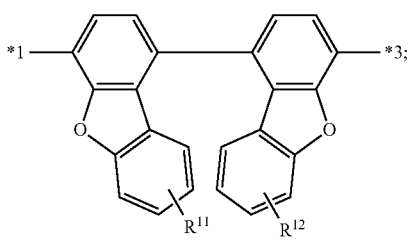
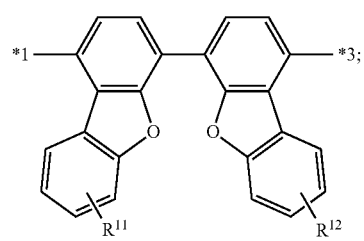
-continued
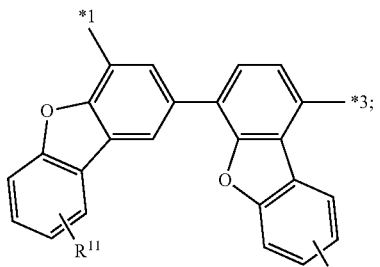
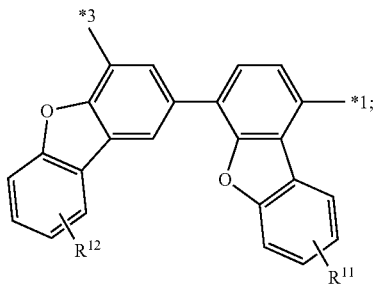
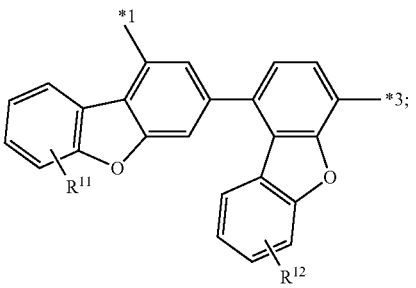
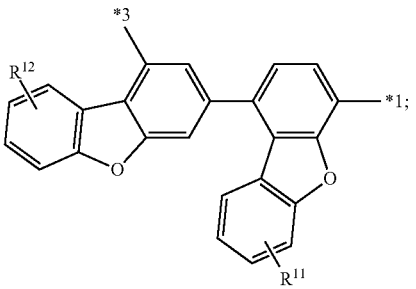
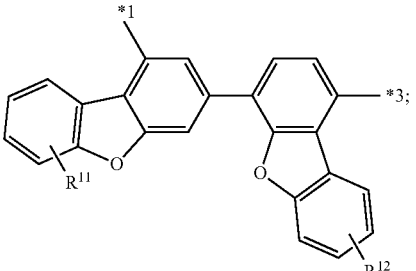
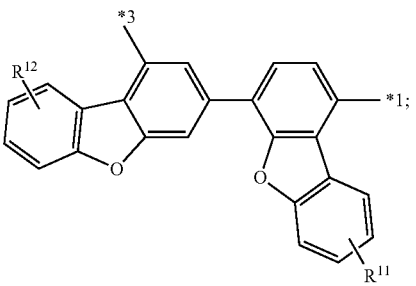

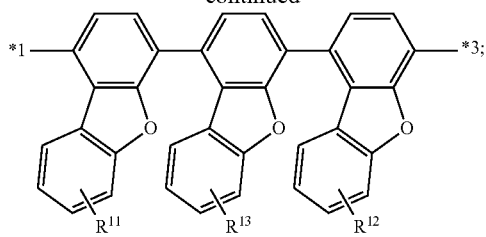

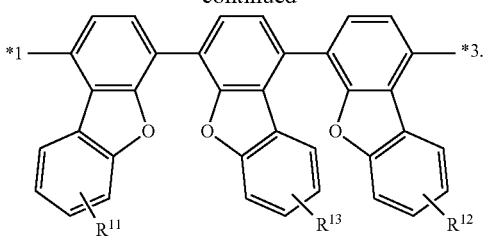

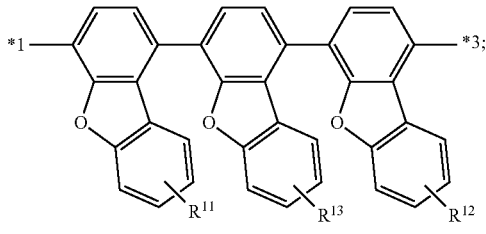

$R^1$ group in Formula (I) may be represented by $R^{11}$ to $R^{13}$. Herein, $R^{11}$ to $R^{13}$ are each independently selected from the group consisting of: a hydrogen atom, a deuterium atom, an alkyl group having 1 to 12 carbon atoms, and an aryl group having 6 to 30 ring carbon atoms, and $R^{11}$ to $R^{13}$ are the same or different.

More specifically, the group of

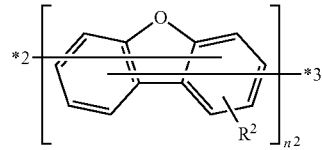

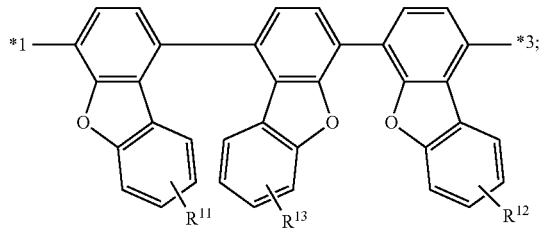

in Formula (I') may be represented by any one of the following formulae:

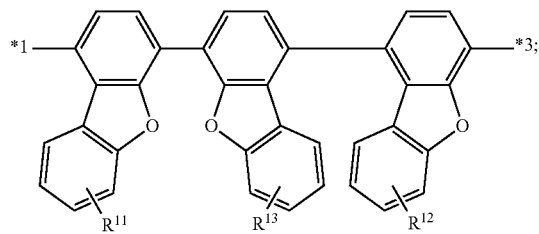

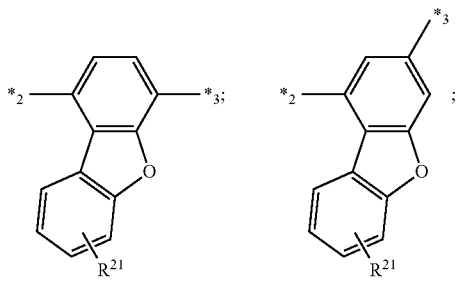

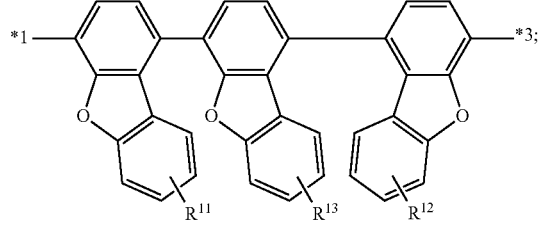

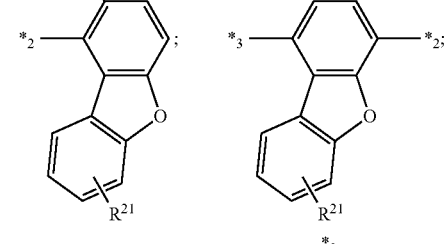

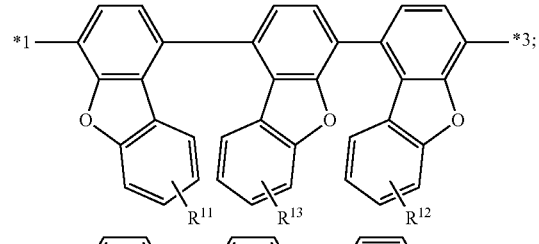

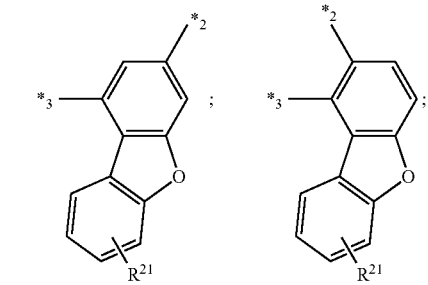

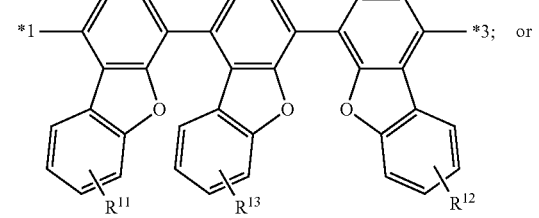

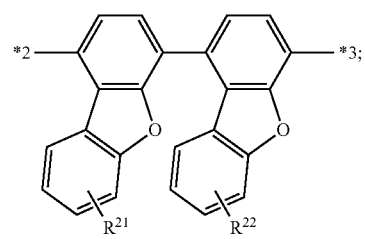
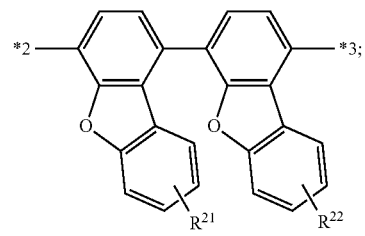
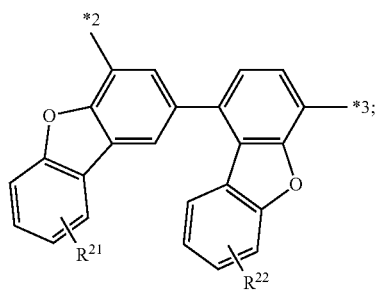
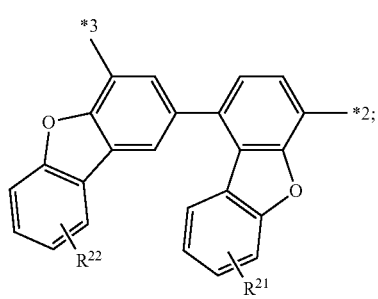
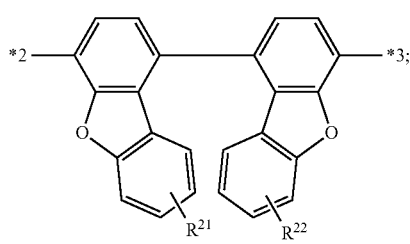
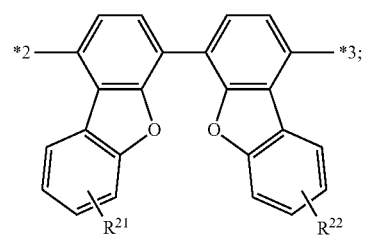
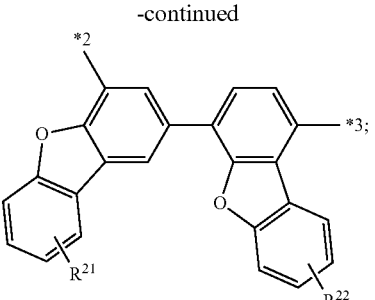
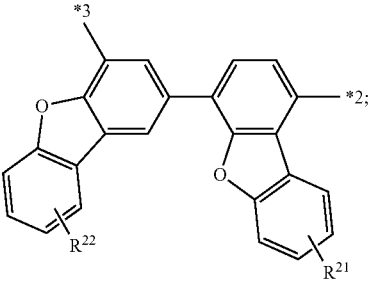
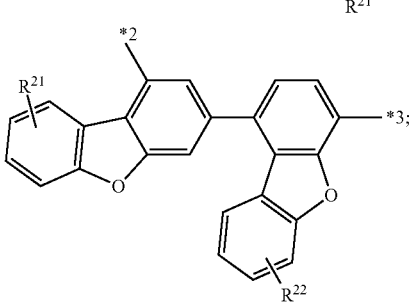
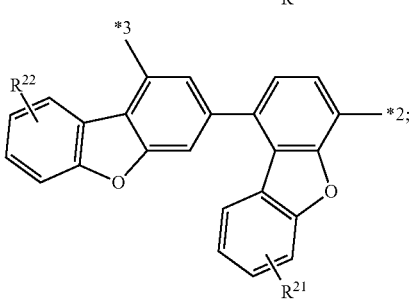
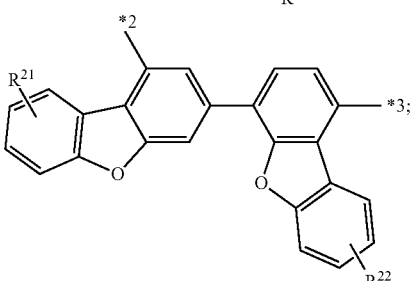
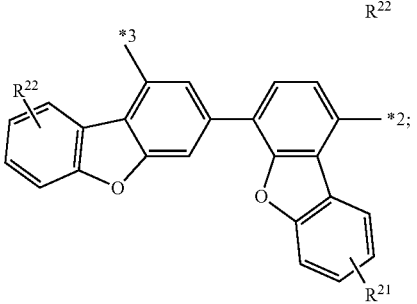

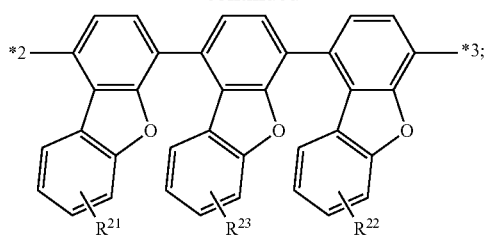

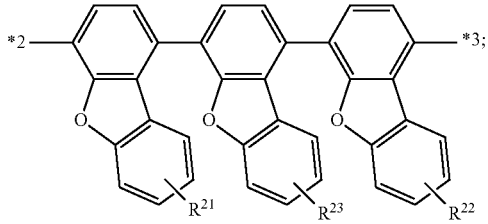

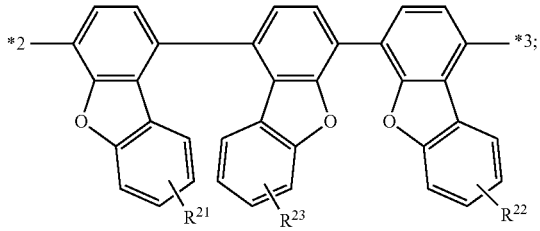

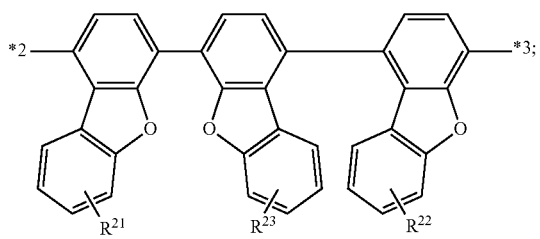

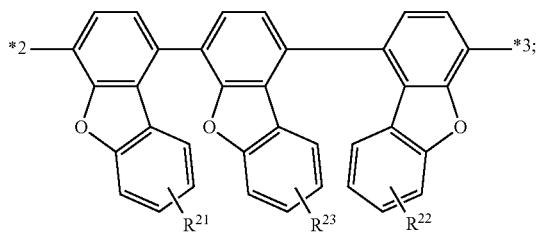

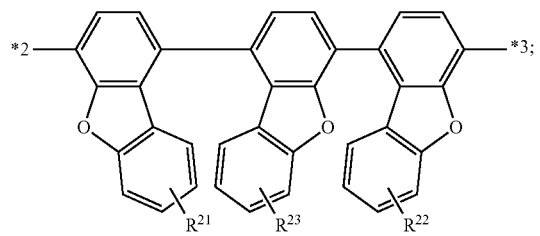

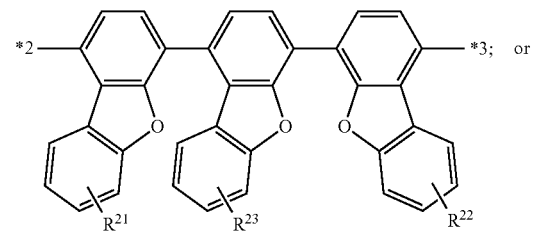 or

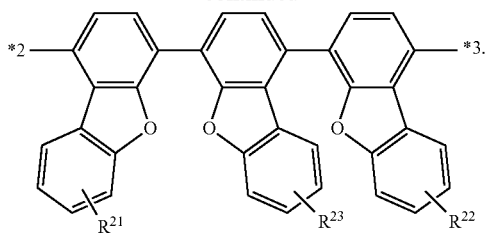

$R^2$ group in Formula (I) may be represented by $R^{21}$ to $R^{23}$. Herein, $R^{21}$ to $R^{23}$ are each independently selected from the group consisting of: a hydrogen atom, a deuterium atom, an alkyl group having 1 to 12 carbon atoms, and an aryl group having 6 to 30 ring carbon atoms, and $R^{21}$ to $R^{23}$ are the same or different.

More specifically, the groups of

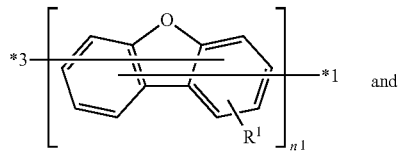 and

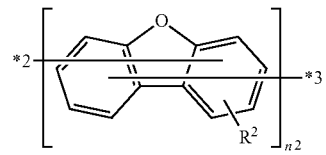

in Formula (F) may be the same or different.

When n1 is 1, i.e., the group of

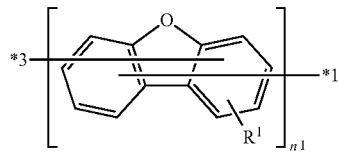

in Formula (I') is

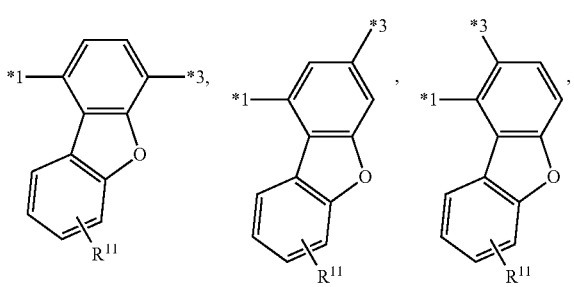

-continued

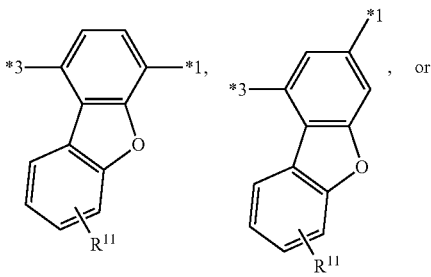

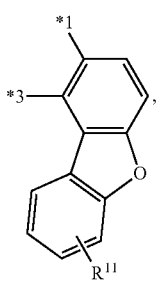

n2 is the integer 1 or 2.

Likely, when n2 is 1, i.e., the group of

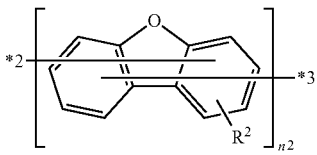

in Formula (I') is

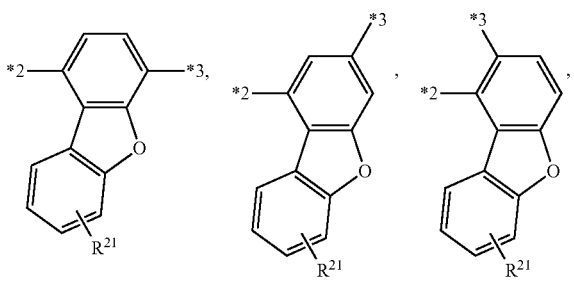

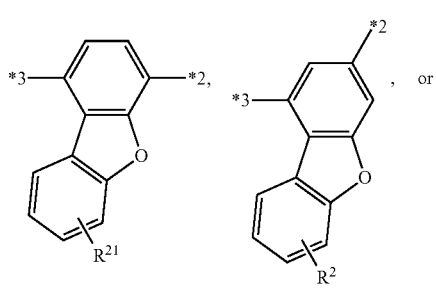

-continued

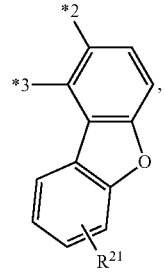

n1 is the integer 1 or 2.

Preferably, the compound is represented by the following Formula (I"):

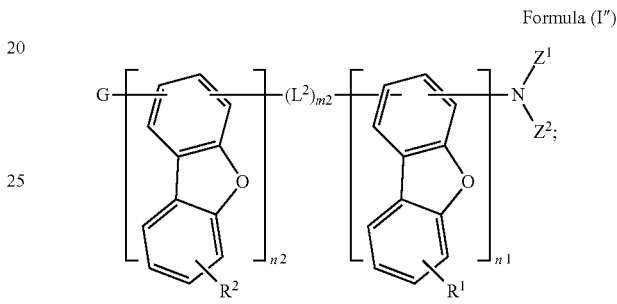

Formula (I")

wherein $R^1$ and $R^2$ are each independently selected from the group consisting of: a hydrogen atom, a deuterium atom, an alkyl group having 1 to 12 carbon atoms, and an aryl group having 6 to 30 ring carbon atoms, and $R^1$ and $R^2$ are the same or different; and G is selected from the group consisting of: the hydrogen atom, the deuterium atom, the alkyl group having 1 to 40 carbon atoms, the alkenyl group having 2 to 40 carbon atoms, the alkynyl group having 2 to 40 carbon atoms, and the aryl group having 6 to 60 ring carbon atoms.

Preferably, $R^1$ and $R^2$ in Formula (I") are each independently selected from the group consisting of: a hydrogen atom, a deuterium atom, an alkyl group having 1 to 6 carbon atoms, and an aryl group having 6 to 12 ring carbon atoms.

Preferably, in Formula (I"), n1 and n2 are each independently the integer 1 or 2.

Preferably, in Formula (I"), m2 is the integer 0 or 1, and $L^2$ is the arylene group as stated below, such as phenylene group. When m2 is the integer 0, $(L^2)_{m2}$ is a single bond.

Preferably, the heteroaryl group having 3 to 60 ring carbon atoms represented by G in Formulae (I) and (I') is selected from the group consisting of: a furyl group, a pyrrolyl group, a thiophenyl group; an imidazolyl group, a pyrazolyl group, a triazolyl group, a tetrazolyl group, an oxazolyl group, an isoxazolyl group, a thiazolyl group, an isothiazolyl group, an oxadiazolyl group, a thiadiazolyl group; a pyridyl group, a pyridazinyl group, a pyrimidinyl group, a pyrazinyl group, a triazinyl group; an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group; an indazolyl group, a benzisoxazolyl group, a benzisothiazolyl group; a dibenzofuranyl group, a dibenzothiophenyl group, a carbazolyl group, a biscarbazolyl group, a coumarinyl group, a chromenyl group, a phenanthridinyl group, an acridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, a dinaphthothienothiophenyl group, a dinaphtho[2',3':2,3:2',3':6,7]carbazolyl group, a dibenzo[b,f]azepin group, a tribenzo[b,d,f]azepin group, a dibenzo[b,f]oxepin group, and a tribenzo[b,d,f]oxepin group.

More specifically, the heteroaryl group having 3 to 60 ring carbon atoms represented by G in Formulae (I) and (I') is represented by any one of the following formulae:

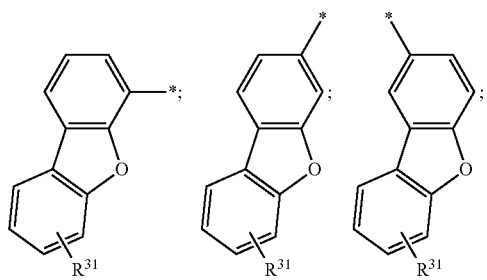

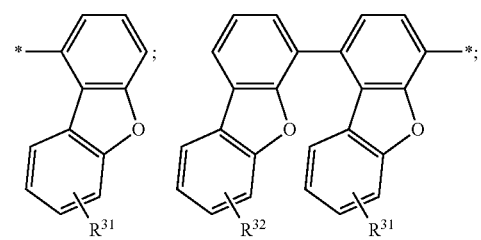

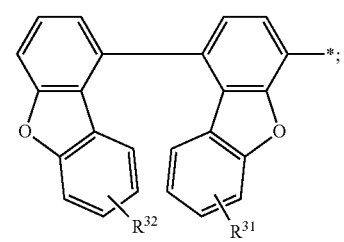

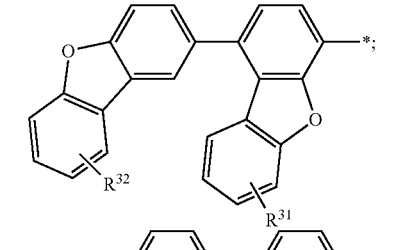

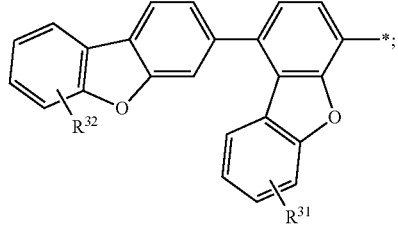

-continued

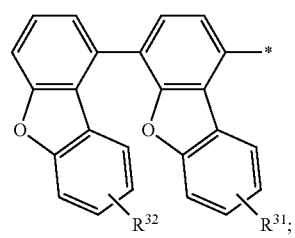

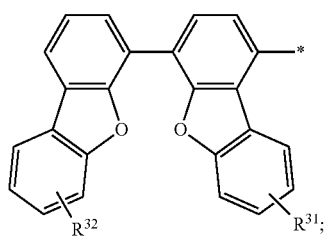

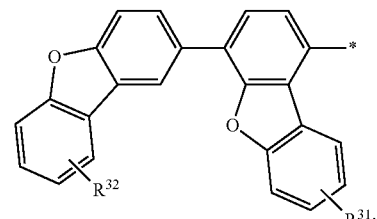

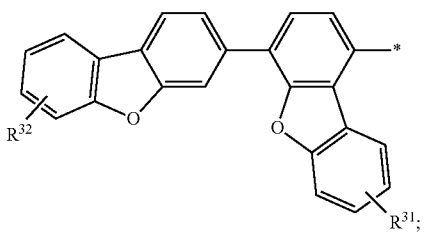

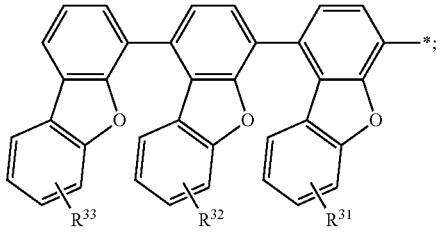

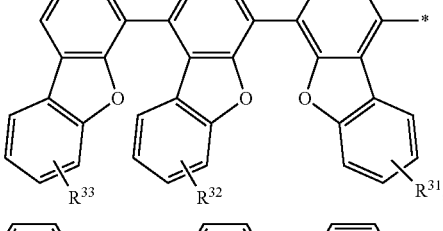

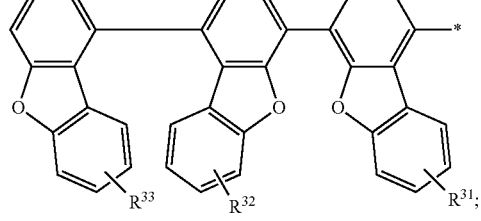

-continued

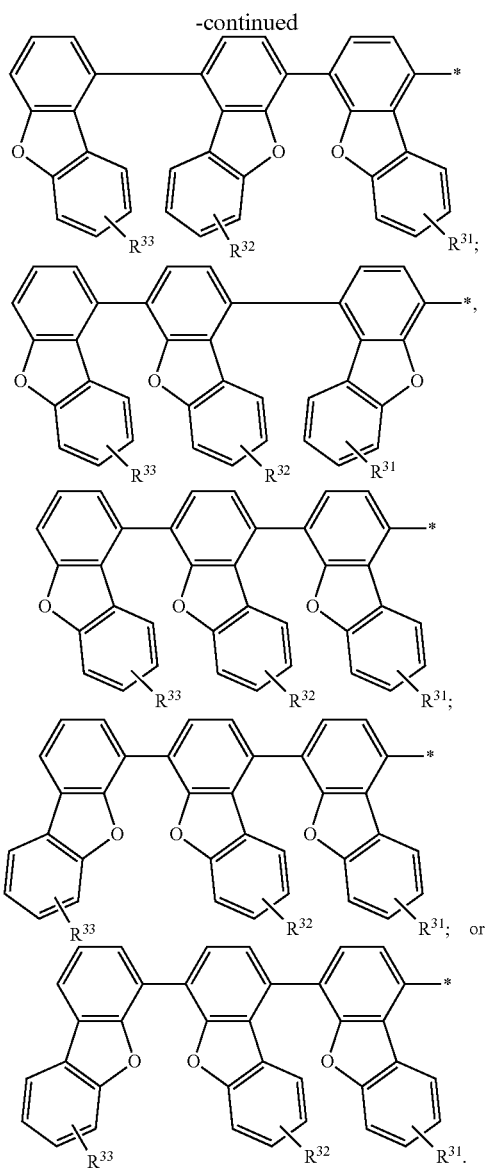

Herein, $R^{31}$ to $R^{33}$ are each independently selected from the group consisting of: a hydrogen atom, a deuterium atom, an alkyl group having 1 to 12 carbon atoms, and an aryl group having 6 to 30 ring carbon atoms, and $R^{31}$ to $R^{33}$ are the same or different.

Preferably, $Z^1$ to $Z^4$ in Formulae (I) to (I'') are each independently the aryl group having 6 to 60 ring carbon atoms.

Preferably, the aryl groups having 6 to 60 ring carbon atoms represented by G and $Z^1$ to $Z^4$ in Formulae (I) to (I'') are each independently selected from the group consisting of: a phenyl group, a biphenylyl group, a terphenylyl group, a quaterphenylyl group, a quinquephenylyl group, a naphthyl group, an acenaphthelenyl group, an anthryl group, a benzanthryl group, an aceanthryl group, a phenanthryl group, a benzophenanthryl group, a phenalenyl group, a fluorenyl group, a benzofluorenyl group, a dibenzofluorenyl group, a picenyl group, a pentacenyl group, a pyrenyl group, a benzopyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, an indacenyl group, a triphenylenyl group, a benzotriphenylenyl group, and any isomeric group thereof.

More specifically, the aryl groups having 6 to 60 ring carbon atoms represented by G and $Z^1$ to $Z^4$ in Formulae (I) to (I'') are each independently selected from the group consisting of:

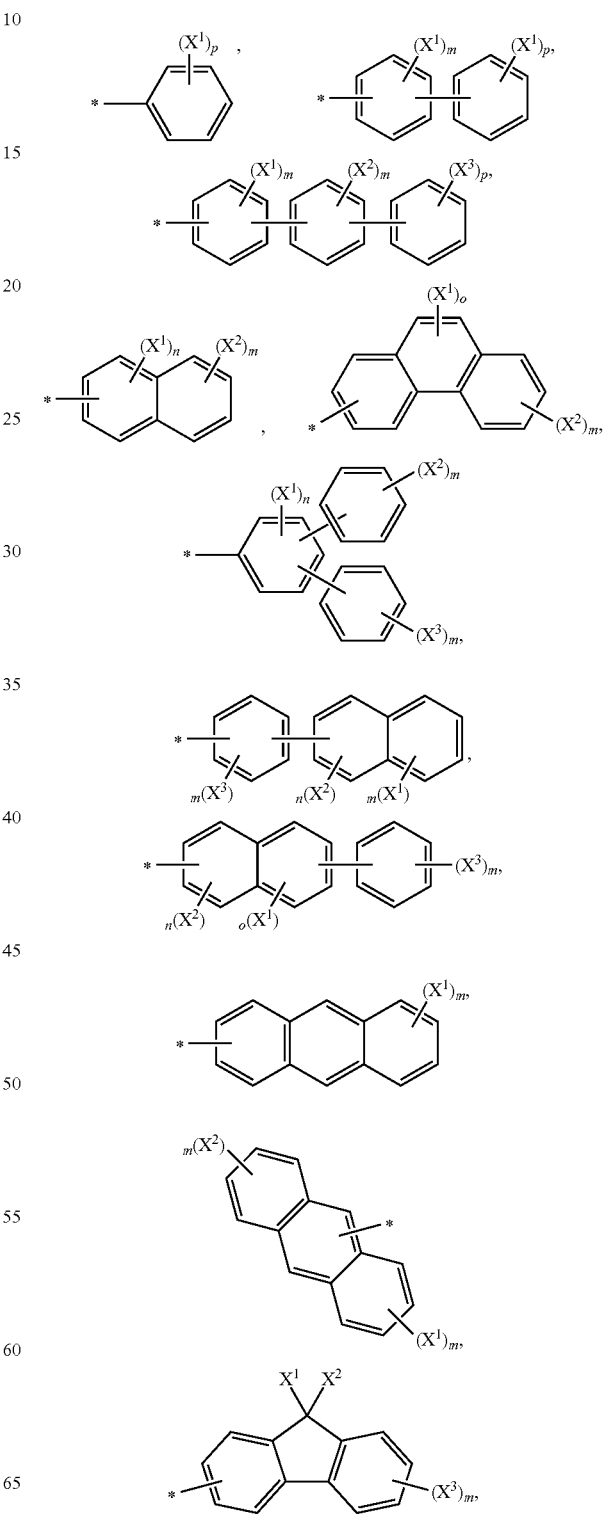

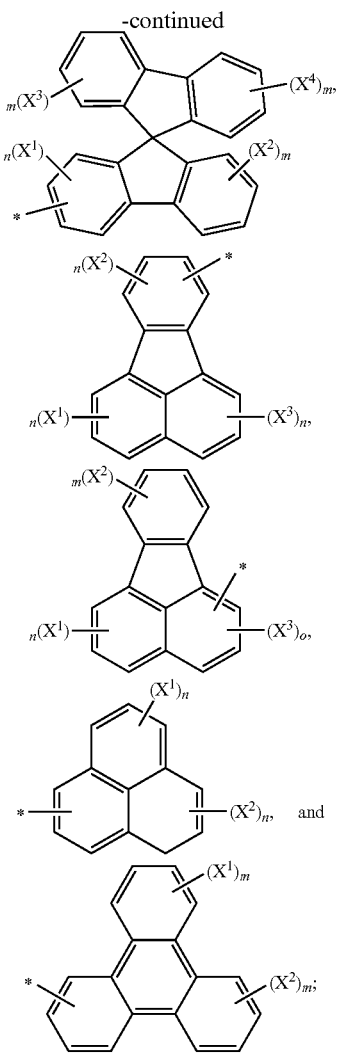

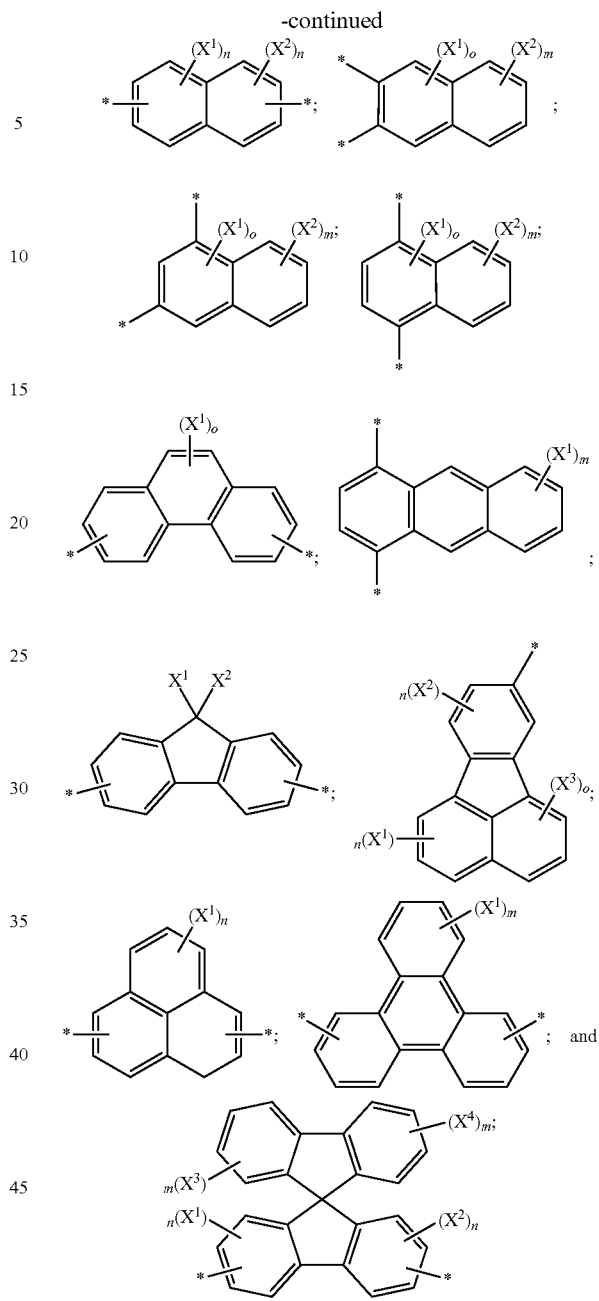

wherein m is an integer from 1 to 4, n is an integer from 1 to 3, o is an integer 1 or 2, and p is an integer from 1 to 5; and $X^1$ to $X^4$ are each independently selected from the group consisting of: a hydrogen atom, a deuterium atom, a halo group, such as a fluoro group, a chloro group, and a bromo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

Preferably, the arylene groups having 6 to 60 ring carbon atoms represented by $L^1$, $L^2$ and $L^3$ in Formulae (I) to (I'') are each independently selected from the group consisting of:

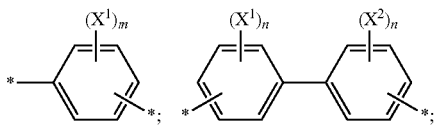

wherein m is an integer from 1 to 4, n is an integer from 1 to 3, and o is an integer 1 or 2; and $X^1$ to $X^4$ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

More specifically, the —N($Z^1$)($Z^2$) group in Formula (I) to (I'') and the —N($Z^3$)($Z^4$) group represented by G in Formula (I) and (I') are each independently selected from the group consisting of:

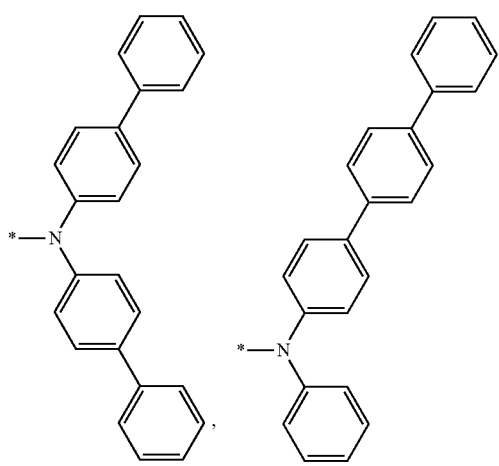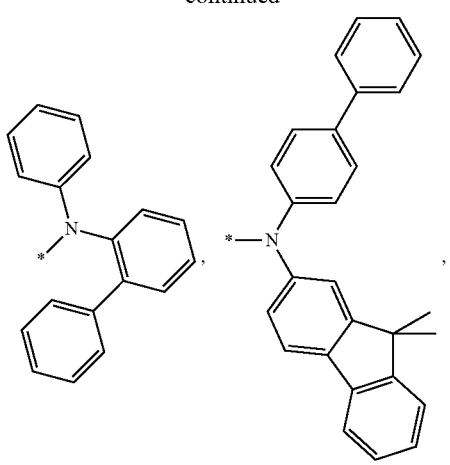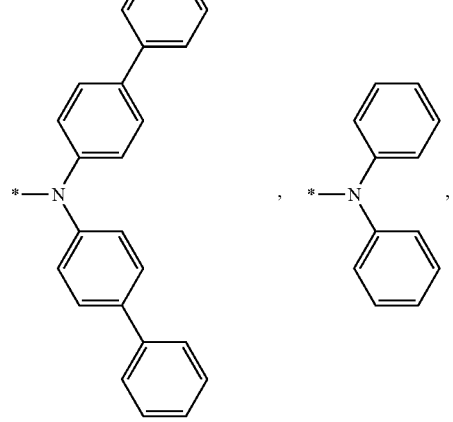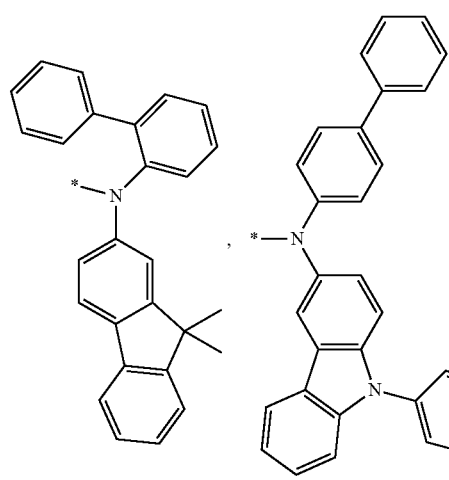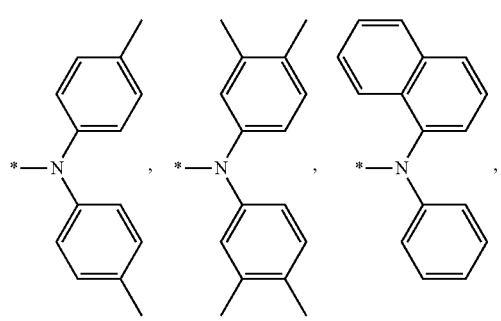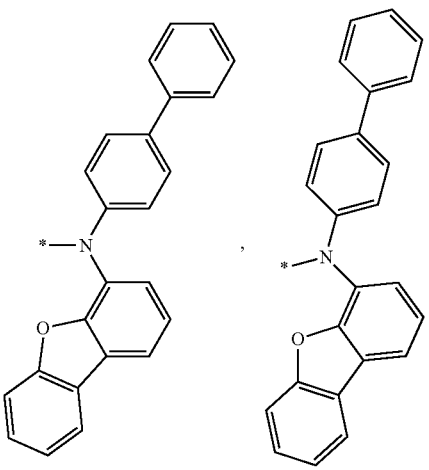

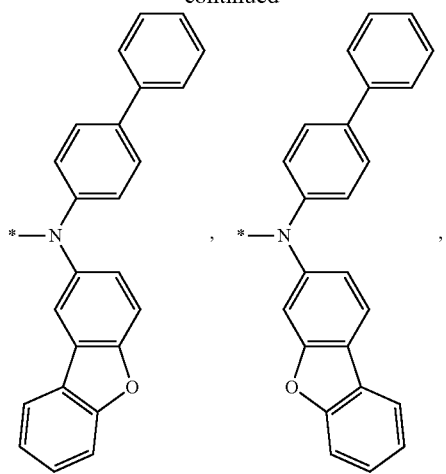, 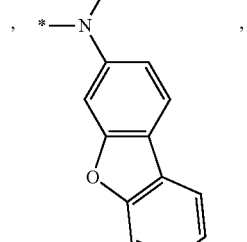,
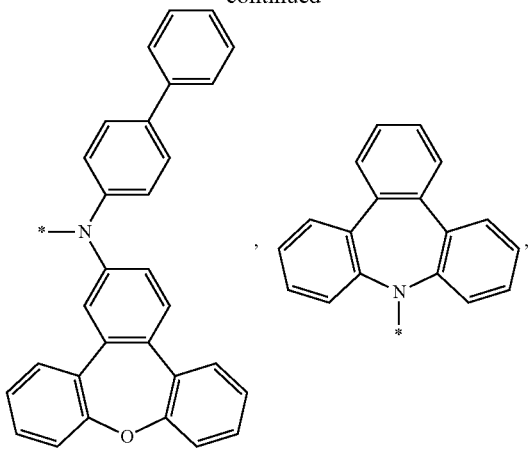,
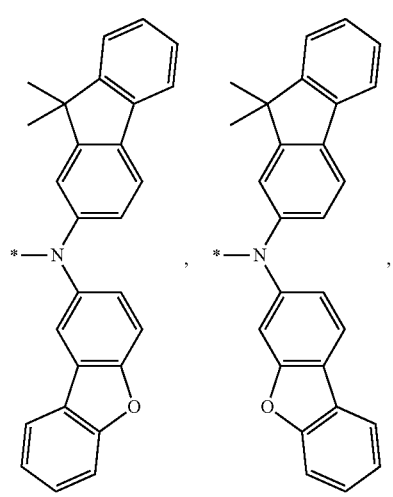, 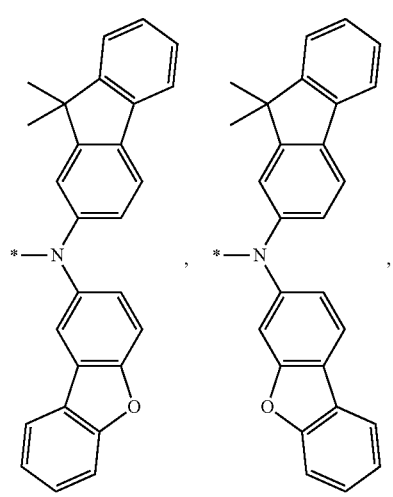,
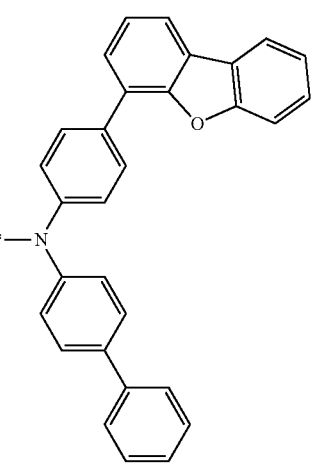,
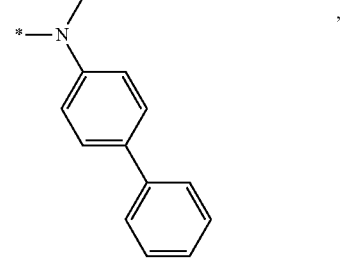,
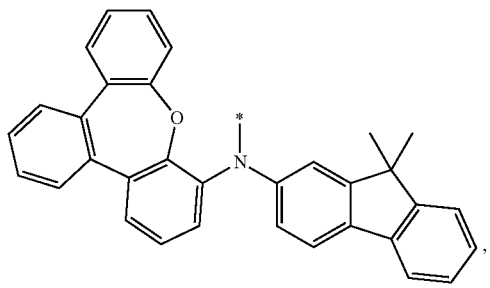,
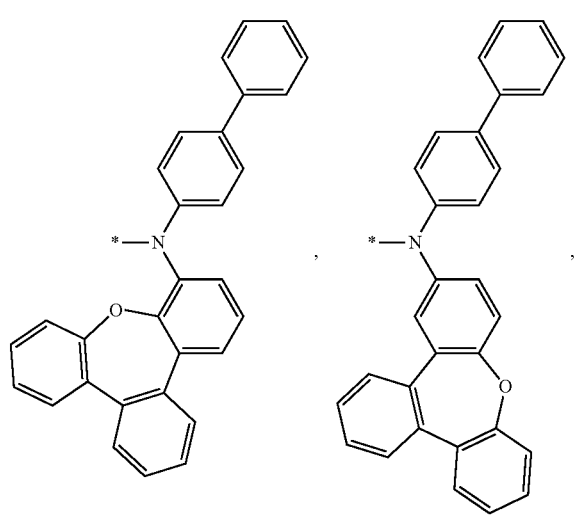, 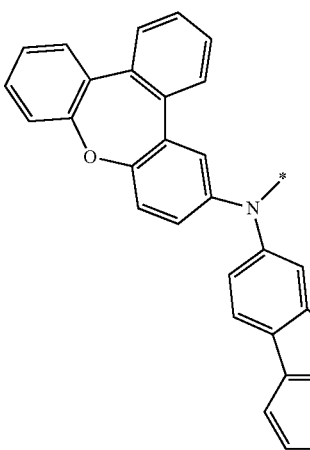,
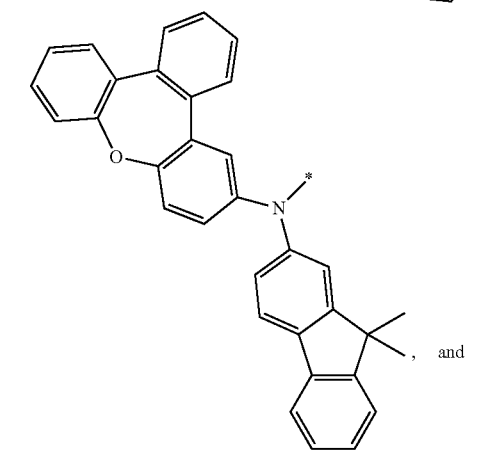,
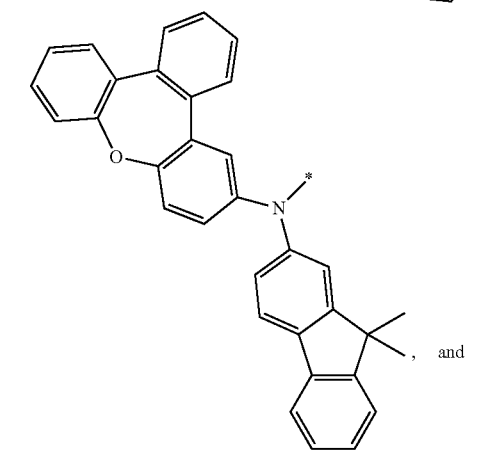, and

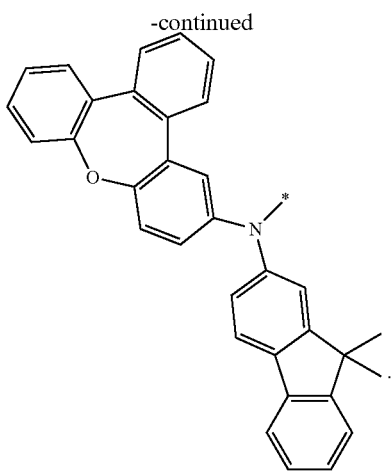

Preferably, $Z^1$ and $Z^2$ in Formulae (I) to (I″) are joined together to form a heteroaryl ring. For example, the heteroaryl ring may be

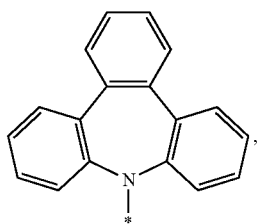

but it is not limited thereto.

Preferably, the —N($Z^3$)($Z^4$) group is represented by G in Formulae (I) and (I′), and $Z^3$ and $Z^4$ are joined together to form a heteroaryl ring. For example, the heteroaryl ring may be

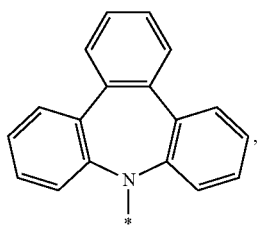 [SMILES: *N1c2ccccc2-c2ccccc2-c2ccccc21]

but it is not limited thereto.

In this specification, said "arylene group having 6 to 60 ring carbon atoms" denoted by $L^1$, $L^2$, or $L^3$, may be an unsubstituted arylene group having 6 to 60 ring carbon atoms or an arylene group having 6 to 60 ring carbon atoms substituted with at least one substituent. The substituent on the arylene group may be any one of $X^1$ to $X^4$ as stated above.

In this specification, said "aryl group" may be an unsubstituted aryl group or an aryl group substituted with at least one substituent, and said "heteroaryl group" may be an unsubstituted heteroaryl group or a heteroaryl group substituted with at least one substituent. The substituent on the aryl group may be any one of $X^1$ to $X^4$ as stated above. The substituent on the heteroaryl group may be similar to any one of $X^1$ to $X^4$ as stated above.

In this specification, said "alkyl group" may be an unsubstituted alkyl group or an alkyl group substituted with at least one substituent, said "alkenyl group" may be an unsubstituted alkenyl group or an alkenyl group substituted with at least one substituent, and said "alkynyl group" may be an unsubstituted alkynyl group or an alkynyl group substituted with at least one substituent. The substituent on the alkyl group, alkenyl group, or alkynyl group may be, for example, but not limited to a deuterium atom.

In this specification, said "cycloalkyl group" may be an unsubstituted cycloalkyl group or a cycloalkyl group substituted with at least one substituent, and said "heterocycloalkyl group" may be an unsubstituted heterocycloalkyl group or a heterocycloalkyl group substituted with at least one substituent. The substituent on the cycloalkyl group or heterocycloalkyl group may be, for example, but not limited to a deuterium atom, an alkyl group having 1 to 12 carbon atoms, an alkenyl group having 2 to 12 carbon atoms, or an alkynyl group having 2 to 12 carbon atoms.

For example, the compound may be selected from the group consisting of:

Compound 1

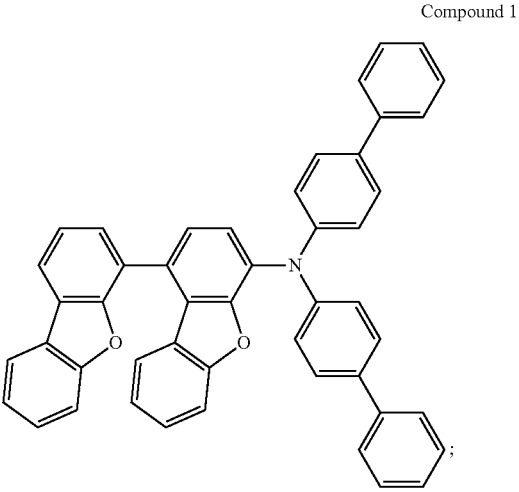

Compound 2

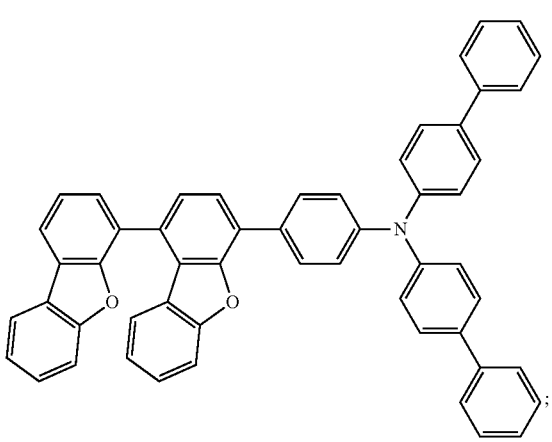

Compound 3
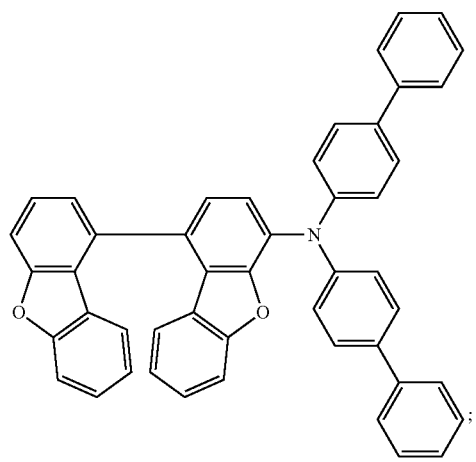
Compound 4
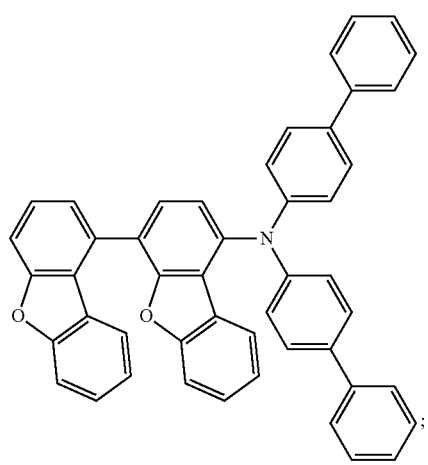
Compound 5
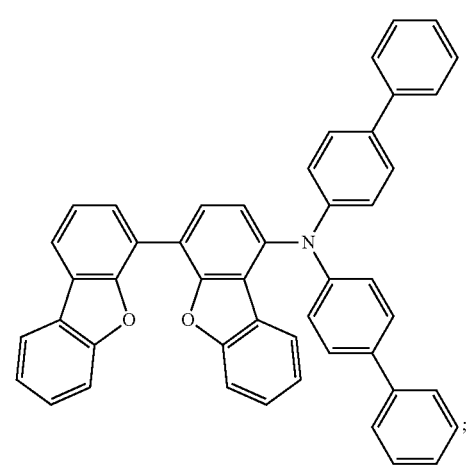
Compound 6
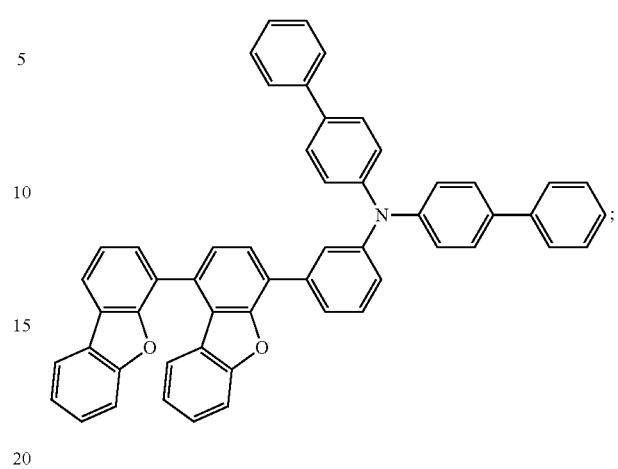
Compound 7
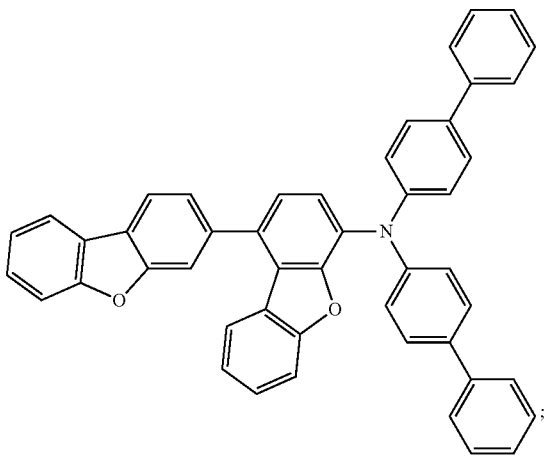
Compound 8
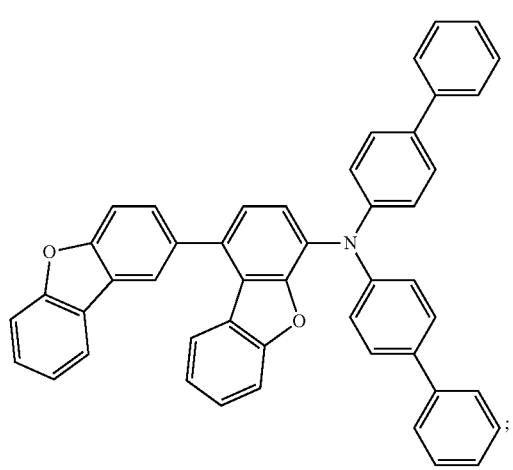

Compound 9
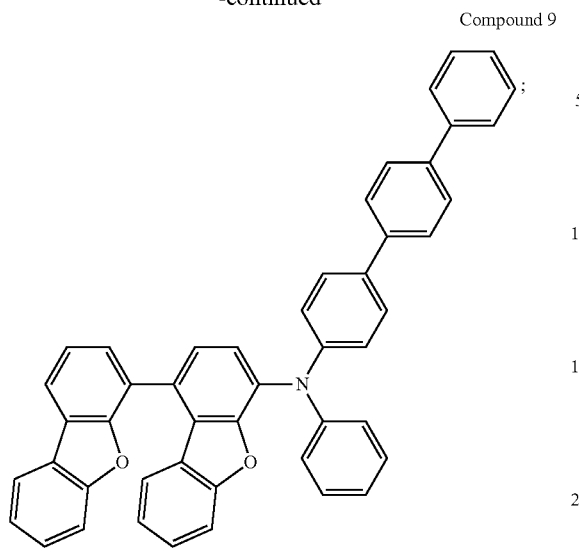
Compound 10
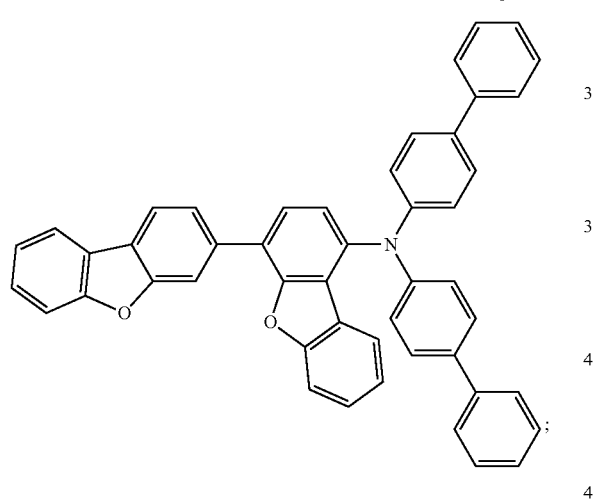
Compound 11
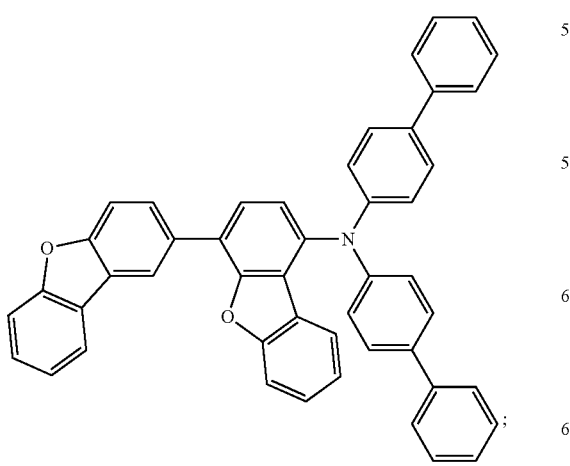
Compound 12
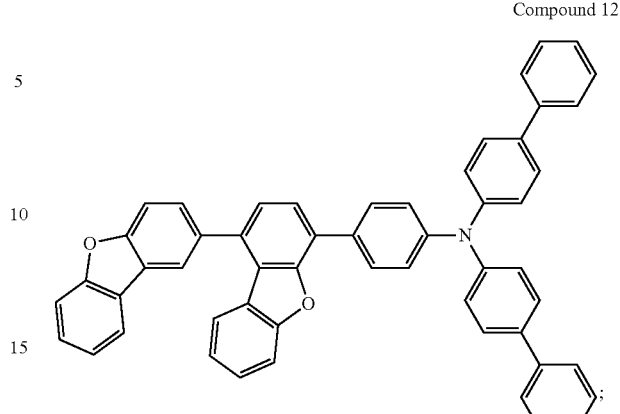
Compound 13
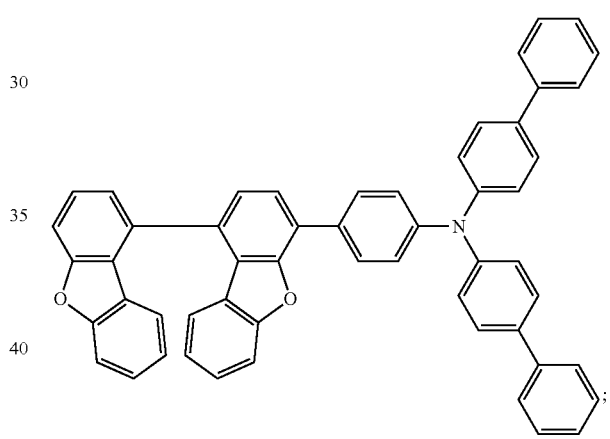
Compound 14
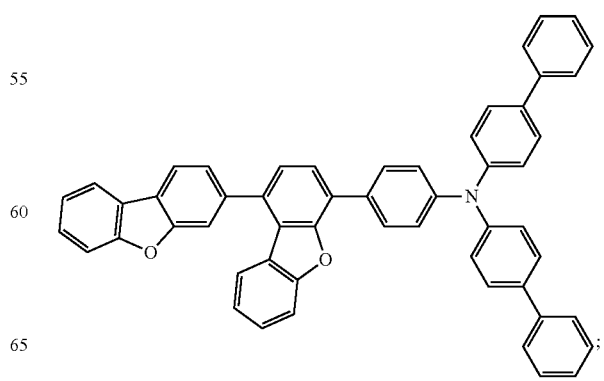

Compound 15
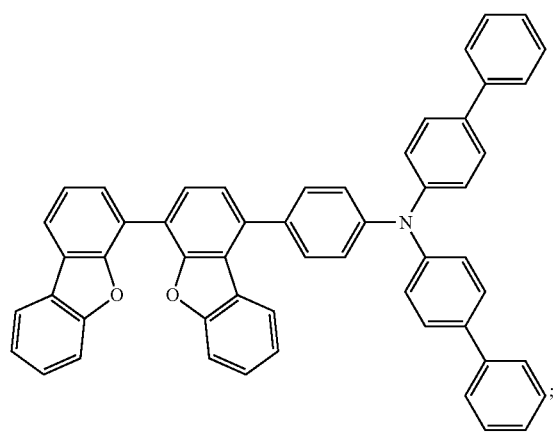
Compound 16
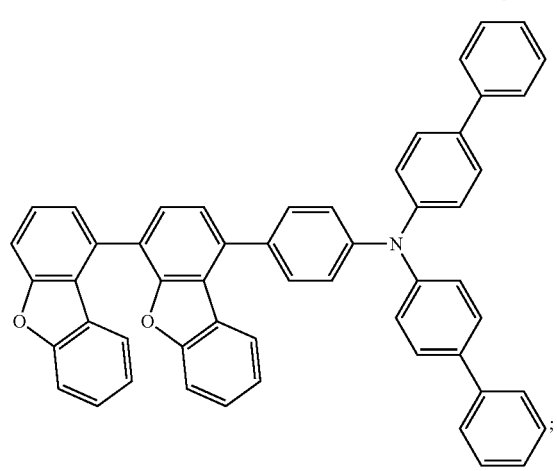
Compound 17
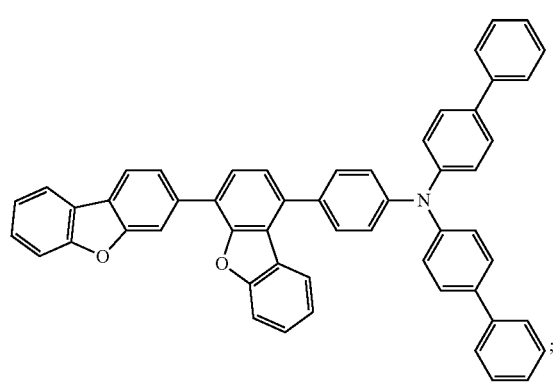
Compound 18
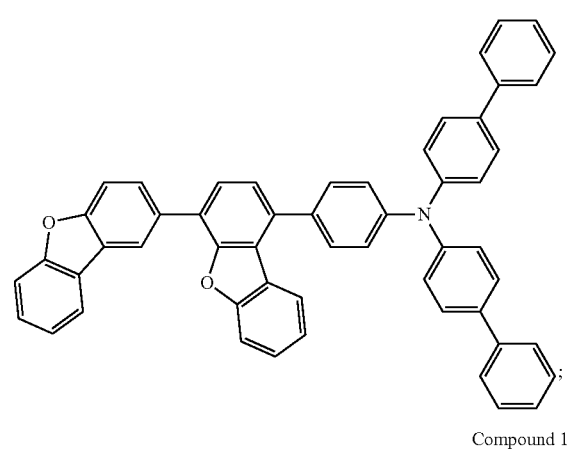
Compound 19, Compound 20, Compound 21
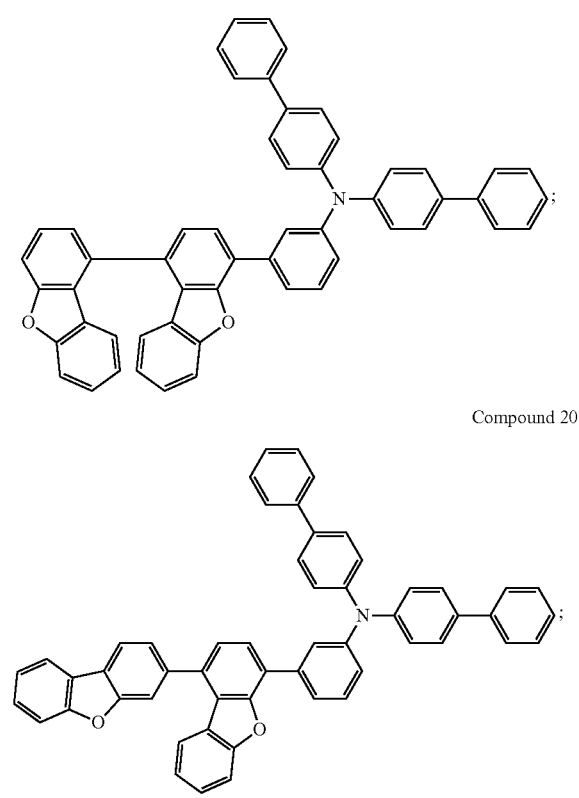
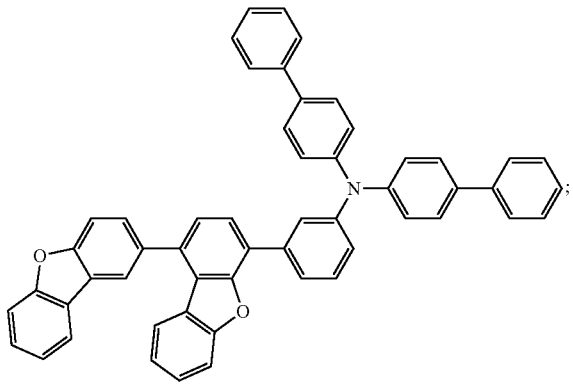

Compound 22
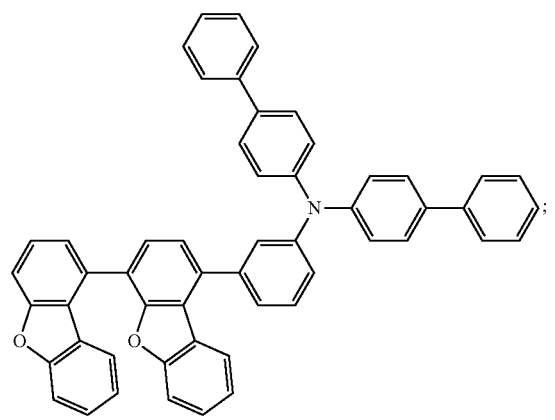
Compound 23
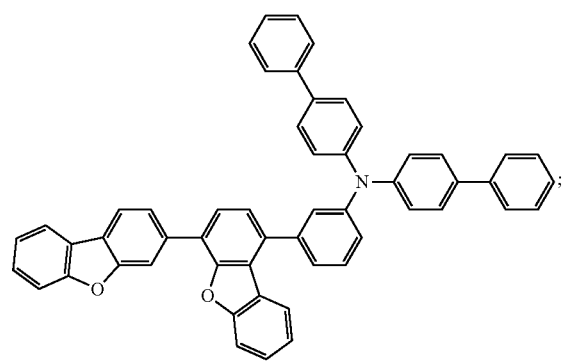
Compound 24
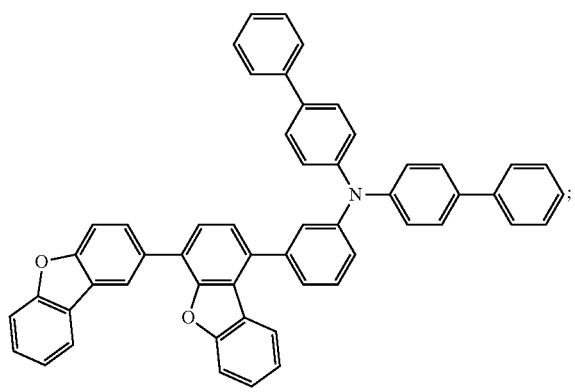
Compound 25
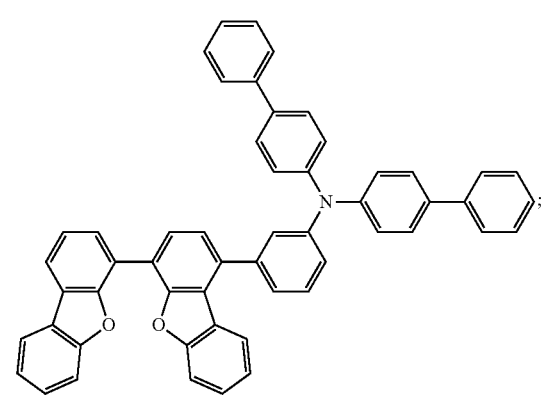
Compound 26
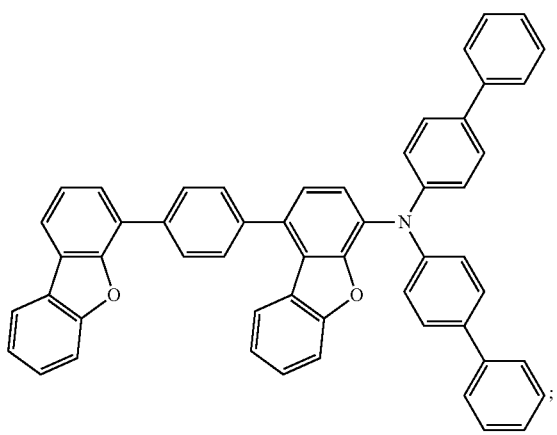
Compound 27
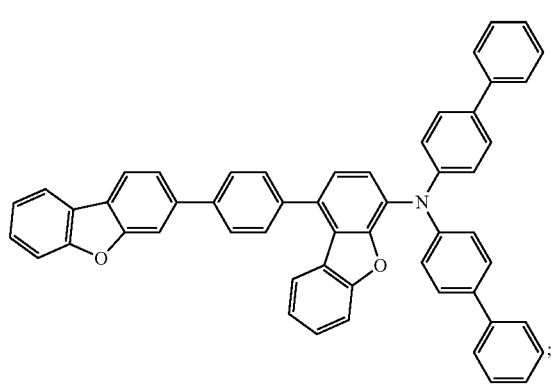
Compound 28
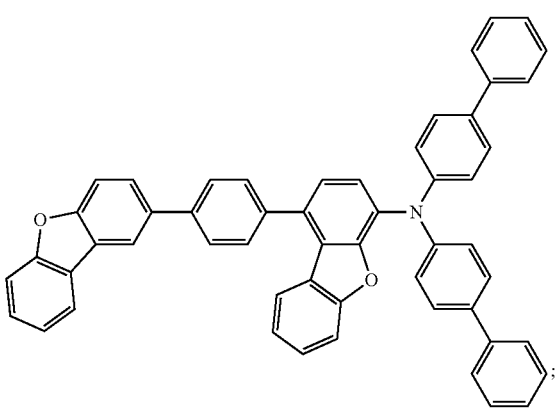

Compound 29
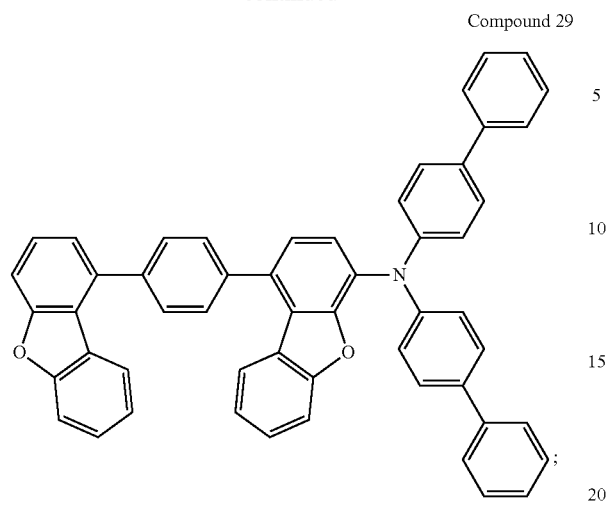
Compound 32
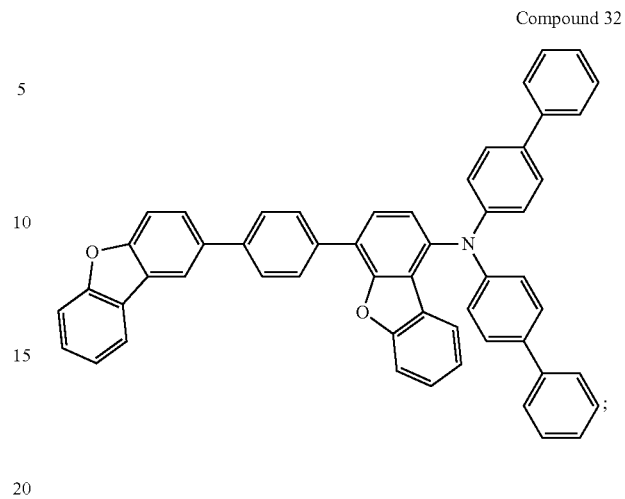
Compound 30
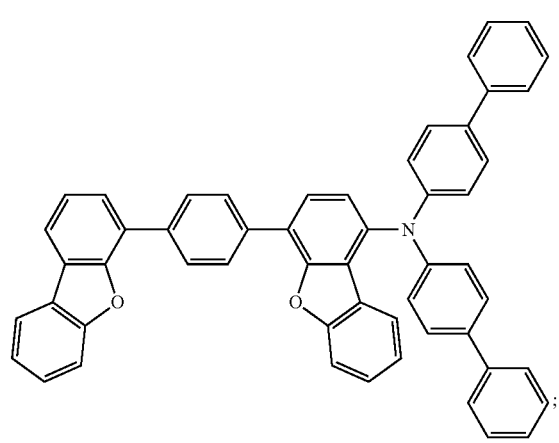
Compound 33
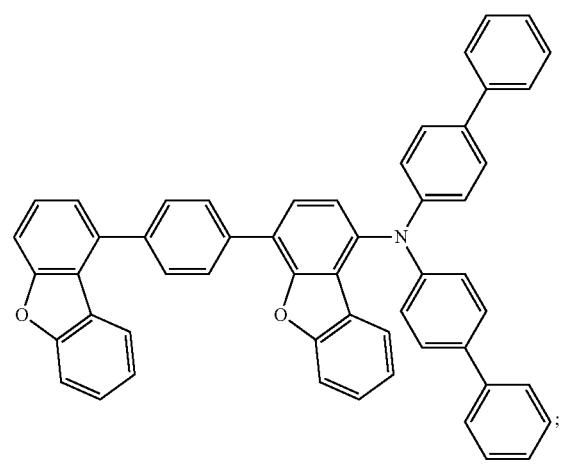
Compound 31
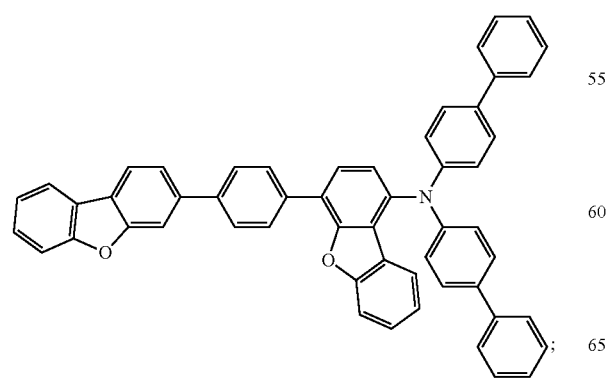
Compound 34
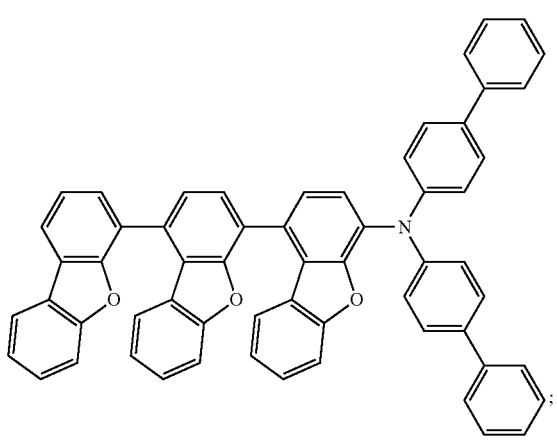

Compound 35
Compound 38
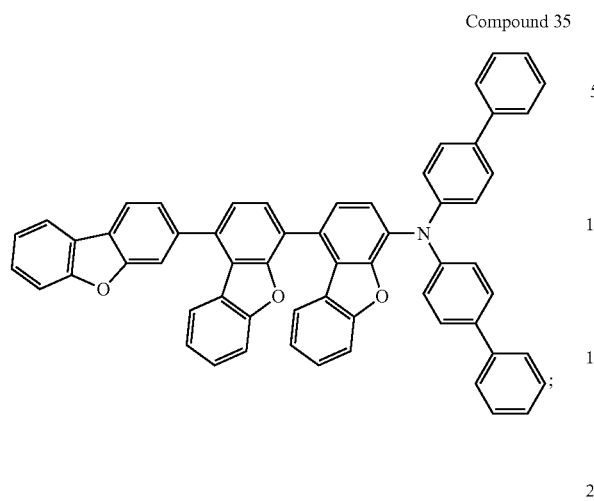
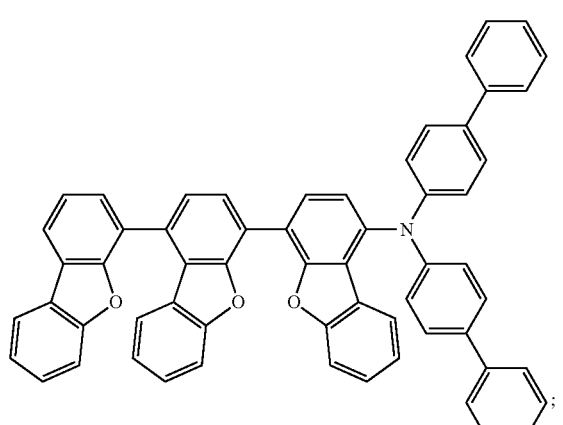
Compound 36
Compound 39
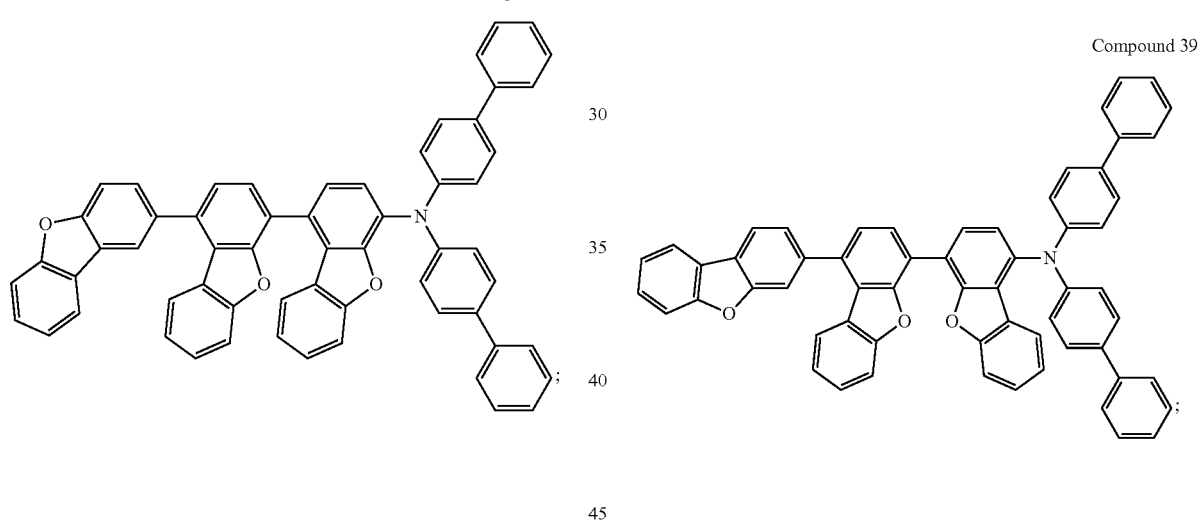
Compound 37
Compound 40
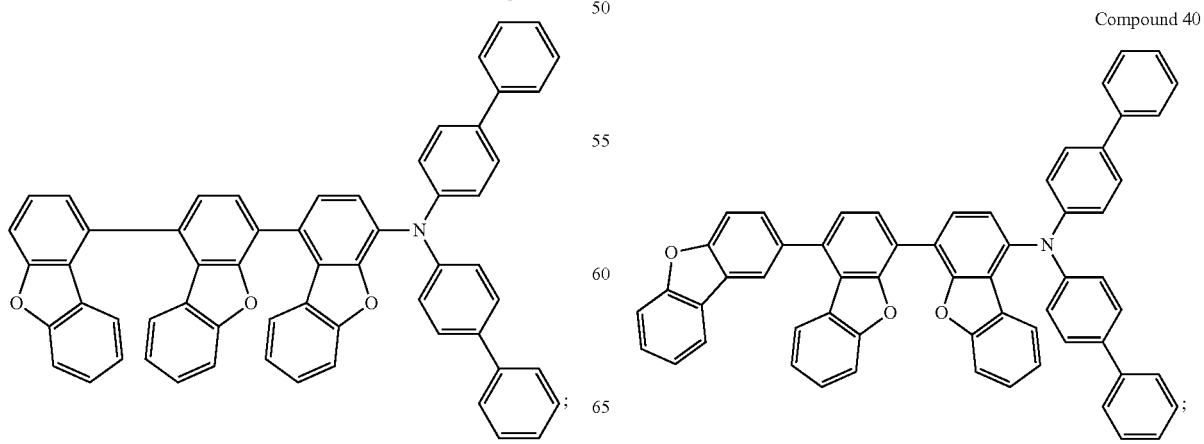

Compound 41
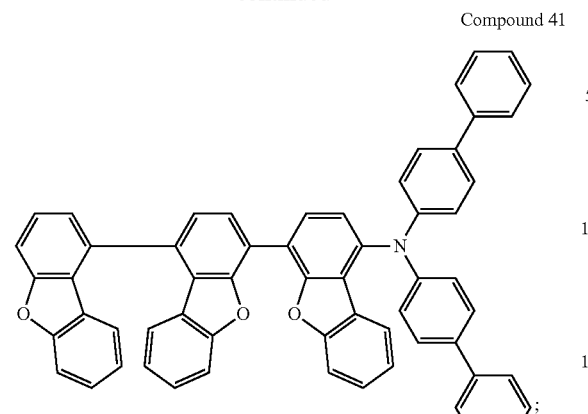
Compound 42
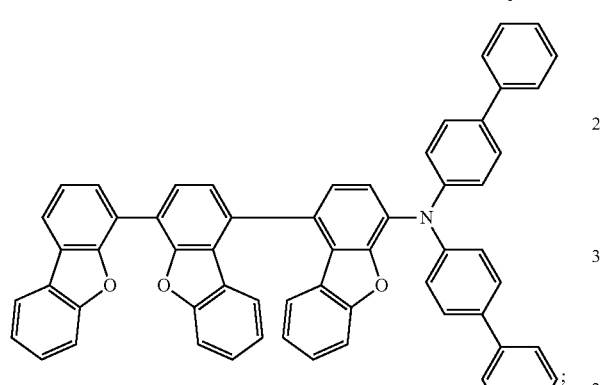
Compound 43
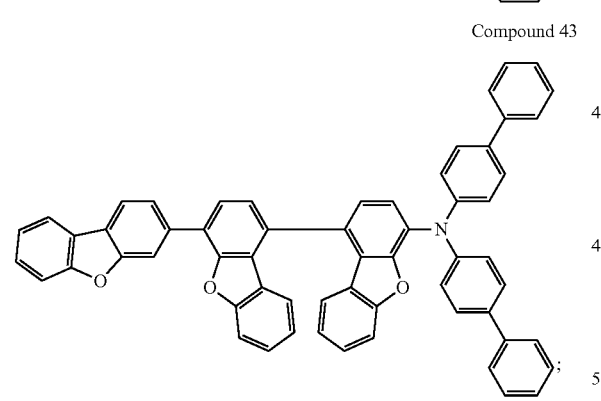
Compound 44
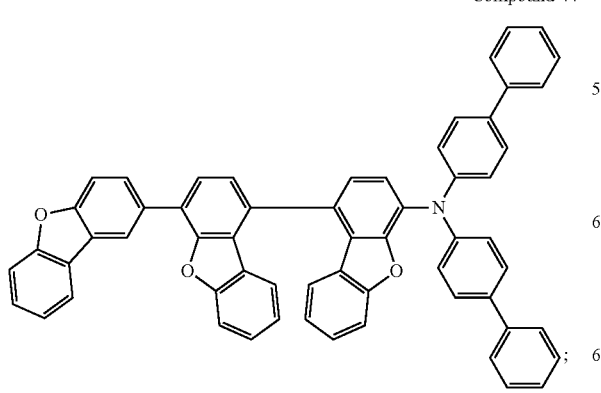
Compound 45
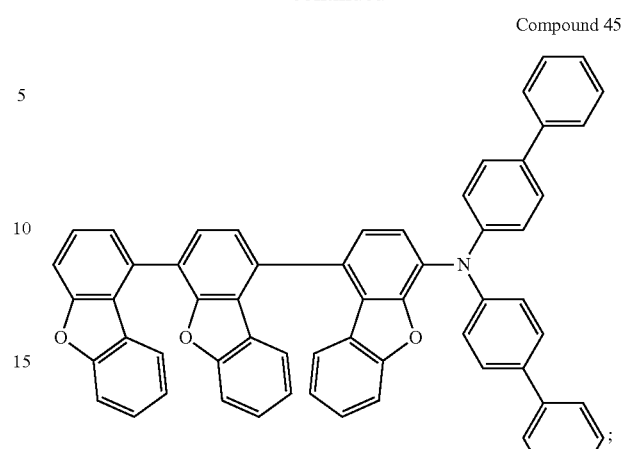
Compound 46
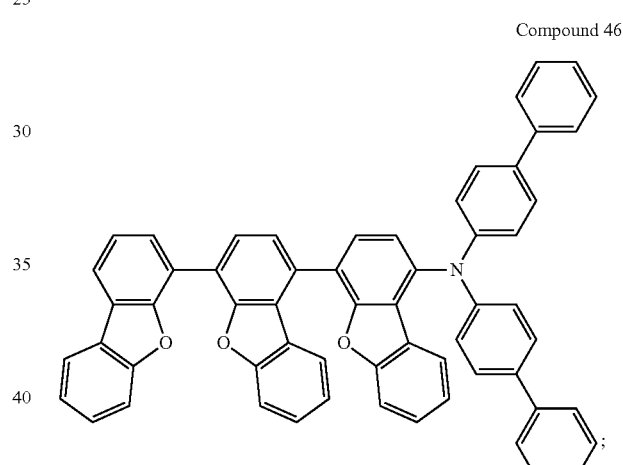
Compound 47
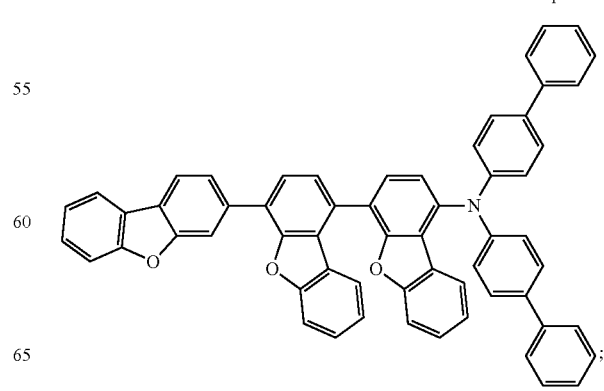

Compound 48
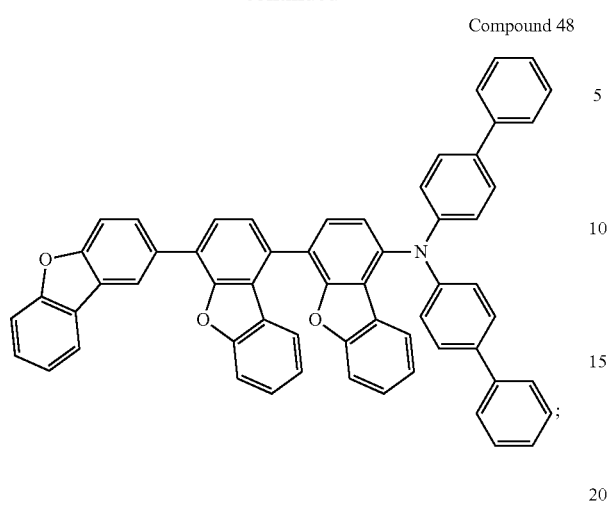
Compound 49
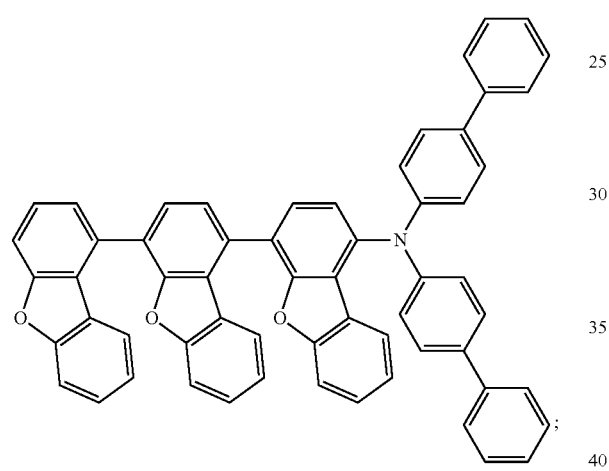
Compound 50
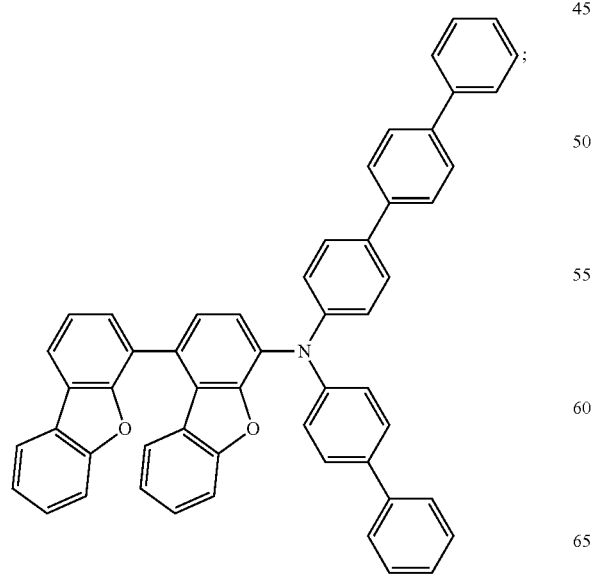
Compound 51
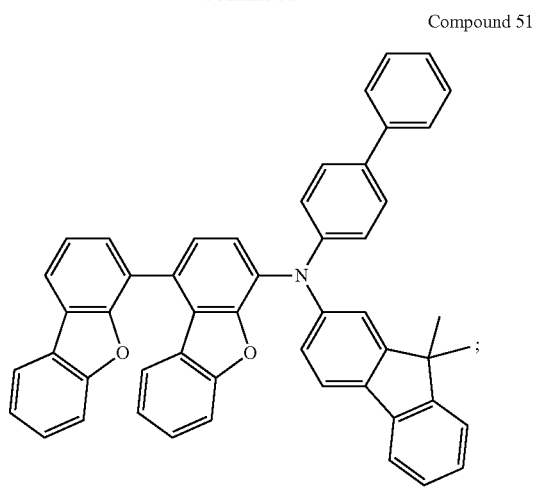
Compound 52
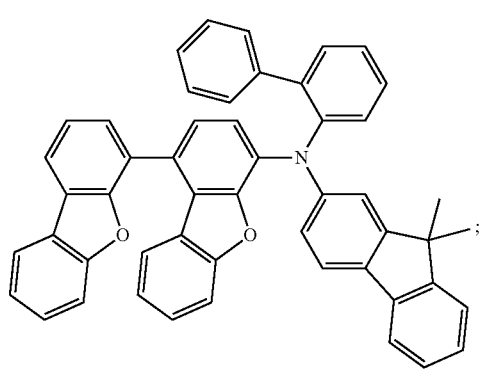
Compound 53
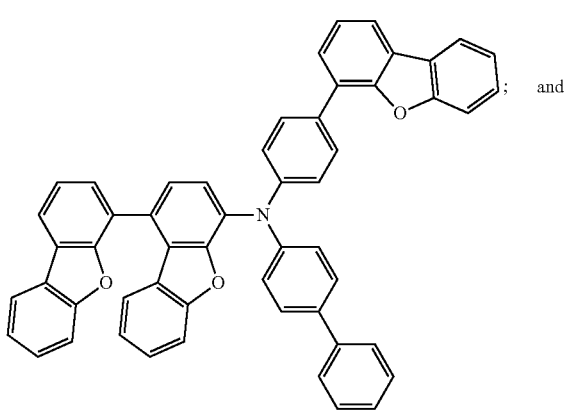

Compound 54

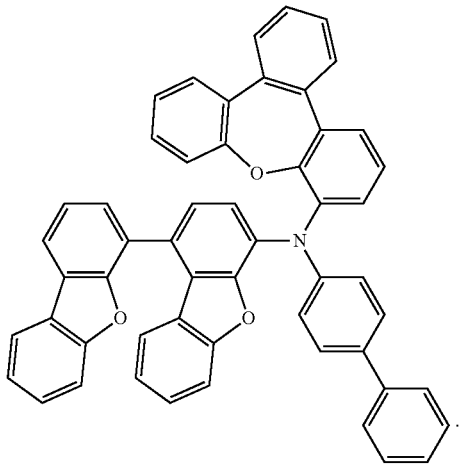

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED).

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

More preferably, the novel compound of the present invention may be used as a hole injection material of HIL or a hole transport material of HTL.

In one embodiment, the organic layer may be the hole injection layer, i.e., the hole injection layer comprises a hole injection material which is the novel compound as stated above.

For example, the hole injection layer may be a single-layered configuration or a multi-layered configuration disposed between the first electrode and the hole transport layer. When the hole injection layer is the multi-layered configuration, e.g., the hole injection layer comprises a first hole injection layer and a second hole injection layer, the first hole injection material of the first hole injection layer may be made of a single novel compound and the second hole injection material of the second hole injection layer may be made of another single novel compound or any single conventional compound.

Or, the first hole injection material of the first hole injection layer may be made of a novel compound in combination with another single novel compound or any single conventional compound, and so as the second hole injection material of the second hole injection layer.

Said first and/or second hole injection layer comprises the novel compound such as Compounds 1 to 54. The OLEDs using the novel compound as the hole injection material can have an improved efficiency compared to commercial OLEDs using known hole injection materials of HIL, such as polyaniline, polyethylenedioxythiophene, 4,4',4"-Tris[(3-methylphenyl)phenylamino]triphenylamine (m-MTDATA), or $N^1,N^{1'}$-(biphenyl-4,4'-diyl)bis($N^1$-(naphthalen-1-yl)-$N^4$, $N^{4'}$-diphenylbenzene-1,4-diamine) as the hole injection material.

In another embodiment, the organic layer may be the hole transport layer, i.e., the hole transport layer comprises a hole transport material which is the novel compound as stated above.

For example, the hole transport layer may be a single-layered configuration or a multi-layered configuration disposed between the two-layered hole injection layer and the emission layer. When the hole transport layer is the multi-layered configuration, e.g., the hole transport layer comprises a first hole transport layer and a second hole transport layer, the first hole transport material of the first hole transport layer may be made of a single novel compound and the second hole transport material of the second hole transport layer may be made of another single novel compound or any single conventional compound. Or, the first hole transport material of the first hole transport layer may be made of a novel compound in combination with another single novel compound or any single conventional compound, and so as the second hole transport material of the second hole transport layer.

Said first and/or second hole transport layer comprises the novel compound such as Compounds 1 to 54. The OLEDs using the novel compound as the hole transport material can have an improved efficiency compared to commercial OLEDs using known hole transport materials of HTL, such as 1,1-bis[(di-4-tolylamino)phenylcyclohexane](TAPC), a carbazole derivative such as N-phenyl carbazole, and $N^4,N^{4'}$-di(naphthalen-1-yl)-$N^4$,N4'-diphenylbiphenyl-4,4'-diamine (NPB), as the hole transport material.

Preferably, the emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having quinoline derivative ligands or isoquinoline derivative ligands; an osmium complex; or a platinum complex. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: an aminoperylene derivative; a diaminochrysene; a diaminopyrene; or organicmetallic compounds of iridium (II) having pyridinato picolinate ligands. With various host materials of the emission layer, the OLED can emit lights in red, green or blue.

Preferably, the electron transport layer is made of 3,3'-[5'-[3-(3-Pyridinyl)phenyl][1,1':3',1"-terphenyl]-3,3"-diyl] bispyridine (TmPyPb), 3-(Biphenyl-4-yl)-5-(4-tert-butylphenyl)-4-phenyl-4H-1,2,4-triazole (TAZ), 1,3,5-tris (1-phenyl-1H-benzimidazol-2-yl)benzene (TPBi), tris(2,4, 6-trimethyl-3-(pyridin-3-yl)phenyl)borane (3TPYMB), 1,3-bis(3,5-dipyrid-3-yl-phenyl)benzene (BmPyPb), and 9,10-bis(3-(pyridin-3-yl)phenyl)anthracene (DPyPA), but it is not limited thereto.

Preferably, the OLED comprises a hole blocking layer formed between the electron transport layer and the emission layer, to block holes overflow from the emission layer to the electron transport layer. Said hole blocking layer may be made of 2,9-dimethyl-4,7-diphenyl-1,10-phenanthroline (BCP) or 2,3,5,6-tetramethyl-phenyl-1,4-(bis-phthalimide) (TMPP), but not limited thereto.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4"-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
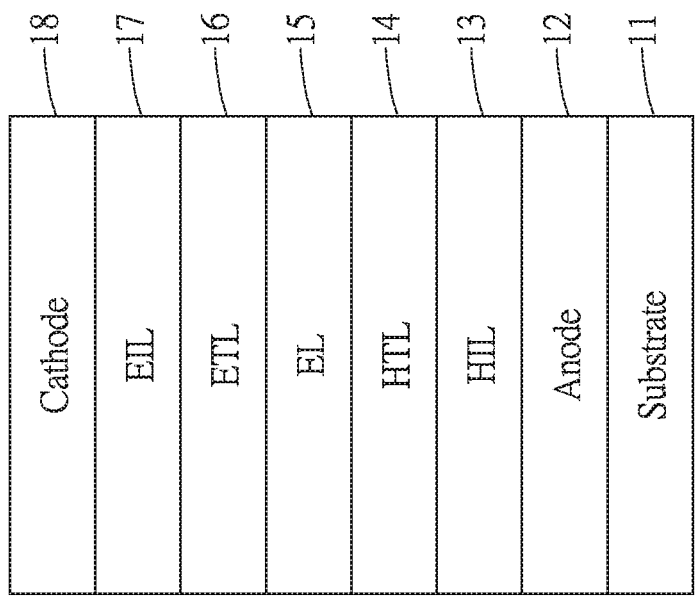
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate An

Intermediate An used for preparing a novel compound was synthesized by the following steps.

Synthesis of Intermediate An-2

In step 1, the general synthesis pathway of Intermediate An-2 was summarized in Scheme A1.

Scheme A1

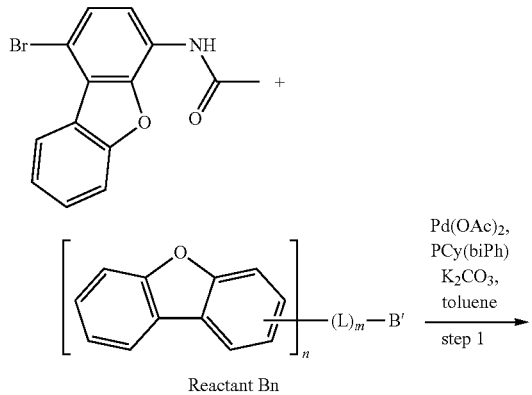

Wherein B' is B(OH)$_2$ group or group; L is a substituted or unsubstituted arylene group having 6 to 60 ring carbon atoms; m is an integer 0 or 1; n is an integer 1 or 2.

Synthesis of Intermediate A1-2

Taking Intermediate A1-2 as an example of Intermediate An-2, the synthesis pathway of Intermediate A1-2 was summarized in Scheme A1-1.

Scheme A1-1

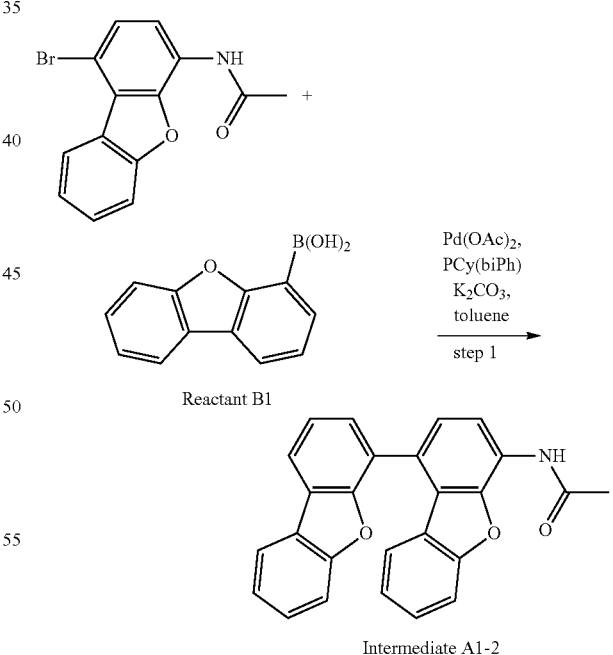

Intermediate A1-2

A mixture of 1-bromo-4-acetamidodibenzofuran (30.0 g, 1.0 eq), 4-dibenzofuranboronic acid (1.25 eq), Palladium(II) acetate [Pd(OAc)$_2$] (0.01 eq), 2-(dicyclohexylphosphino)biphenyl [PCyz(2-biPh)] (0.04 eq), and potassium carbonate (K$_2$CO$_3$) (2.0 eq) was in a mixed solution of toluene (165 mL), ethanol (16.5 mL) and H$_2$O (60.0 mL). The reaction mixture was heated to about 80° C. under reflux and stirred for 16 hours under nitrogen atmosphere. After the completion of the reaction, the reaction mixture was cooled to room temperature, and the crude product was extracted and collected by the organic layer. The organic layer was dried over MgSO₄, separated by filtration and concentrated to dryness. A resulting residue was purified by silica gel column chromatography to obtain 34.5 g of white solid product in yield 90.25%.

The white solid product was identified as Intermediate A1-2 by a field desorption mass spectroscopy (FD-MS) analysis. FD-MS analysis: $C_{26}H_{17}NO_3$: theoretical value 391.42 and observed value 391.42.

Syntheses of Intermediates A2-2 to A6-2

Intermediates A2-2 to A6-2, which also can be used for preparing a novel compound, were respectively synthesized in a similar manner as Intermediate A1-2 through step 1, except that the starting material Reactant B1 was replaced with Reactants B2 to B6, respectively. All intermediates were analyzed as described above, and the results were listed in Table 1.

TABLE 1

Reactant Bn used for preparing Intermediates A1-2 to A6-2, and the chemical structures, yields, formulae, and mass analyzed by FD-MS of Intermediates A1-2 to A6-2.

| Chemical Structure of Reactant Bn | Chemical Structure of Intermediate An-2 | Yield (%) | Formula/ Mass (M⁺) |
|---|---|---|---|
| 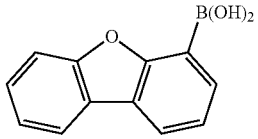<br>B1 | 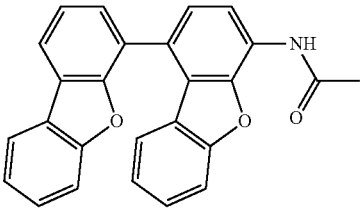<br>A1-2 | 90.25 | $C_{26}H_{17}NO_3$<br>391.42 |
| 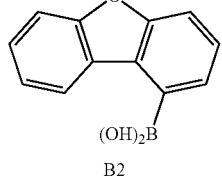<br>B2 | 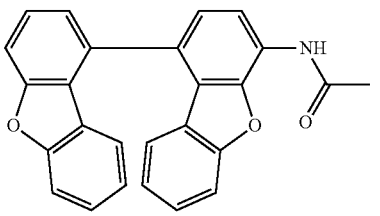<br>A2-2 | 90.0 | $C_{26}H_{17}NO_3$<br>391.42 |
| 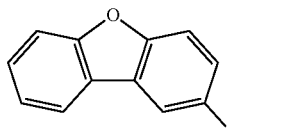<br>B3 | 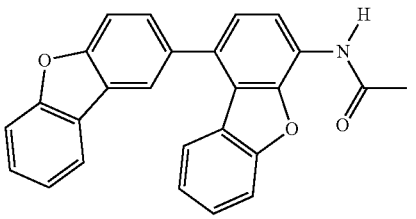<br>A3-2 | 91.5 | $C_{26}H_{17}NO_3$<br>391.42 |
| 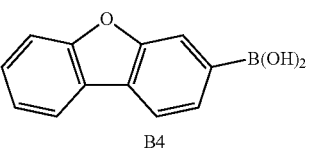<br>B4 | 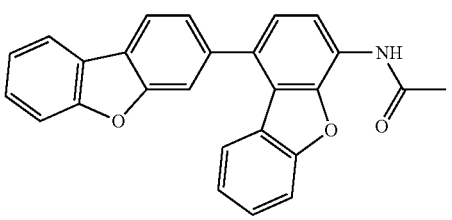<br>A4-2 | 93.0 | $C_{26}H_{17}NO_3$<br>391.42 |

TABLE 1-continued

Reactant Bn used for preparing Intermediates A1-2 to A6-2, and the chemical structures, yields, formulae, and mass analyzed by FD-MS of Intermediates A1-2 to A6-2.

| Chemical Structure of Reactant Bn | Chemical Structure of Intermediate An-2 | Yield (%) | Formula/Mass (M+) |
|---|---|---|---|
| 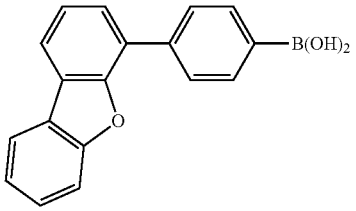<br>B5 | 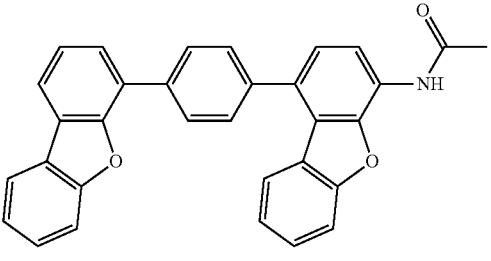<br>A5-2 | 87.6 | $C_{32}H_{21}NO_3$, 467.51 |
| 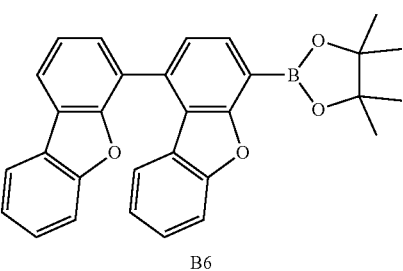<br>B6 | 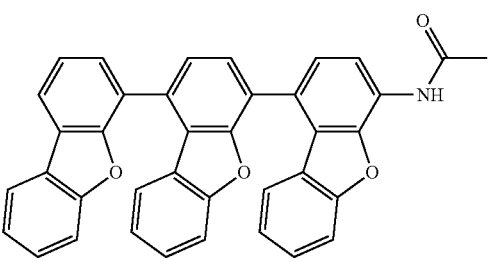<br>A6-2 | 81.7 | $C_{38}H_{23}NO_4$, 557.59 |

In the above Table 1, Reactant B6 is also named Intermediate A1-B below, which can be synthesized through steps 1 to 4 from a starting material, Reactant B1.

Modifications of Intermediates A1-2 to A6-2 In addition to Intermediates A1-2 to A6-2, one person skilled in the art can adopt other applicable starting materials and successfully synthesize other desired intermediates through a reaction mechanism similar to Scheme A1-1. When reacting a starting material like Reactant B5, which contains a phenylene group between the dibenzofuranyl group and the —B(OH)₂ group, with bromo acetamidodibenzofuran, an intermediate which contains two dibenzofuranyl moieties and a phenylene group inserted there-between could be synthesized. When reacting a starting material like Reactant B6, which contains two bonded dibenzofuranyl groups, with bromo acetamidodibenzofuran, an intermediate which contains three dibenzofuranyl moieties linked together could be synthesized.

Synthesis of Intermediate An-3

In step 2, the general synthesis pathway of Intermediate An-3 was summarized in Scheme A2.

Scheme A2

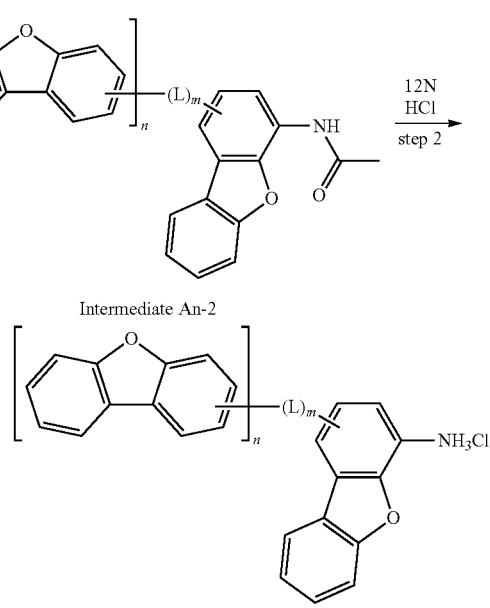

Intermediate An-2

Intermediate An-3

In Scheme A2, L, m, and n are as stated in Scheme A1.

Synthesis of Intermediate A1-3

Taking Intermediate A1-3 as an example of Intermediate An-3, the synthesis pathway of Intermediate A1-3 was summarized in Scheme A2-1.

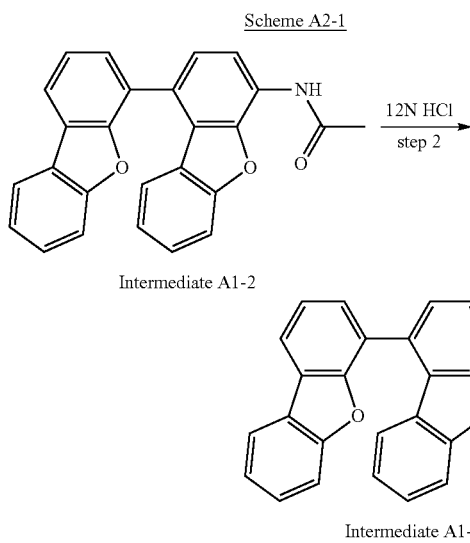

Scheme A2-1

Intermediate A1-2 (55 g, 1.0 eq) dissolved in 12N HCl (100 mL) was stirred magnetically in 275 mL ethanol at reflux temperature for 8 hours, and then the reaction mixture was cooled to room temperature. The crude solid product was separated by filtration, washed with $H_2O$ and dried. The yield of step 2 was 98.5%.

The product was identified as Intermediate A1-3 by a FD-MS analysis. FD-MS analysis: $C_{24}H_{16}ClNO_2$: theoretical value 385.84 and observed value 385.84.

Syntheses of Intermediates A2-3 to A6-3

Intermediates A2-3 to A6-3, which also can be used for preparing a novel compound, were respectively synthesized in a similar manner as Intermediate A1-3 through step 2, except that the starting material Intermediate A1-2 was replaced by Intermediates A2-2 to A6-2, respectively. All intermediates were analyzed as described above, and the results were listed in Table 2.

TABLE 2

The chemical structures, yields, formulae, and mass analyzed by FD-MS of Intermediates A1-3 to A6-3.

| Intermediate An-3 No. | Chemical Structure of Intermediate An-3 | Yield (%) | Formula/ Mass (M+) |
|---|---|---|---|
| A1-3 | | 98.5 | $C_{24}H_{16}ClNO_2$ 385.84 |
| A2-3 | | 97.1 | $C_{24}H_{16}ClNO_2$ 385.84 |
| A3-3 | | 98.0 | $C_{24}H_{16}ClNO_2$ 385.84 |

TABLE 2-continued

The chemical structures, yields, formulae, and mass analyzed by FD-MS of Intermediates A1-3 to A6-3.

| Intermediate An-3 No. | Chemical Structure of Intermediate An-3 | Yield (%) | Formula/Mass (M+) |
|---|---|---|---|
| A4-3 | | 96.5 | $C_{24}H_{16}ClNO_2$ 385.84 |
| A5-3 | | 97.0 | $C_{30}H_{20}ClNO_2$ 461.94 |
| A6-3 | | 95.5 | $C_{36}H_{22}ClNO_3$ 552.02 |

Modifications of Intermediates A1-3 to A6-3

In addition to Intermediates A1-3 to A6-3, one person skilled in the art can adopt other applicable starting materials and successfully synthesize other desired intermediates through a reaction mechanism similar to Scheme A2-1.

Synthesis of Intermediate an

In step 3, the general synthesis pathway of Intermediate An was summarized in Scheme A3.

Scheme A3

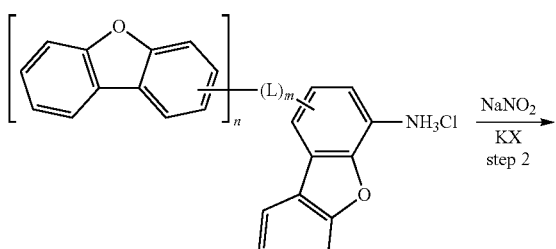

Intermediate An-3

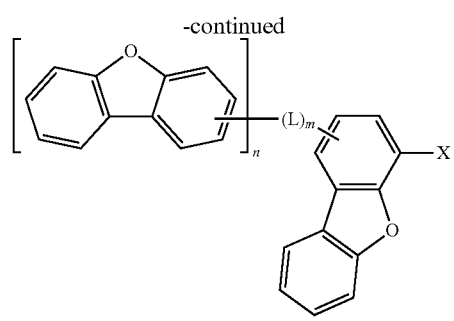

Intermediate An

X: Cl, Br, or I

In Scheme A3, L, m, and n are as stated in Scheme A1.
Synthesis of Intermediate A1 Taking Intermediate A1 as an example of Intermediate An, the synthesis pathway of Intermediate A1 was summarized in Scheme A3-1.

Scheme A3-1

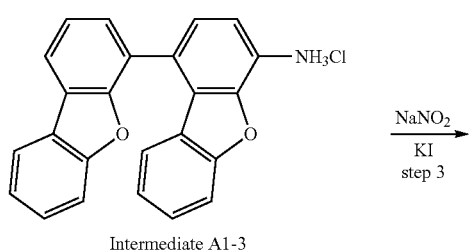

Intermediate A1-3

-continued

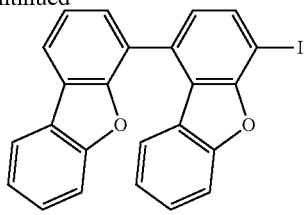
Intermediate A1

Intermediate A1-3 (10.0 g, 1.0 eq) was added in a mixed solution of 12N HCl (40 mL) and $CH_3CN$ (130 mL), and cooled to lower than 5° C. An aqueous solution of sodium nitrite ($NaNO_2$) (2.0 eq) and potassium iodide (KI) (2.5 eq) in 15.0 mL $H_2O$ was slowly added to the foresaid cooled solution, and the reaction mass was stirred for 10 min, and then its temperature was raised to 20° C. and the reaction mass was stirred overnight. After that, the pH value of the solution was adjusted by saturated solution of sodium hydrogen carbonate ($NaHCO_3$) and sodium thiosulfate ($Na_2S_2O_3$) (2.5 eq) until the pH was between 9 and 10. The precipitate was separated by filtration or extracted with ethyl acetate, and then purified by flash chromatography with eluent (hexane to $CH_2Cl_2$ is 5 to 1) to get a grey solid product. The yield of step 3 was 85.7%.

The grey solid product was identified as Intermediate A1 by a FD-MS analysis. FD-MS analysis: $C_{24}H_{13}IO_2$: theoretical value 460.26 and observed value 460.26.

Syntheses of Intermediates A2 to A6

Intermediates A2 to A6, which also can be used for preparing a novel compound, were respectively synthesized in a similar manner as Intermediate A1 through step 3, except that the starting material Intermediate A1-3 was replaced by Intermediates A2-3 to A6-3, respectively. All intermediates were analyzed as described above, and the results were listed in Table 3.

TABLE 3

The chemical structures, yields, formulae, and mass analyzed by FD-MS of Intermediates A1 to A6.

| Intermediate An No. | Chemical Structure of Intermediate An | Yield (%) | Formula/ Mass (M+) |
|---|---|---|---|
| A1 | | 85.7 | $C_{24}H_{13}IO_2$ 460.26 |
| A2 | | 81.2 | $C_{24}H_{13}IO_2$ 460.26 |
| A3 | | 83.4 | $C_{24}H_{13}IO_2$ 460.26 |
| A4 | | 84.6 | $C_{24}H_{13}IO_2$ 460.26 |

TABLE 3-continued

The chemical structures, yields, formulae, and mass analyzed by FD-MS of Intermediates A1 to A6.

| Intermediate An No. | Chemical Structure of Intermediate An | Yield (%) | Formula/ Mass (M+) |
|---|---|---|---|
| A5 | 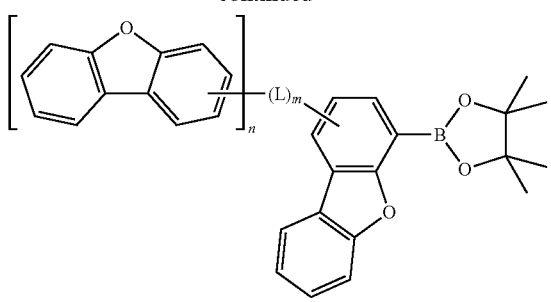 | 82.6 | $C_{30}H_{17}IO_2$ 536.36 |
| A6 | | 67.4 | $C_{36}H_{19}IO_3$ 626.44 |

Modifications of Intermediates A1 to A6

In addition to Intermediates A1 to A6, one person skilled in the art can adopt other applicable starting materials and successfully synthesize other desired intermediates through a reaction mechanism similar to Scheme A3-1.

Synthesis of Intermediate An-B

In step 4, the general synthesis pathway of Intermediate An-B was summarized in Scheme A4.

Scheme A4

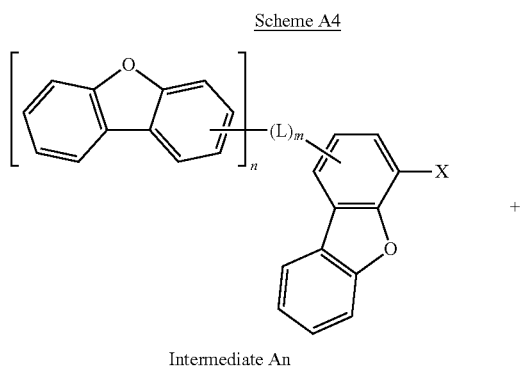

Intermediate An

Intermediate An-B

In Scheme A4, L, m, and n are as stated in Scheme A1, and X is as stated in Scheme A3.

Synthesis of Intermediate A1-B

Taking Intermediate A1-B as an example of Intermediate An-B, the synthesis pathway of Intermediate A1-B was summarized in Scheme A4-1.

Scheme A4-1

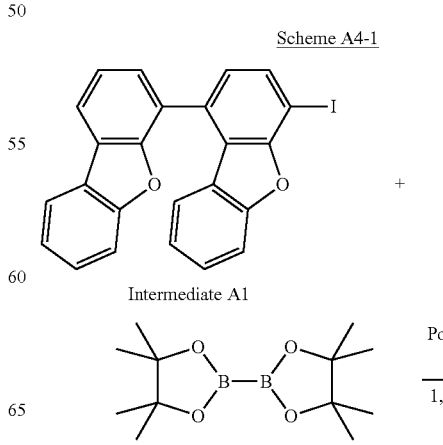

Intermediate A1

Intermediate A1-B

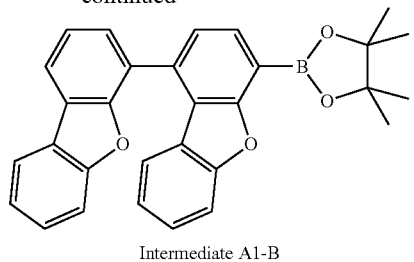

A mixture of Intermediate A1 (30.0 g, 1.0 eq), bis(pinacolato)diboron (1.20 eq), 1,1'-bis(diphenylphosphino)-ferrocene dichloropalladium (II) [PdCl$_2$(dppf)] (0.02 eq), and potassium acetate (KOAc) (2.0 eq) in 1,4-dioxane (165 mL) was stirred at 95° C. for 16 hours under nitrogen atmosphere. After cooling to room temperature, the crude product was extracted with H$_2$O and collected by the organic layer. The organic layer was dried over MgSO$_4$, separated by filtration and then concentrated to dryness. A resulting residue was purified by silica gel column chromatography to obtain 34.5 g of white solid product. The yield of step 4 was 91.35%.

The white solid product was identified as Intermediate A1-B by a FD-MS analysis. FD-MS analysis: C$_{30}$H$_{25}$BO$_4$: theoretical value 460.33 and observed value 460.33.

Modifications of Intermediate A1-B

In addition to Intermediate A1-B, one person skilled in the art can adopt other starting materials and successfully synthesize other desired intermediates through a reaction mechanism similar to Scheme A4-1.

Applicable modifications of Intermediate A1-B may be, for example, but not limited to, Intermediates A2-B to A6-B as follows.

Intermediate A2-B

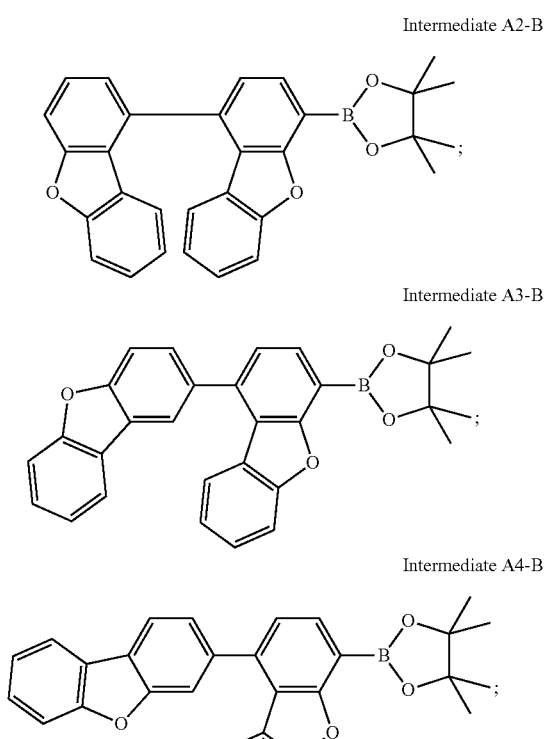

Intermediate A3-B

Intermediate A4-B

Intermediate A5-B

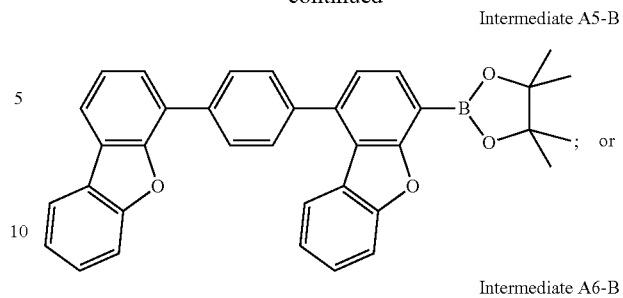

; or

Intermediate A6-B

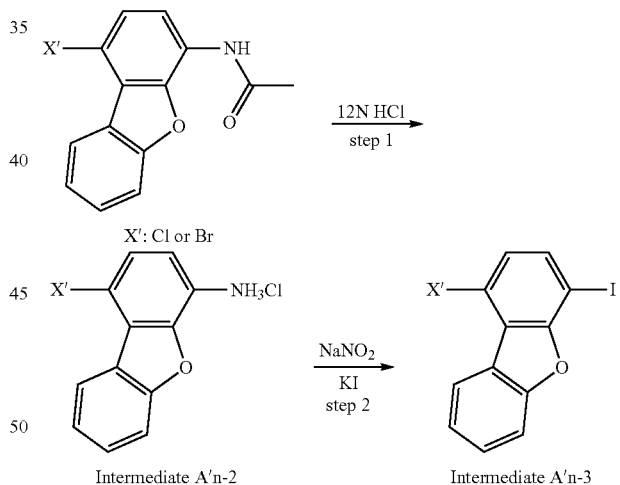

Intermediate An used for preparing a novel compound can also be synthesized by the following steps.

Synthesis of Intermediate A'n-3

Intermediate A'n-3 used for preparing a novel compound was synthesized by the following steps. The general synthesis pathway of Intermediate A'n-3 was summarized in Scheme A5.

Scheme A5

Intermediate A'n-2

Intermediate A'n-3

Step 1: Synthesis of Intermediate A'7-2

Taking Intermediate A'7-2 as an example of Intermediate A'n-2, the synthesis pathway of Intermediate A'7-2 was summarized in Scheme A5 as X' is Br.

1-Bromo-4-acetamidodibenzofuran (55 g, 1.0 eq) dissolved in 12N HCl (100 mL) was stirred magnetically in 275 mL ethanol at reflux temperature for 8 hours, and then the reaction mixture was cooled to room temperature. The crude solid product was separated by filtration, washed with H$_2$O and dried. The yield of step 1 was 97%.

The product was identified as Intermediate A'7-2 by a FD-MS analysis. FD-MS analysis: C$_{12}$H$_9$BrClNO: theoretical value 298.56 and observed value 298.56.

Step 2: Synthesis of Intermediate A'7-3

Intermediate A'7-2 (60.0 g, 1.0 eq) was added in a mixed solution of 12N HCl (50 mL) and $CH_3CN$ (240 mL), and cooled to lower than 5° C. An aqueous solution of $NaNO_2$ (2.0 eq) and KI (2.5 eq) in 400 mL $H_2O$ was slowly added to the foresaid cooled solution, and the reaction mass was stirred for 10 min, and then its temperature was raised to 20° C. and the reaction mass was stirred overnight. After that, the pH value of the solution was adjusted by saturated solution of $NaHCO_3$ and $Na_2S_2O_3$ (2.5 eq) until the pH value of the solution was between 9 and 10. The precipitate was separated by filtration or extracted with ethyl acetate, and then purified by flash chromatography with eluent (hexane to $CH_2Cl_2$ is 5 to 1) to get a grey solid product. The yield of step 2 was 83.2%.

The grey solid product was identified as Intermediate A'7-3 by a FD-MS analysis. FD-MS analysis: $C_{12}H_6BrIO$: theoretical value 372.98 and observed value 372.98.

Synthesis of Intermediate an

Intermediate An used for preparing a novel compound was synthesized by the following step. The general synthesis pathway of Intermediate An was summarized in Scheme A6.

Scheme A6

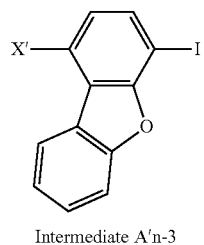

Intermediate A'n-3

+

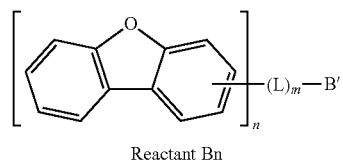

Reactant Bn

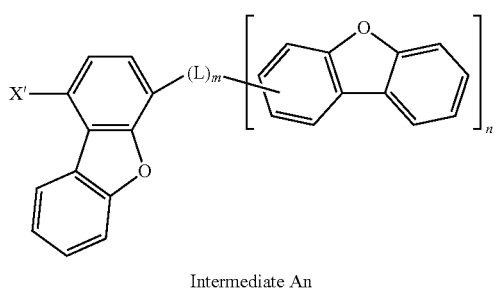

Intermediate An

In Scheme A6, B', L, m, and n are as stated in Scheme A1, and X' is as stated in Scheme A5.

Step 3: Synthesis of Intermediate A7

Taking Intermediate A7 as an example of Intermediate An, the synthesis pathway of Intermediate A7 was summarized in Scheme A6-1.

Scheme A6-1

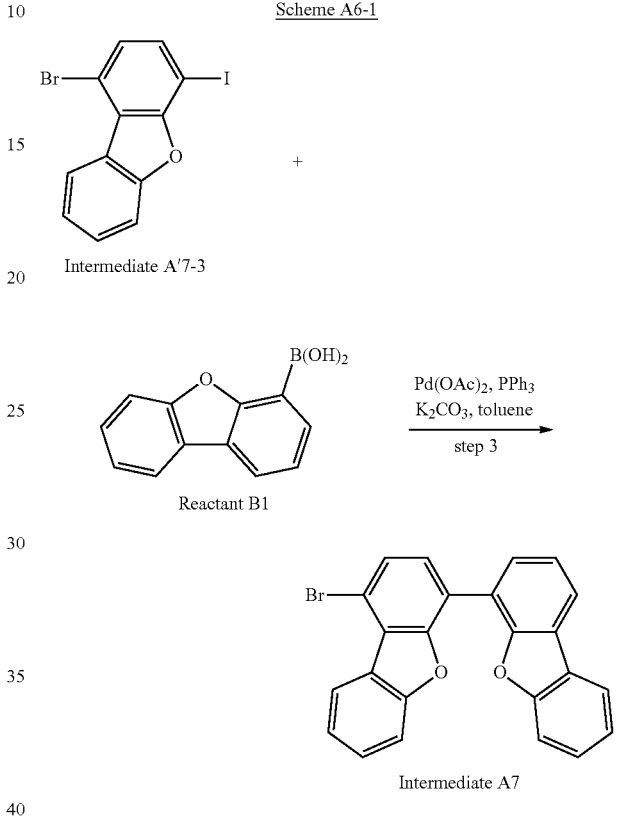

A mixture of Intermediate A'7-3 (1-bromo-4-iododibenzofuran (30.0 g, 1.0 eq), 4-dibenzofuranboronic acid (1.25 eq), $Pd(OAc)_2$ (0.01 eq), triphenylphosphine ($PPh_3$) (0.04 eq), and $K_2CO_3$ (2.0 eq) was in a mixed solution of toluene (260 mL), ethanol (26 mL) and $H_2O$ (55 mL). The reaction mixture was heated to about 80° C. under reflux and stirred for 16 hours under nitrogen atmosphere. After completion of the reaction, the reaction mixture was cooled to room temperature, and the crude product was extracted and collected by the organic layer. The organic layer was dried over $MgSO_4$, separated by filtration and concentrated to dryness. A resulting residue was purified by silica gel column chromatography to obtain 29.3 g of white solid product. The yield of step 3 was 88.15%.

The white solid product was identified as Intermediate A7 by a FD-MS analysis. FD-MS analysis: $C_{24}H_{13}BrO_2$: theoretical value 413.26 and observed value 413.26.

Synthesis of Intermediate A8

Intermediate A8 used for preparing a novel compound was synthesized in a similar manner as Intermediate A7 through step 3, except that the starting material Reactant B1 was replaced by Reactant B2. All intermediates were analyzed as described above, and the results were listed in Table 4.

TABLE 4

Reactant Bn used for preparing Intermediates A7 and A8, and the chemical structures, yields, formulae, and mass analyzed by FD-MS of Intermediates A7 and A8.

| Chemical Structure of Reactant Bn | Chemical Structure of Intermediate An | Yield (%) | Formula/ Mass (M+) |
|---|---|---|---|
| 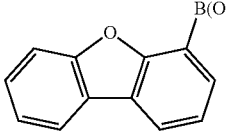<br>B1 | 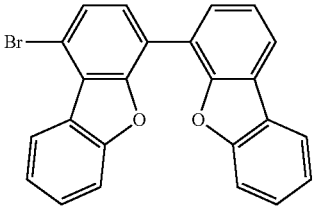<br>A7 | 88.15 | $C_{24}H_{13}BrO_2$<br>413.26 |
| 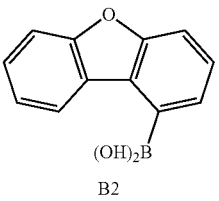<br>B2 | 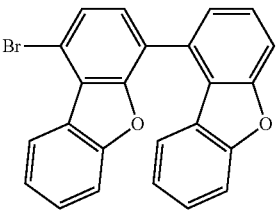<br>A8 | 86.3 | $C_{24}H_{13}BrO_2$<br>413.26 |

Modifications of Intermediates A7 and A8

In addition to Intermediates A7 and A8, one person skilled in the art can adopt other starting materials and successfully synthesize other desired intermediates through a reaction mechanism similar to Scheme A6-1. Applicable modifications of Intermediates A7 and A8 may be, for example, but not limited to, Intermediates A9 to A12 as follows.

Intermediate A9

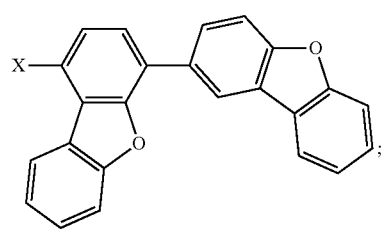

Intermediate A10

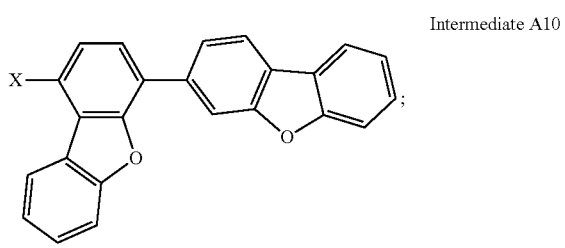

-continued

Intermediate A11

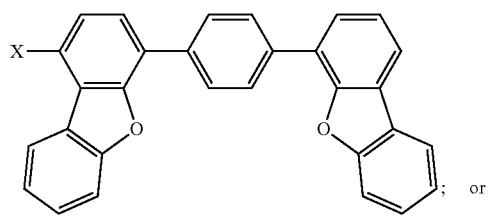; or

Intermediate A12

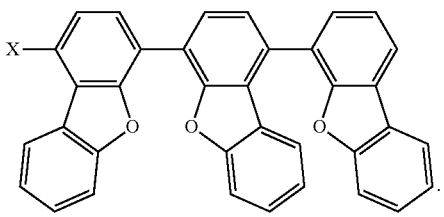.

Synthesis of Intermediate An-L

The foresaid Intermediate An, for example, Intermediates A1 to A12 could be further inserted with a phenylene group to obtain Intermediate An-L through step 4'-1.

Intermediate An-L used for preparing a novel compound was synthesized by the following steps. The general synthesis pathway of the Intermediate An-L was summarized in Scheme A4-L.

Scheme A4-L
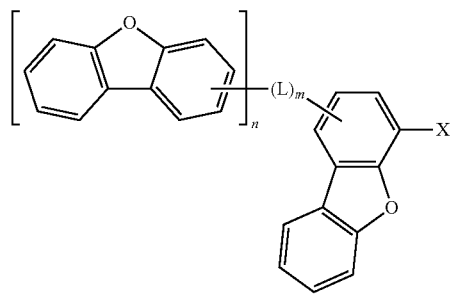
or
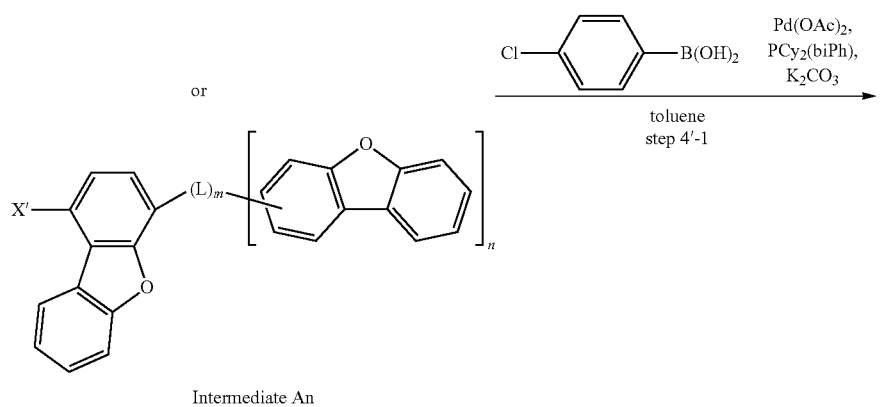
Intermediate An
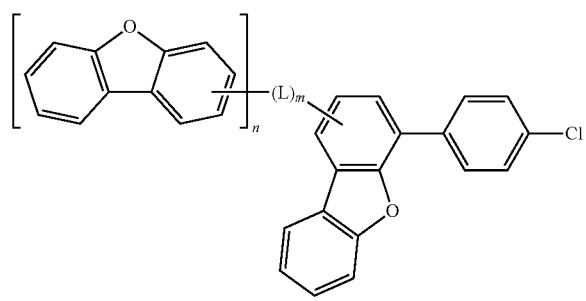
or
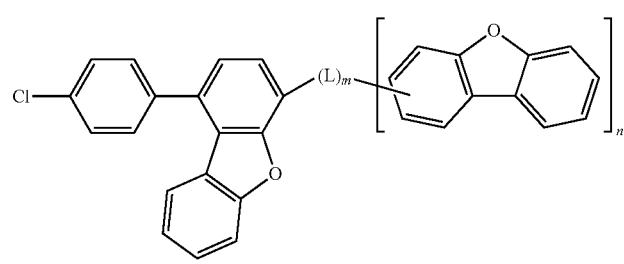
Intermediate An-L In Scheme A4-L, L, m, and n are as stated in Scheme A1; X is Cl, Br, or I; and X' is Cl or Br.

Step 4'-1: Synthesis of Intermediate A1-L

Taking Intermediate A1-L as an example of Intermediate An-L, the synthesis pathway of the Intermediate A1-L was summarized in Scheme A4-1-L.

Scheme A4-1-L

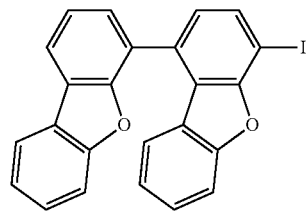 [SMILES: Ic1ccc(-c2cccc3c2oc2ccccc23)c2c1oc1ccccc12]

Intermediate A1

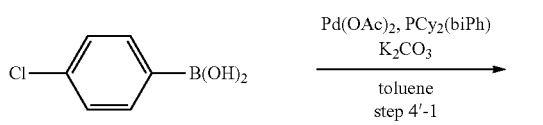

Intermediate A1-L

A mixture of Intermediate A1 (1-(dibenzofuran-4-yl)-4-iododibenzofuran) (50.0 g, 1.0 eq), 4-chlorophenylboronic acid (1.05 eq, CAS No. 1679-18-1), Pd(OAc)$_2$ (0.01 eq), PCyz(2-biPh) (0.04 eq), and K$_2$CO$_3$ (2.0 eq) was in a mixed solution of toluene (340 mL), ethanol (34 mL) and H$_2$O (72 mL). The reaction mixture was heated to about 80° C. under reflux and stirred for 16 hours under nitrogen atmosphere. After the completion of the reaction, the reaction mixture was cooled to room temperature, and the crude product was extracted and collected by the organic layer. The organic layer was dried over MgSO$_4$, separated by filtration and concentrated to dryness. A resulting residue was purified by silica gel column chromatography to obtain 43 g of white solid product. The yield of step 4'-1 was 89%.

The white solid product was identified as Intermediate A1-L by a FD-MS analysis. FD-MS analysis: C$_{30}$H$_{17}$ClO$_2$: theoretical value 444.91 and observed value 444.91.

Modifications of Intermediates A1-L

In addition to Intermediate A1-L, one person skilled in the art can adopt other starting materials such as Intermediates A2 to A12 or different chlorophenylboronic acids with chloro group on different positions, and successfully synthesize other desired intermediates through a reaction mechanism similar to Scheme A4-1-L. Applicable modifications of Intermediate A1-L may be, for example, but not limited to, Intermediates A2-L to A19-L as follows.

Intermediate A2-L

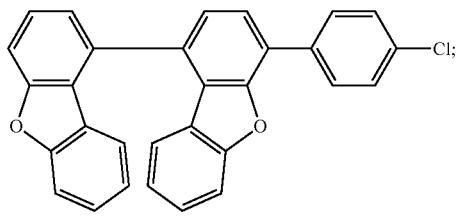

Intermediate A3-L

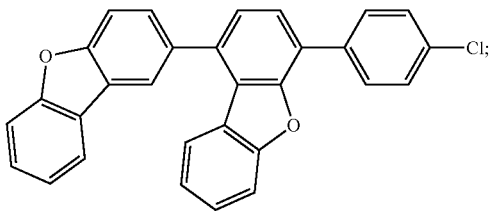

Intermediate A4-L

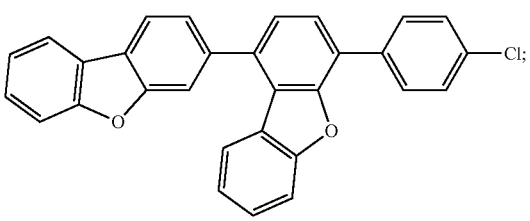

Intermediate A5-L

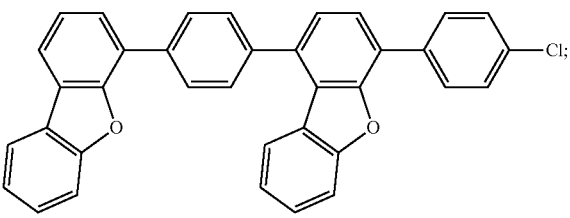

Intermediate A6-L

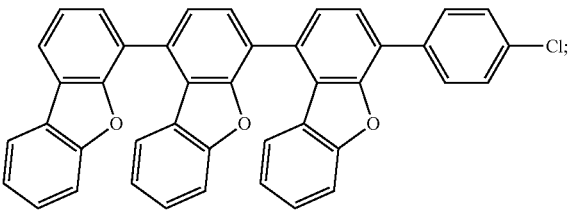

Intermediate A7-L

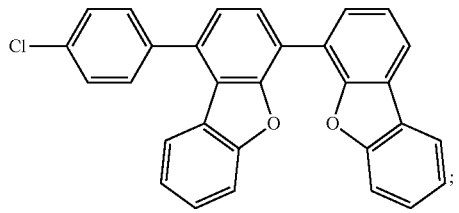

-continued
Intermediate A8-L
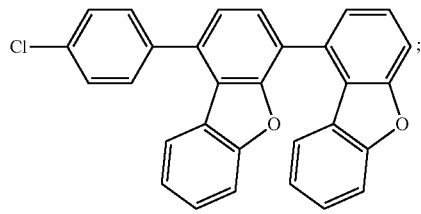
Intermediate A9-L
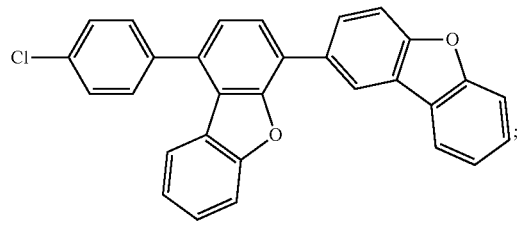
Intermediate A10-L
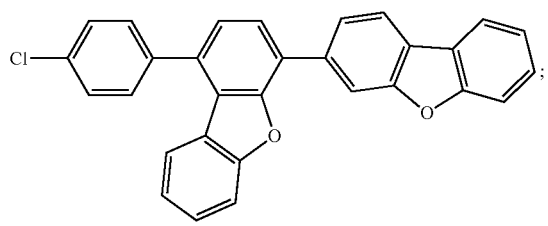
Intermediate A11-L
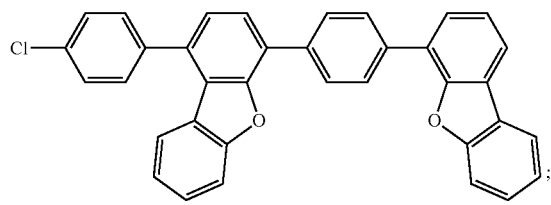
Intermediate A12-L
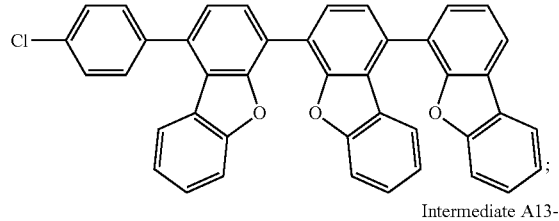
Intermediate A13-L
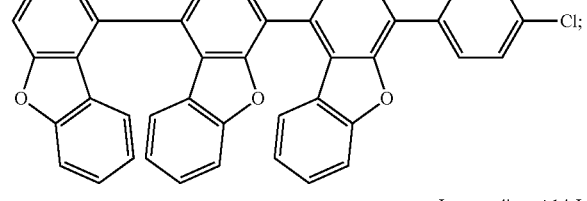
Intermediate A14-L
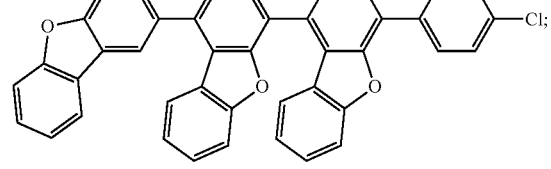
Intermediate A15-L
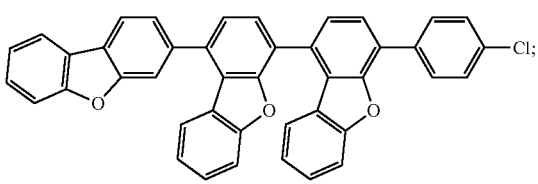
Intermediate A16-L
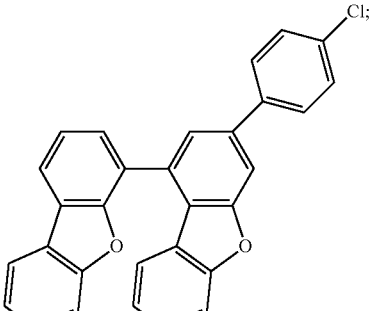
Intermediate A17-L
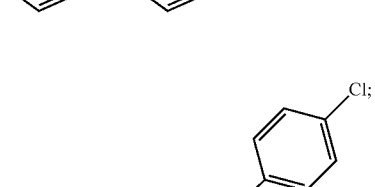
Intermediate A18-L
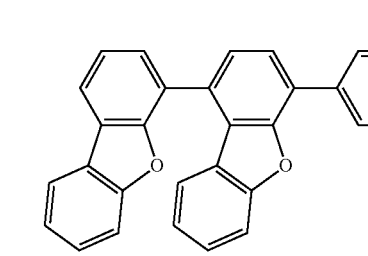
Intermediate A19-L
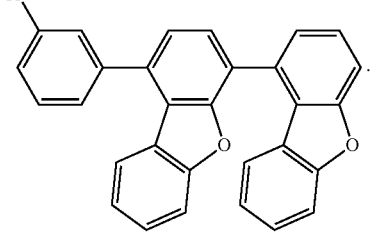

Synthesis of Novel Compounds

Each of the foresaid Intermediates, e.g., Intermediates An and An-L could be reacted with various reactants to synthesize various claimed novel compounds. The general synthesis pathway of the claimed novel compound was summarized in Scheme I. In the following Scheme I, "Reactant An" may be any one of Reactants A1 to A10 as listed in Table 5, and "Intermediate A" may be any one of the foresaid Intermediates An and An-L or the like. The compounds were each synthesized by the following steps.

Scheme I

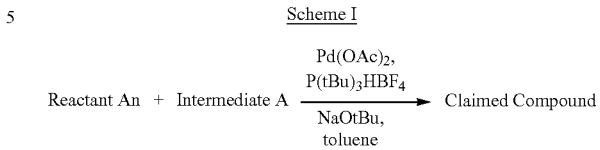

TABLE 5

| | chemical structure and CAS No. of Reactants A1 to A10. | |
| --- | --- | --- |
| Reactant No. | Reactant A1 | Reactant A2 |
| Chemical Structure | (structure) | (structure) |
| CAS No. | [102113-98-4] | [897671-81-7] |
| Reactant No. | Reactant A3 | Reactant A4 |
| Chemical Structure | (structure) | (structure) |
| CAS No. | [122-39-4] | [620-93-9] |
| Reactant No. | Reactant A5 | Reactant A6 |
| Chemical Structure | (structure) | (structure) |
| CAS No. | [55389-78-8] | [90-30-2] |
| Reactant No. | Reactant A7 | Reactant A8 |
| Chemical Structure | (structure) | (structure) |
| CAS No. | [35887-50-4] | [897671-69-1] |

TABLE 5-continued chemical structure and CAS No. of Reactants A1 to A10.

| Reactant No. | Reactant A9 | Reactant A10 |
|---|---|---|
| Chemical Structure | | |
| CAS No. | [1198395-24-2] | [29875-73-8] |

Scheme I: Synthesis of Compounds 1 to 9

In Scheme I, a mixture of Intermediate A (1.0 eq), Reactant An (1.05 eq), Pd(OAc)$_2$ (0.005 eq), tri-tert-butylphosphonium tetrafluoroborate [P(t-Bu)$_3$HBF4] (0.02 eq), sodium tert-butoxide (NaOtBu) (1.5 eq) was in toluene (40 mL). Subsequently, the reaction mixture was heated at 90° C. for 12 hours. After the completion of the reaction, the reaction mixture was cooled to room temperature, and the crude product was extracted and collected by the organic layer. The organic layer was dried over MgSO$_4$, separated by filtration and concentrated to dryness. A resulting residue was purified by silica gel column chromatography to obtain a white solid product as the claimed novel compound.

Intermediate A and Reactant An adopted to synthesize Compounds 1 to 9 were listed in Table 6.

Figure 2:
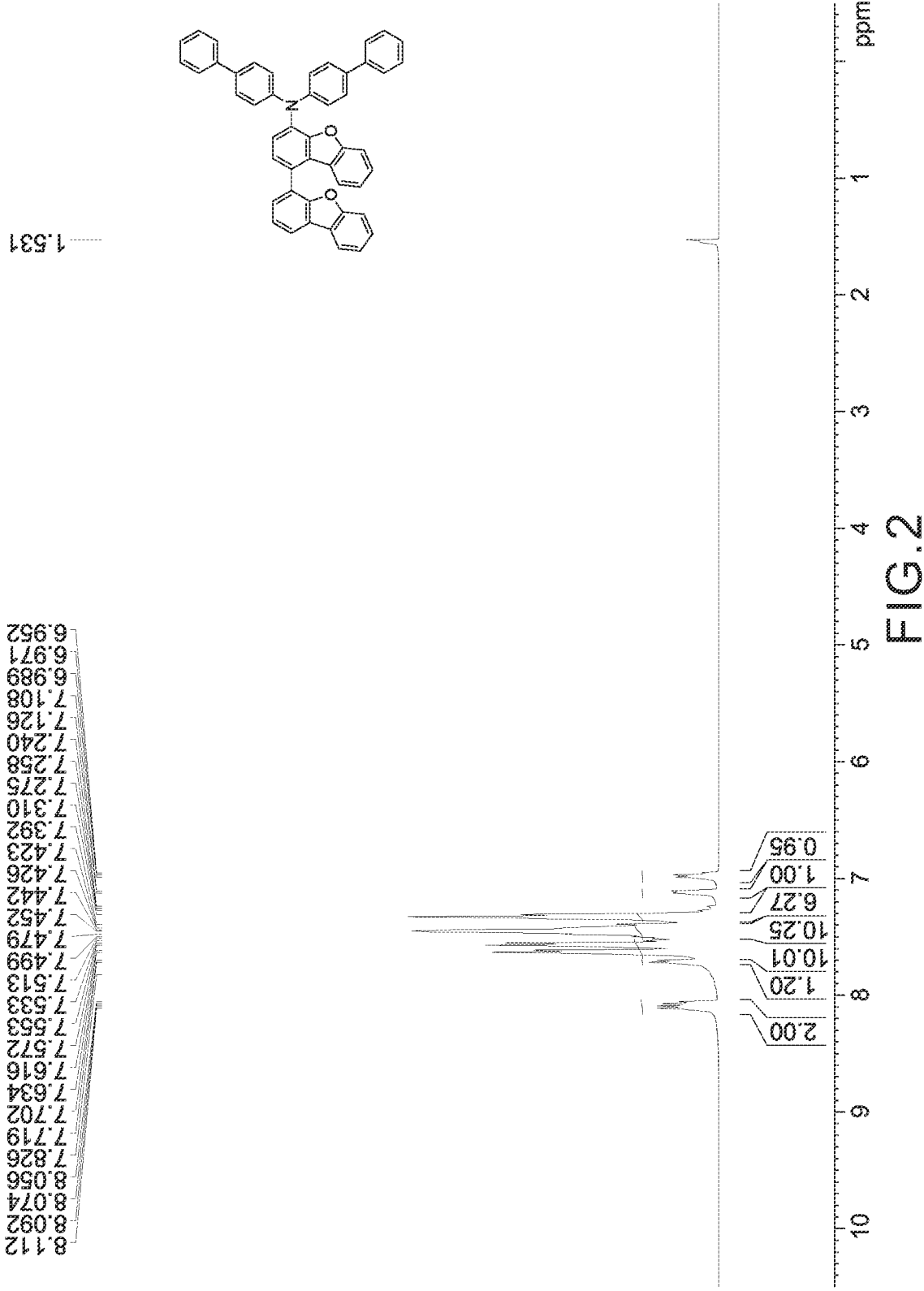
FIGS. 2 to 10 are respectively $^1$H nuclear magnetic resonance (NMR) spectra of Compounds 1 to 9.
Figure 3:
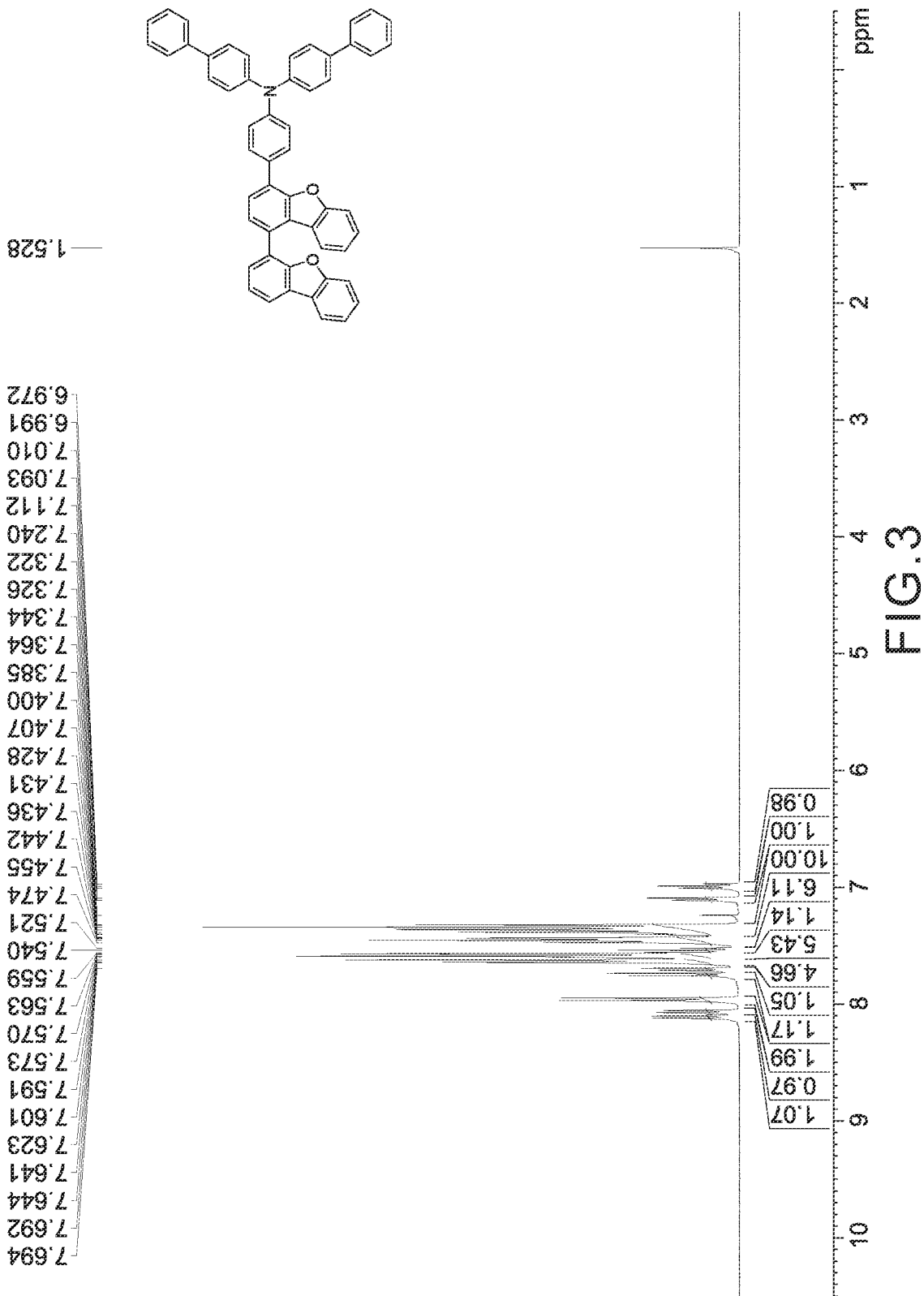
Figure 4:
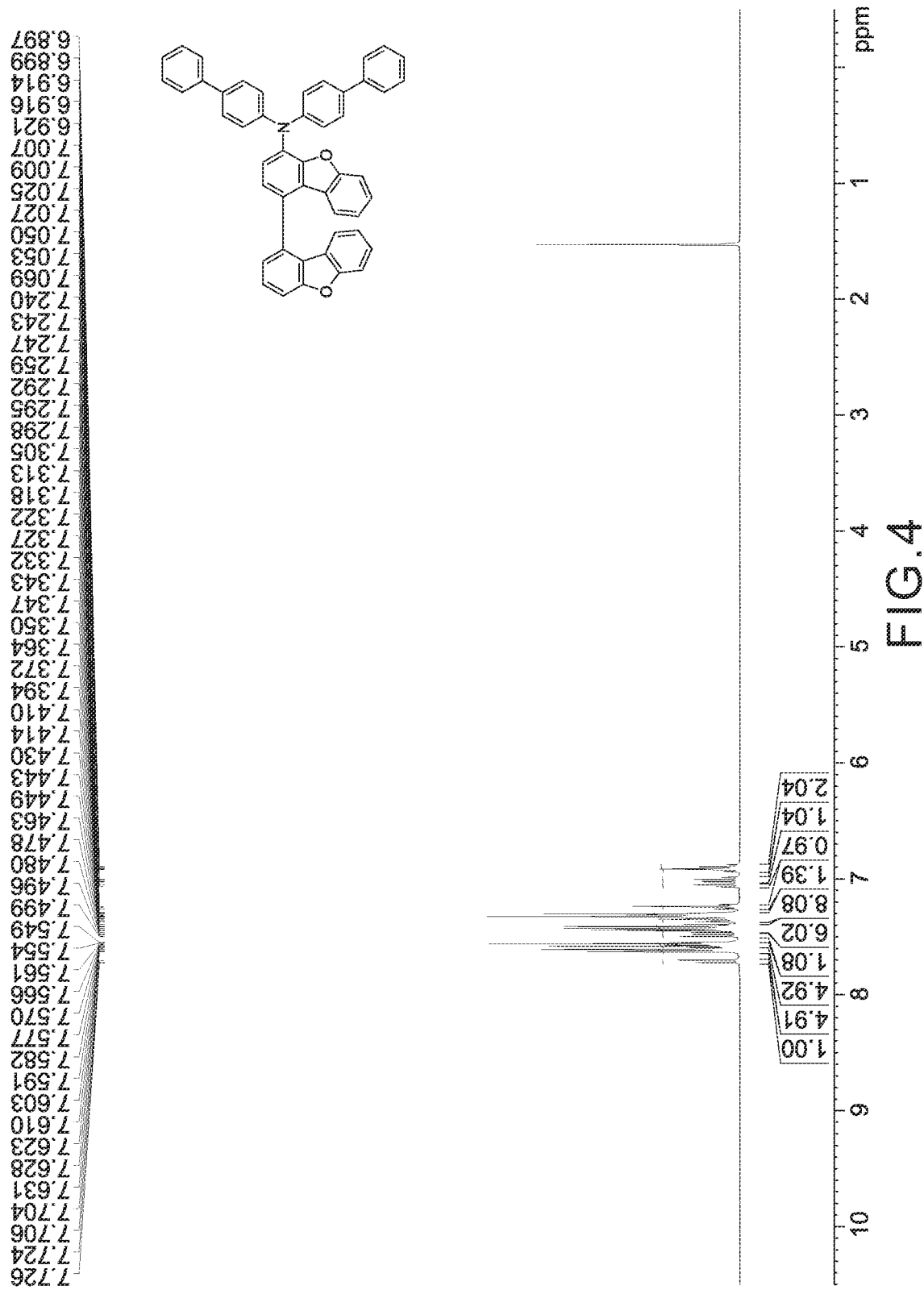
Figure 5:
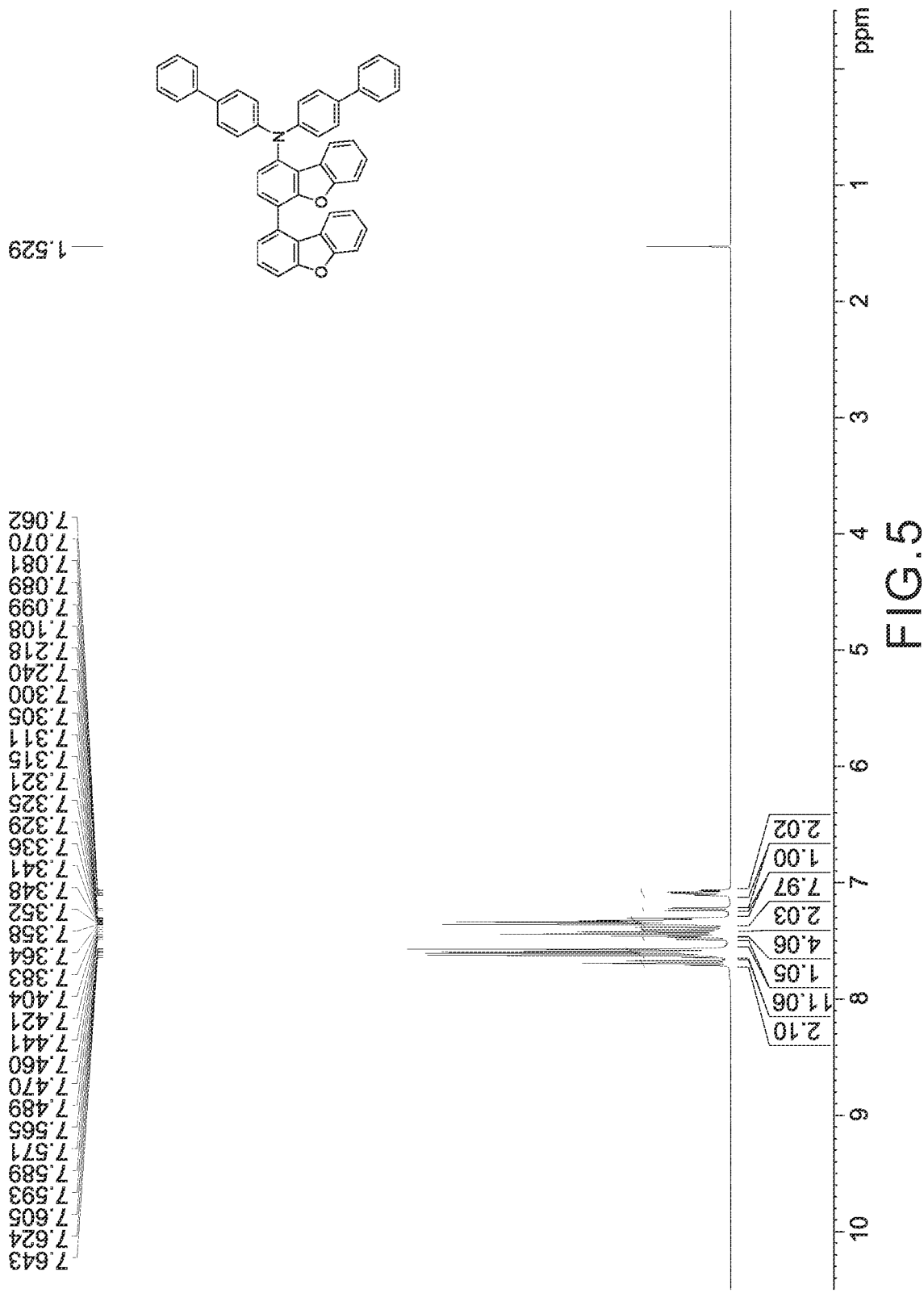
Figure 6:
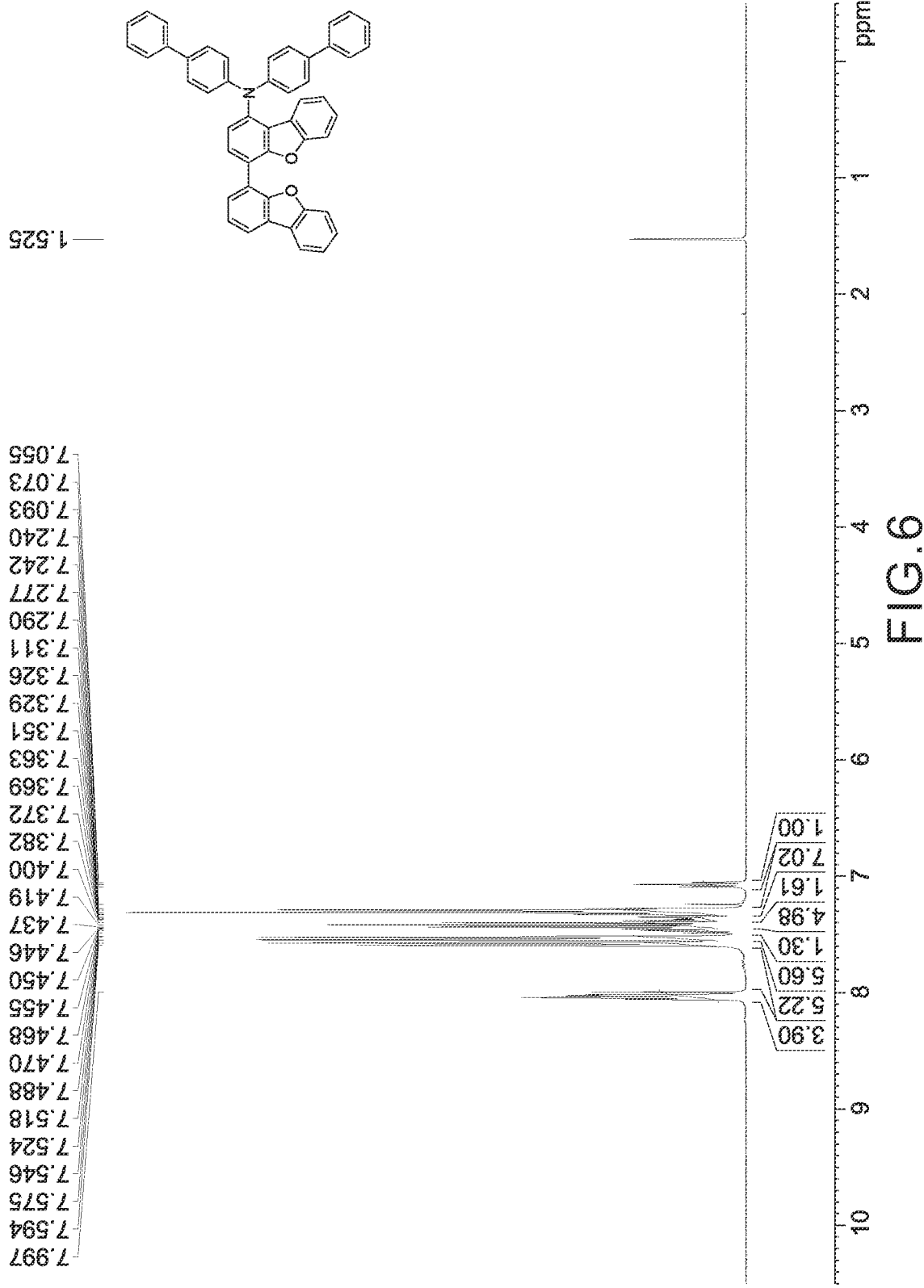
Figure 7:
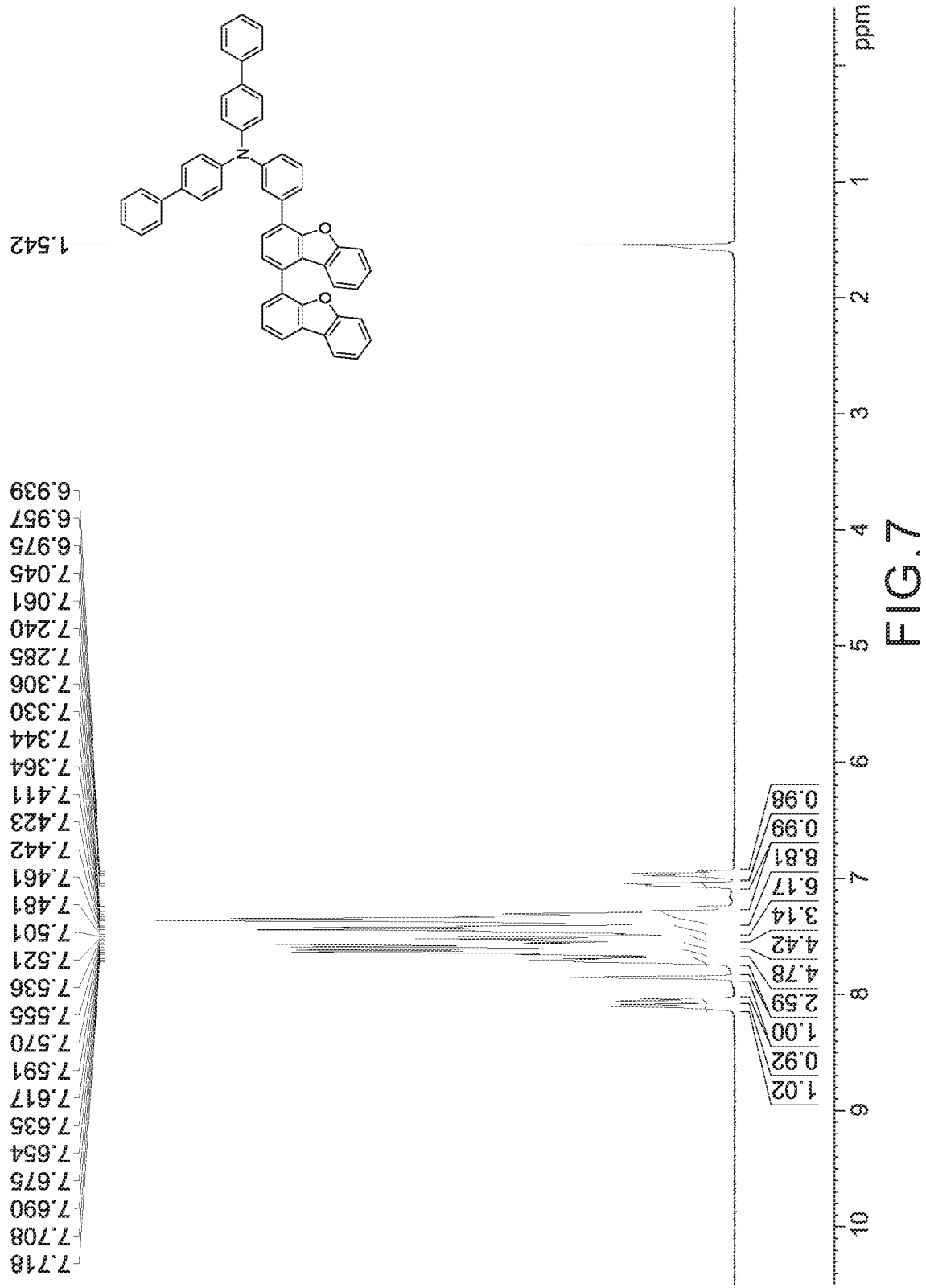
Figure 8:
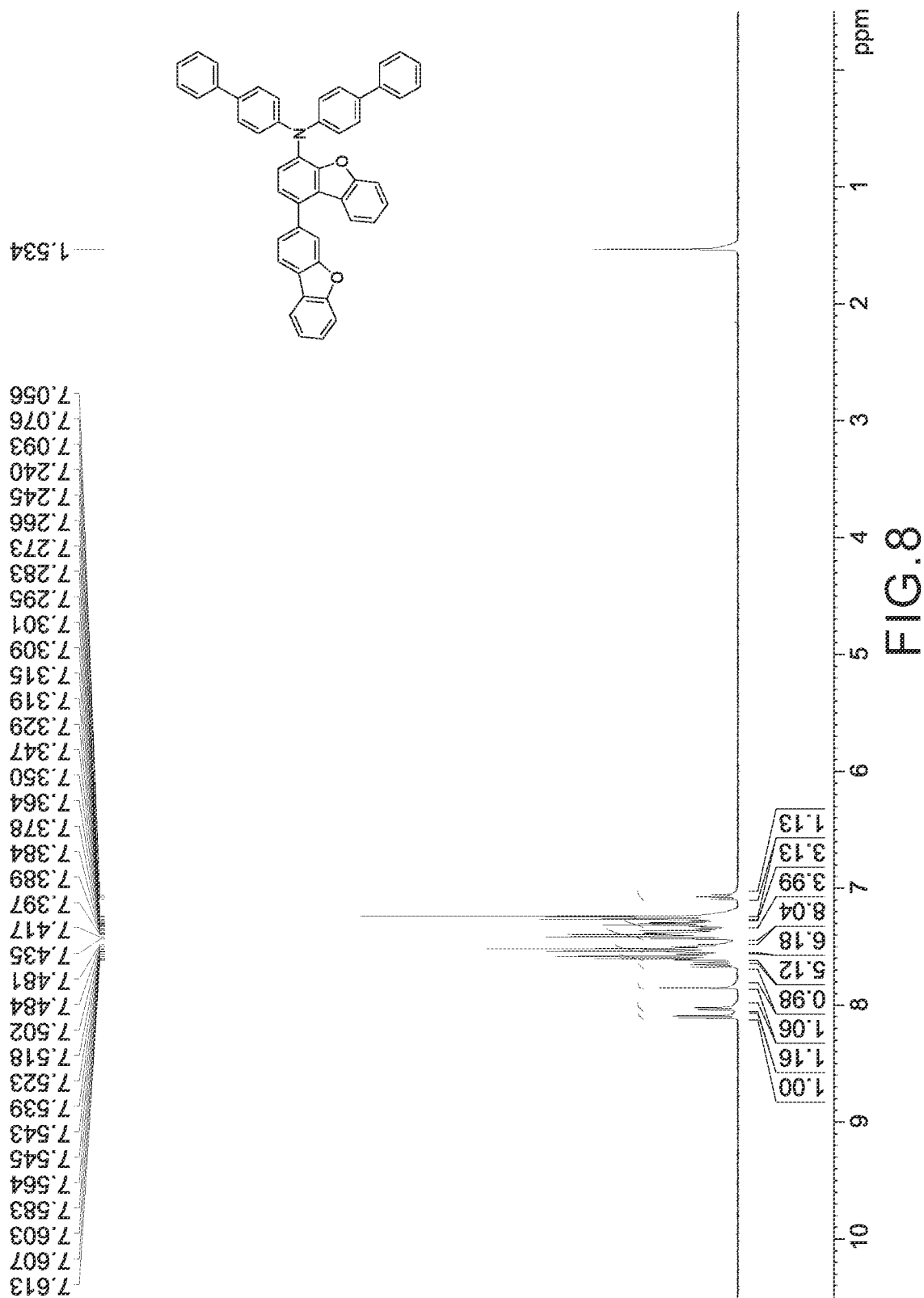
Figure 9:
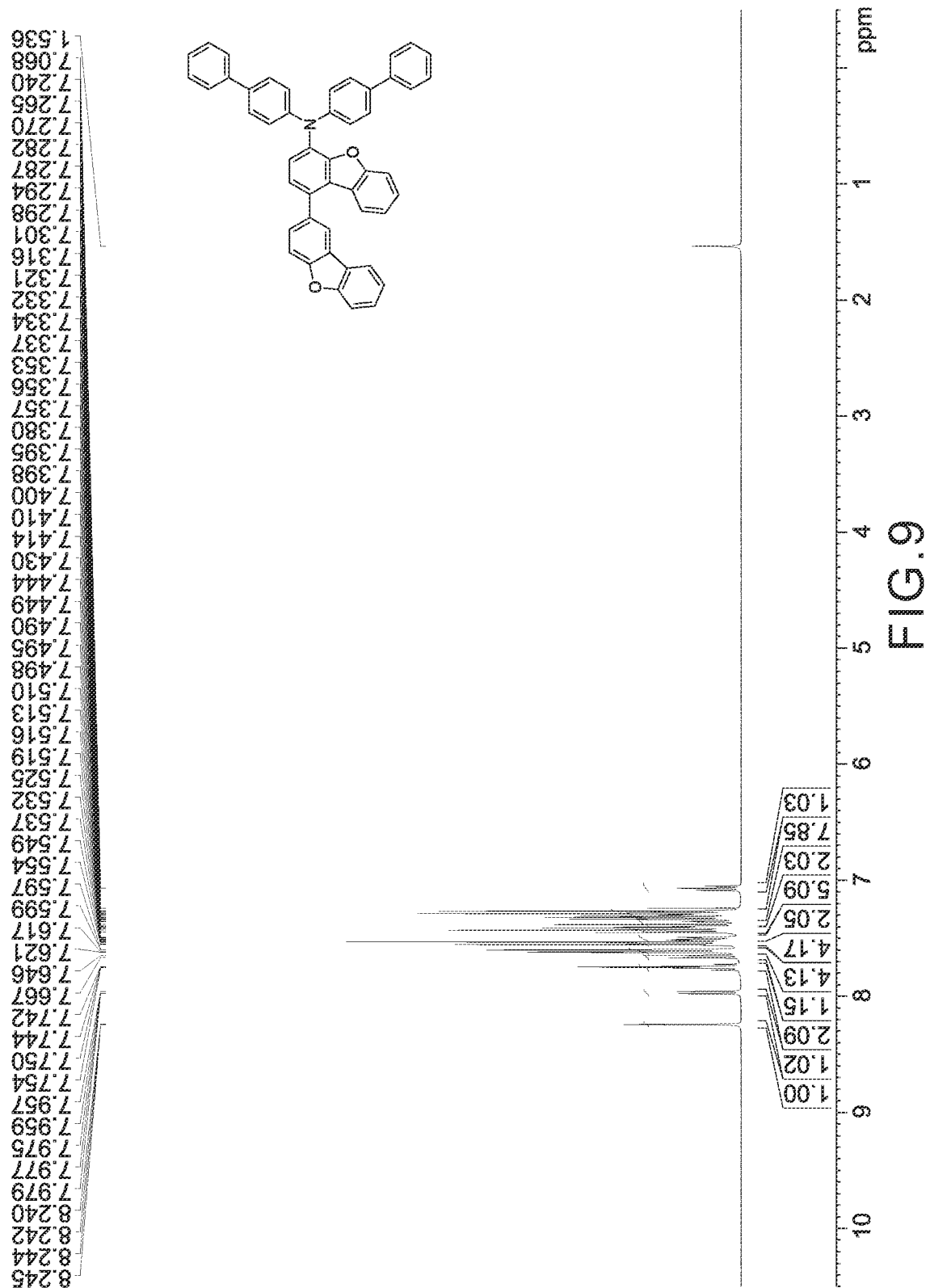
Figure 10:
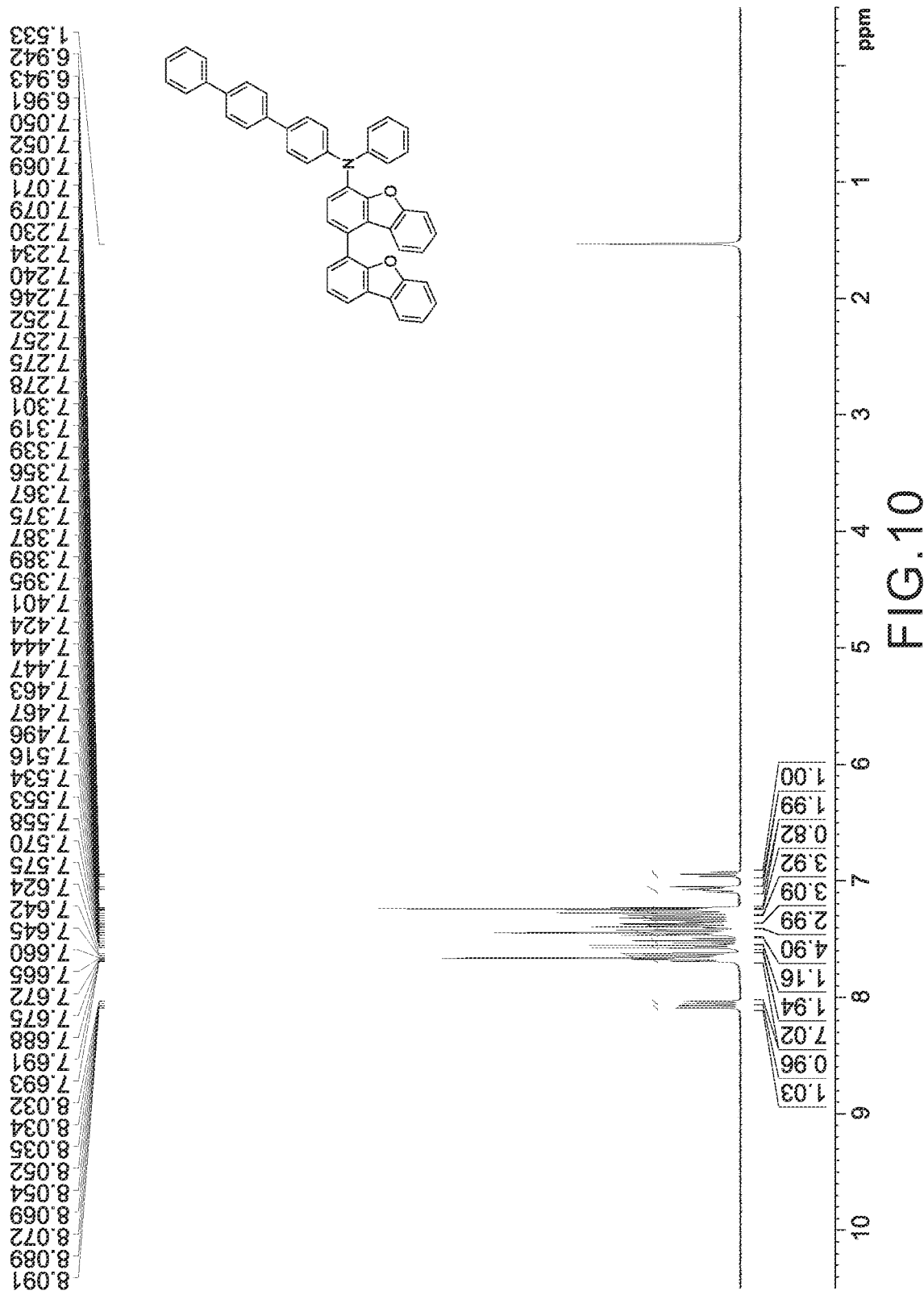

Compounds 1 to 9 were identified by H$^1$—NMR and FD-MS, and the chemical structure, yield, formula and mass of each of Compounds 1 to 9 were also listed in Table 6. According to FIGS. 2 to 10 and the results of H$^1$-NMR, the chemical structures of Compounds 1 to 9 were identified as follows.

TABLE 6 reactants and intermediates adopted to prepare Compounds 1 to 9 and their yields, formulae, and FD-MS data.

| | | Claimed Compound | | |
|---|---|---|---|---|
| Intermediate An No. | Reactant An No. | Chemical Structure of Claimed Compound | Yield (%) | Formula/ Mass (M$^+$) |
| A1 | A1 | 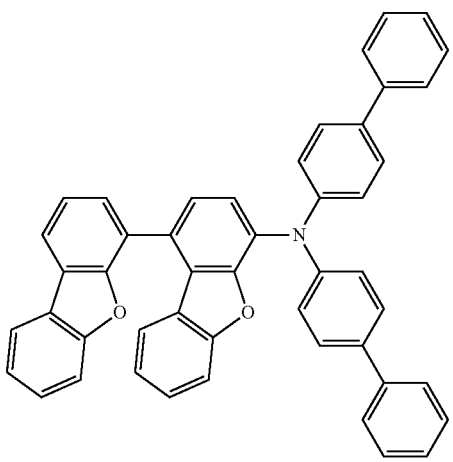 | 93.0 | C$_{48}$H$_{31}$NO$_2$/ 653.77 |

Compound 1

TABLE 6-continued
reactants and intermediates adopted to prepare Compounds 1 to 9 and
their yields, formulae, and FD-MS data.
| Intermediate An No. | Reactant An No. | Chemical Structure of Claimed Compound | Yield (%) | Formula/ Mass (M+) |
|---|---|---|---|---|
| A1-L | A1 | 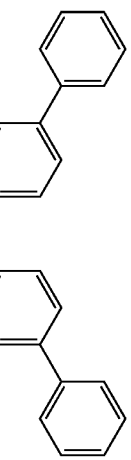<br>Compound 2 | 87.4 | $C_{54}H_{35}NO_2$/ 729.86 |
| A2 | A1 | 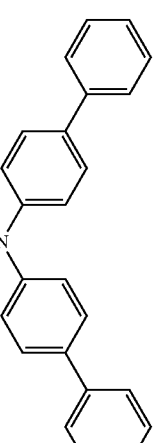<br>Compound 3 | 92.1 | $C_{48}H_{31}NO_2$/ 653.77 |
| A8 | A1 | 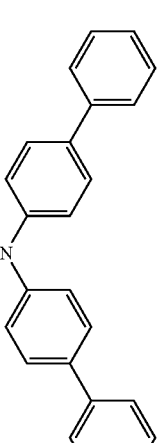<br>Compound 4 | 92.7 | $C_{48}H_{31}NO_2$/ 653.77 |

TABLE 6-continued
reactants and intermediates adopted to prepare Compounds 1 to 9 and
their yields, formulae, and FD-MS data.
| Intermediate An No. | Reactant An No. | Chemical Structure of Claimed Compound | Yield (%) | Formula/ Mass (M+) |
|---|---|---|---|---|
| A7 | A1 | 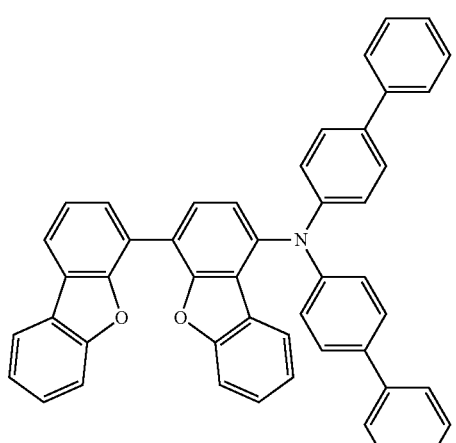  Compound 5 | 92.7 | $C_{48}H_{31}NO_2$/ 653.77 |
| A18-L | A1 | 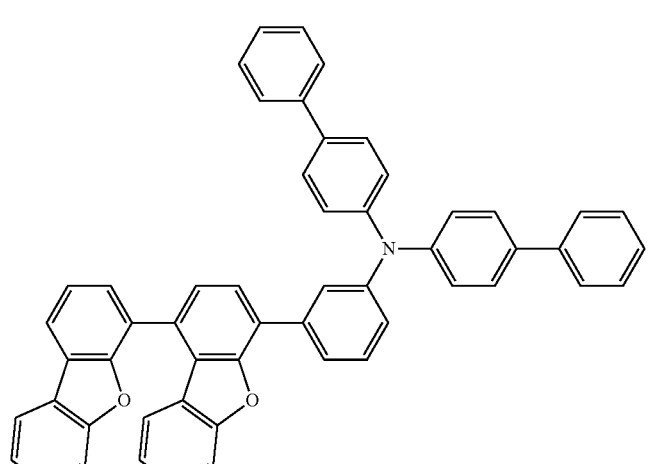  Compound 6 | 89.4 | $C_{54}H_{35}NO_2$/ 729.86 |

TABLE 6-continued
reactants and intermediates adopted to prepare Compounds 1 to 9 and their yields, formulae, and FD-MS data.
| Intermediate An No. | Reactant An No. | Claimed Compound Chemical Structure of Claimed Compound | Yield (%) | Formula/ Mass (M+) |
|---|---|---|---|---|
| A4 | A1 | Compound 7 | 91.7 | $C_{48}H_{31}NO_2$/ 653.77 |
| A3 | A1 | Compound 8 | 88.4 | $C_{48}H_{31}NO_2$/ 653.77 |
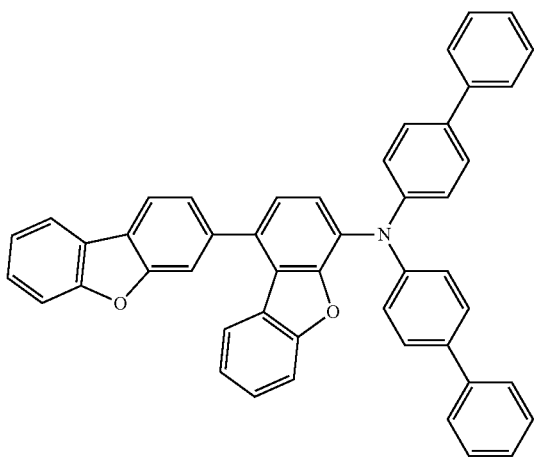
Compound 7
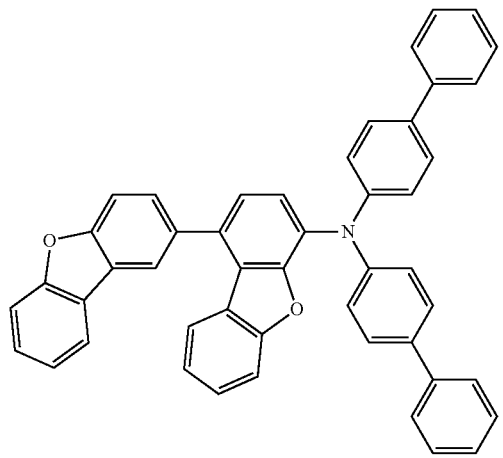
Compound 8

TABLE 6-continued reactants and intermediates adopted to prepare Compounds 1 to 9 and
their yields, formulae, and FD-MS data.

| Intermediate An No. | Reactant An No. | Chemical Structure of Claimed Compound | Yield (%) | Formula/ Mass (M+) |
|---|---|---|---|---|
| A1 | A2 | 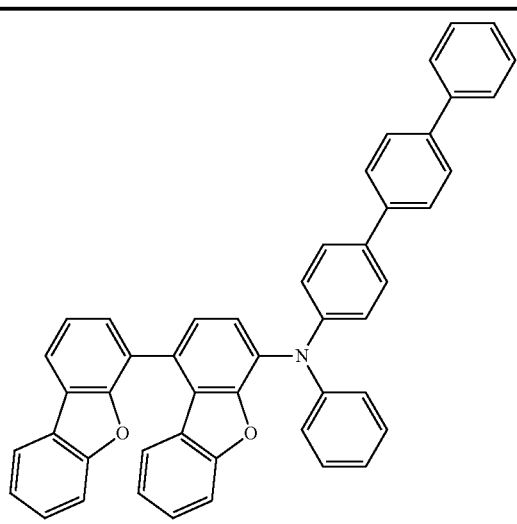<br>Compound 9 | 90.0 | $C_{48}H_{31}NO_2$/ 653.77 |

Modifications of Compounds 1 to 9

In addition to Compounds 1 to 9, one person skilled in the art can react any Intermediate A, i.e., the foresaid Intermediate An or An-L, with any Reactant An through a reaction mechanism similar to Scheme I to synthesize other desired claimed novel compounds.

Preparation of OLED devices

A glass substrate coated with an ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 29 and Comparative Examples 1 to 10. The vacuum degree during the deposition was maintained at $1 \times 10^{-6}$ to $3 \times 10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and HIL-2; HI-D was a material for forming HIL-1; HI-A was a material for forming HIL-1, HIL-2, and HTL-1; commercial HI (m-MTDATA) was a material for forming HIL-2; HT-A and HT-B were respectively materials for forming HTL-1 and HTL-2; novel compounds of the present invention were materials for forming HTL-1, HTL-2, or HIL-2, respectively; commercial HTs (NPB and HT-C) were materials for forming HTL-1 and HTL-2, respectively; Liq was a material for forming ETL and EIL. RH/GH/BH were each a host material for forming REL/GEL/BEL, and RD/GD/BD were each a dopant for forming REL/GEL/BEL. The main difference of the OLEDs between the Examples and Comparative Examples was that the HTL-1, HTL-2, or HIL-2 of OLED in the following comparative examples was made of its respective commercial material but the HTL-1, HTL-2, or HIL-2 of OLED in the following examples was made of the novel compounds of the present invention listed in Table 6. The detailed chemical structures of foresaid commercial materials were listed in Table 7.

TABLE 7 chemical structures of commercial materials for OLED devices.

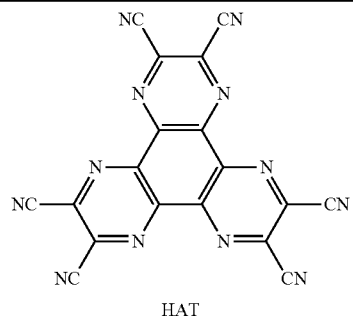

HAT

TABLE 7-continued
chemical structures of commercial materials for OLED devices.
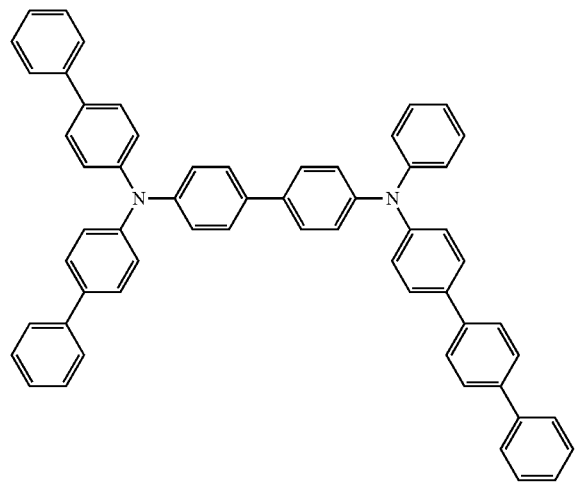
HI-A
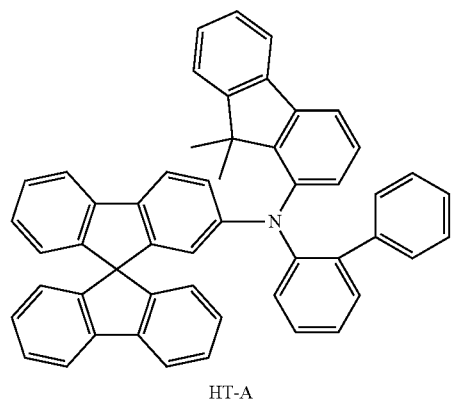
HT-A
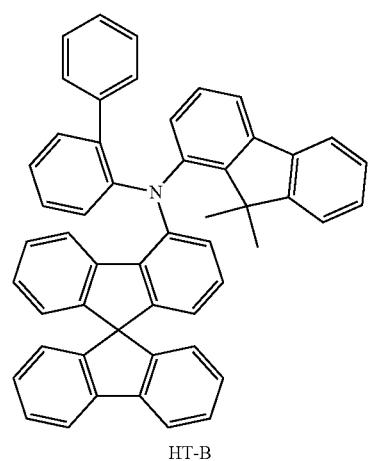
HT-B
TABLE 7-continued
chemical structures of commercial materials for OLED devices.
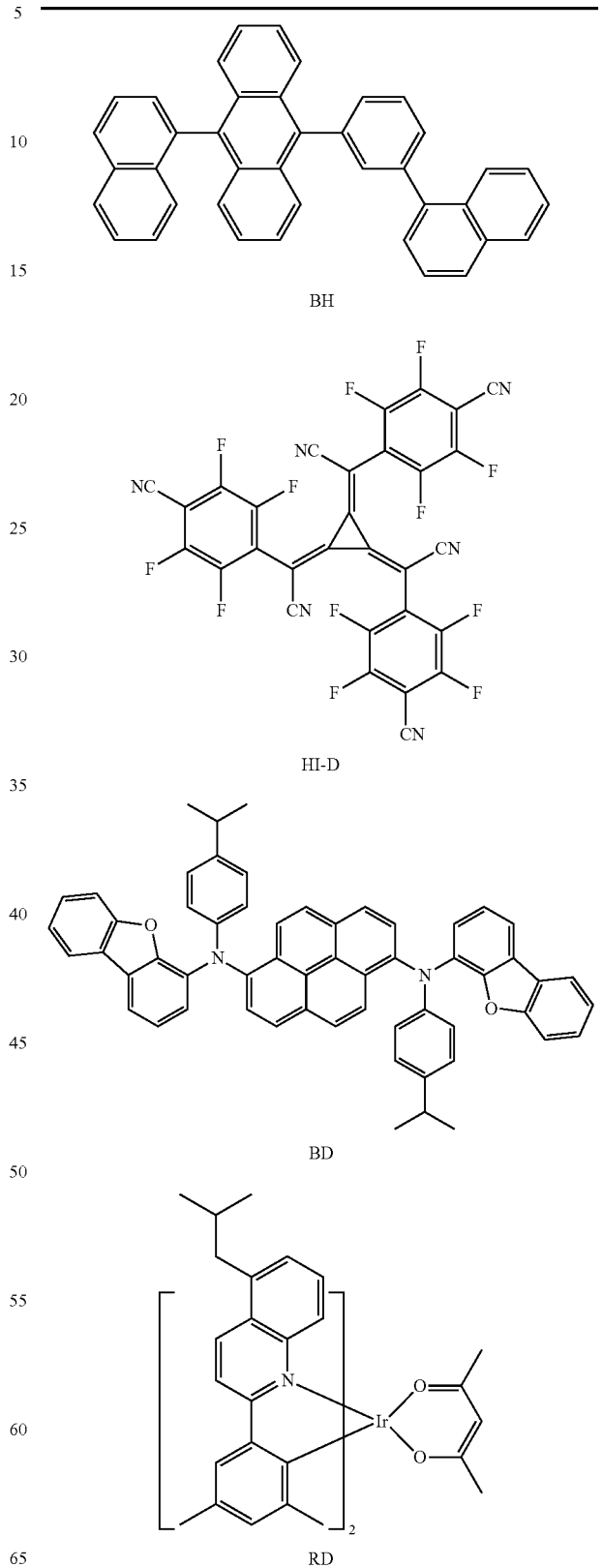
BH
HI-D
BD
RD TABLE 7-continued
chemical structures of commercial materials for OLED devices.
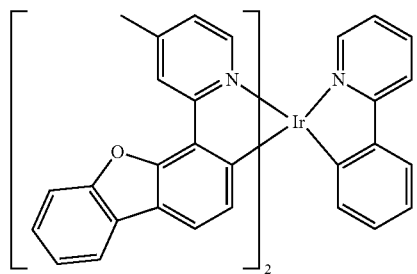
GD
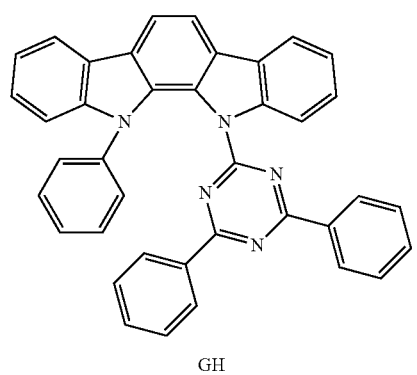 [SMILES: c1ccc(-c2nc(-c3ccccc3)nc(-n3c4ccccc4c4ccc5c6ccccc6n(-c6ccccc6)c5c43)n2)cc1]
GH
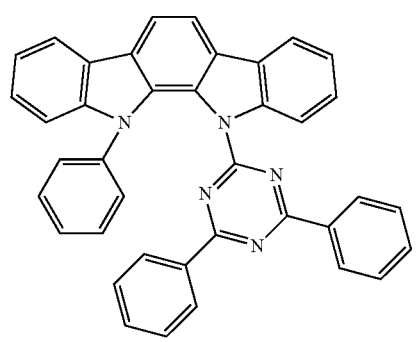
RH
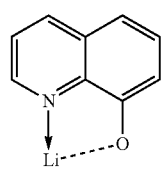
Liq
TABLE 7-continued
chemical structures of commercial materials for OLED devices.
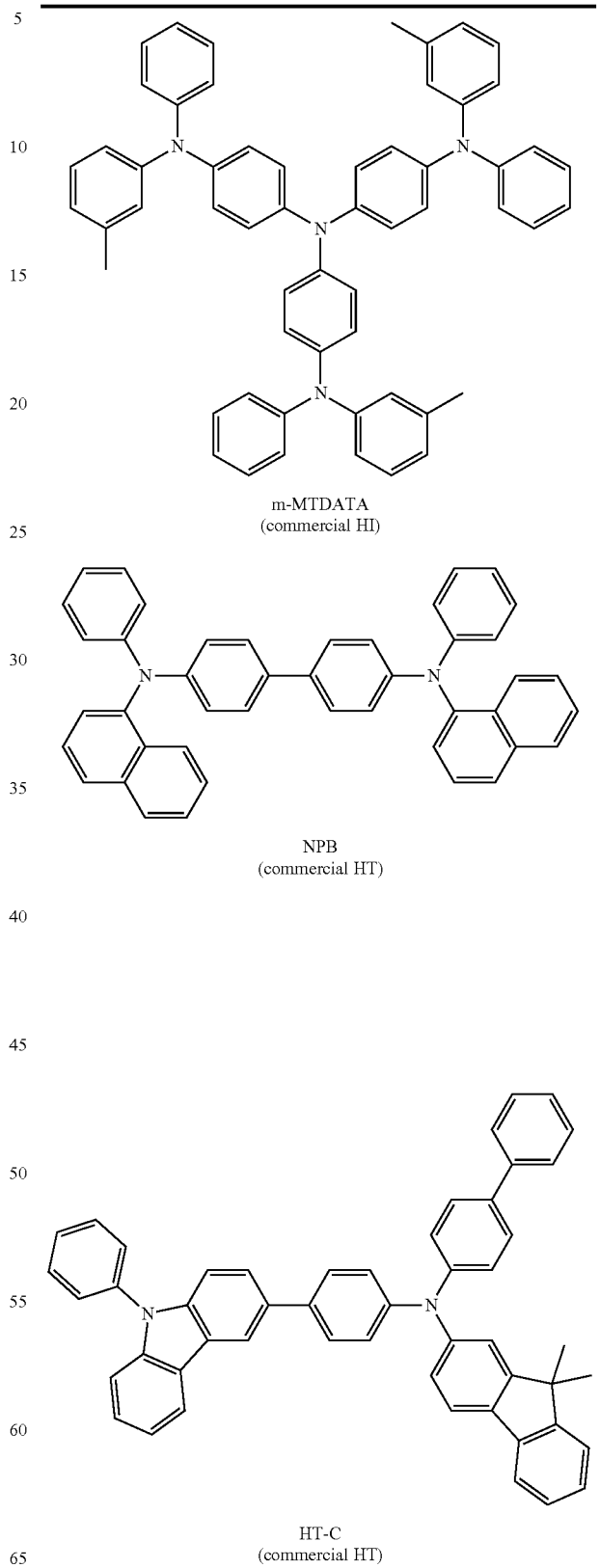
m-MTDATA
(commercial HI)
NPB
(commercial HT)
HT-C
(commercial HT)

TABLE 7-continued chemical structures of commercial materials for OLED devices.

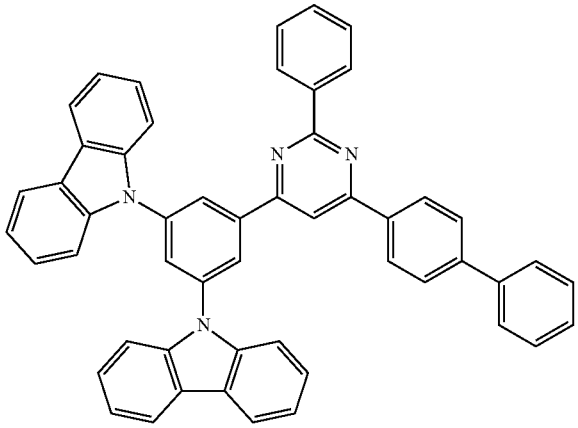

ET

Preparation of blue OLED devices

To prepare the blue OLED devices, multiple organic layers were respectively deposited on the ITO substrate according to the sequence as listed in Table 8 to prepare a first blue OLED device and a second blue OLED device. The materials and the thicknesses of the organic layers in the blue OLED devices were also listed in Table 8. The difference between the first and the second blue OLED devices is the materials of HIL-1 and HIL-2 as listed in Table 8.

TABLE 8 coating sequence, materials and thickness of the layers in the blue OLED devices.

| Coating Sequence | Layer | Material First blue OLED device | Material Second blue OLED device | Thickness |
|---|---|---|---|---|
| 1 | HIL-1 | HAT | HI-A doped with 3.0 wt % of HI-D | 100 Å |
| 2 | HIL-2 | HI doped with 5.0 wt % of HAT | HI | 750 Å |
| 3 | HTL-1 | HT-1 | HT-1 | 100 Å |
| 4 | HTL-2 | HT-2 | HT-2 | 100 Å |
| 5 | BEL | BH doped with 3.5 wt % of BD | BH doped with 3.5 wt % of BD | 300 Å |
| 6 | ETL | ET doped with 35.0 wt % of Liq | ET doped with 35.0 wt % of Liq | 350 Å |
| 7 | EIL | Liq | Liq | 15 Å |
| 8 | Cthd | Al | Al | 1500 Å |

Preparation of Green OLED Devices

To prepare the green OLED device, multiple organic layers were respectively deposited on the ITO substrate according to the sequence as listed in Table 9, and the materials and the thicknesses of the organic layers in green OLED devices were also listed in Table 9.

TABLE 9 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI doped with 5.0 wt % of HAT | 1300 Å |
| 3 | HTL-1 | HT-1 | 100 Å |
| 4 | HTL-2 | HT-2 | 100 Å |
| 5 | GEL | GH doped with 10.0 wt % of GD | 300 Å |
| 6 | ETL | ET doped with 35.0 wt % of Liq | 350 Å |
| 7 | EIL | Liq | 15 Å |
| 8 | Cthd | Al | 1500 Å |

Preparation of Red OLED Devices

To prepare the red OLED device, multiple organic layers were respectively deposited on the ITO substrate according to the sequence as listed in Table 10, and the materials and the thicknesses of the organic layers in red OLED devices were also listed in Table 10.

TABLE 10 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI doped with 5.0 wt % of HAT | 2100 Å |
| 3 | HTL-1 | HT-1 | 100 Å |
| 4 | HTL-2 | HT-2 | 100 Å |
| 5 | REL | RH doped with 3.5 wt % of RD | 300 Å |
| 6 | ETL | ET doped with 35.0 wt % of Liq | 350 Å |
| 7 | EIL | Liq | 15 Å |
| 8 | Cthd | Al | 1500 Å |

Performance of Blue OLED Devices

To evaluate the performance of OLED devices, the blue OLED devices were measured by PR650 as photometer and Keithley 2400 as power supply. Color coordinates (x,y) were determined according to the CIE chromaticity scale (Commission Internationale de L'Eclairage, 1931). For the blue OLED devices, the data were collected at 1000 nits. The results were shown in Tables 11 and 12.

To determine whether the novel compound of the present invention is suitable as a hole transport material of HTL-1 and exhibits an improved performance in blue OLEDs, the difference between Examples 1 to 5 and Comparative Example 1 was only the material of HT-1. The materials of HT-1, and data of CIE, current efficiency, luminous efficacy, and external quantum efficiency of the first blue OLEDs of Examples 1 to 5 and Comparative Example 1 were listed in Table 11. In the first blue OLEDs of Examples 1 to 5 and Comparative Example 1, HI of HIL-2 was HI-A as shown in Table 7, and HT-2 of HTL-2 was HT-B as shown in Table 7.

TABLE 11 materials of HT-1, CIEs, current efficiencies, luminous efficacy, and external quantum efficiency of OLED devices of Examples 1 to 5 and Comparative Example 1.

| Example No. | Material of HT-1 | CIE(x, y) | Current Efficiency (cd/A) | Luminous Efficacy (lm/W) | External Quantum Efficiency (%) |
|---|---|---|---|---|---|
| E1 | Compound 1 | (0.129, 0.155) | 10.70 | 7.39 | 7.03 |
| E2 | Compound 2 | (0.130, 0.148) | 9.59 | 6.28 | 6.84 |
| E3 | Compound 7 | (0.128, 0.155) | 10.30 | 7.44 | 6.26 |

TABLE 11-continued materials of HT-1, CIEs, current efficiencies, luminous efficacy, and external quantum efficiency of OLED devices of Examples 1 to 5 and Comparative Example 1.

| Example No. | Material of HT-1 | CIE(x, y) | Current Efficiency (cd/A) | Luminous Efficacy (lm/W) | External Quantum Efficiency (%) |
|---|---|---|---|---|---|
| E4 | Compound 8 | (0.129, 0.148) | 9.89 | 7.15 | 7.10 |
| E5 | Compound 9 | (0.128, 0.153) | 9.79 | 7.20 | 6.79 |
| C1 | NPB | (0.129, 0.160) | 9.50 | 6.25 | 6.21 |

Further, to determine whether the novel compound of the present invention is suitable as a hole transport material of HTL-2 and exhibits an improved performance in blue OLEDs, the difference between the first blue OLEDs of Examples 6 and 7 and Comparative Example 2 and the difference between the second blue OLEDs of Examples 8 to 13 and Comparative Example 3 were the material of HT-2. The materials of HT-2, and data of CIE, current efficiency, luminous efficacy, and external quantum efficiency of Examples 6 to 13 and Comparative Example 2 to 3 were listed in Table 12. In the first and second blue OLEDs of Examples 6 to 13 and Comparative Examples 2 and 3, HI of HIL-2 was HI-A as shown in Table 7, and HT-1 of HTL-1 was HT-A as shown in Table 7.

TABLE 12 materials of HT-2, CIEs, current efficiencies, luminous efficacy, and external quantum efficiency of OLED devices of Examples 6 to 13 and Comparative Examples 2 to 3.

| Example No. | Material of HT-2 | CIE(x, y) | Current Efficiency (cd/A) | Luminous Efficacy (lm/W) | External Quantum Efficiency (%) |
|---|---|---|---|---|---|
| E6 | Compound 3 | (0.129, 0.153) | 10.30 | 6.79 | 6.96 |
| E7 | Compound 5 | (0.129, 0.155) | 10.80 | 7.76 | 6.80 |
| C2 | HT-C | (0.129, 0.159) | 9.10 | 6.36 | 6.50 |
| E8 | Compound 1 | (0.130, 0.149) | 9.22 | 6.99 | 6.27 |
| E9 | Compound 2 | (0.128, 0.166) | 10.30 | 8.03 | 6.71 |
| E10 | Compound 6 | (0.129, 0.149) | 9.93 | 7.59 | 6.53 |
| E11 | Compound 7 | (0.129, 0.164) | 9.59 | 6.98 | 6.77 |
| E12 | Compound 8 | (0.129, 0.159) | 10.90 | 8.24 | 6.39 |
| E13 | Compound 9 | (0.129, 0.156) | 9.93 | 7.17 | 6.09 |
| C3 | HT-C | (0.128, 0.166) | 8.77 | 6.70 | 5.64 |

Based on the results in Tables 11 and 12, in comparison with the commercial hole transport materials for the first or second hole transport layer, adopting Compounds 1 to 3, 5 to 9 as the hole transport material for the first or second hole transport layer can improve the current efficiency, luminous efficacy, external quantum efficiency of the blue OLEDs.

Performance of Green OLED Devices

To evaluate the performance of OLED devices, the green OLED devices were measured by PR650 as photometer and Keithley 2400 as power supply. Color coordinates (x,y) were determined according to the CIE chromaticity scale (Commission Internationale de L'Eclairage, 1931). For the green OLED devices, the data were collected at 3000 nits. The results were shown in Tables 13 and 14.

To determine whether the novel compound of the present invention is suitable as a hole transport material of HTL-1 and exhibits an improved performance in green OLEDs, the difference between Examples 14 to 18 and Comparative Example 4 was only the material of HT-1. The materials of HT-1, and data of CIE, current efficiency, luminous efficacy, and external quantum efficiency of the green OLEDs of Examples 14 to 18 and Comparative Example 4 were listed in Table 13. In the green OLEDs of Examples 14 to 18 and Comparative Example 4, HI of HIL-2 was HI-A as shown in Table 7, and HT-2 of HTL-2 was HT-B as shown in Table 7.

TABLE 13 materials of HT-1, CIEs, current efficiencies, luminous efficacy, and external quantum efficiency of OLED devices of Examples 14 to 18 and Comparative Example 4.

| Example No. | Material of HT-1 | CIE(x, y) | Current Efficiency (cd/A) | Luminous Efficacy (lm/W) | External Quantum Efficiency (%) |
|---|---|---|---|---|---|
| E14 | Compound 1 | (0.317, 0.637) | 70.80 | 60.07 | 15.96 |
| E15 | Compound 2 | (0.313, 0.639) | 73.50 | 67.70 | 16.57 |
| E16 | Compound 7 | (0.320, 0.637) | 74.50 | 63.40 | 18.05 |
| E17 | Compound 8 | (0.316, 0.638) | 78.60 | 68.20 | 18.08 |
| E18 | Compound 9 | (0.316, 0.639) | 76.20 | 76.20 | 17.52 |
| C4 | NPB | (0.317, 0.637) | 70.10 | 59.84 | 15.88 |

Similarly, to determine whether the novel compound of the present invention is suitable as a hole transport material of HTL-2 and exhibits an improved performance in green OLEDs, the difference between the green OLEDs of Examples 19 and 20 and Comparative Example 5 was only the material of HT-2. The materials of HT-2, and data of CIE, current efficiency, luminous efficacy, and external quantum efficiency of the green OLEDs of Examples 19 and 20 and Comparative Example 5 were listed in Table 14. In the green OLEDs of Examples 19 and 20 and Comparative Example 5, HI of HIL-2 was HI-A as shown in Table 7, and HT-1 of HTL-1 was HT-A as shown in Table 7.

TABLE 14 materials of HT-2, CIEs, current efficiencies, luminous efficacy, and external quantum efficiency of OLED devices of Examples 19 to 20 and Comparative Example 5.

| Example No. | Material of HT-2 | CIE(x, y) | Current Efficiency (cd/A) | Luminous Efficacy (lm/W) | External Quantum Efficiency (%) |
|---|---|---|---|---|---|
| E19 | Compound 3 | (0.314, 0.638) | 69.70 | 48.30 | 17.15 |
| E20 | Compound 5 | (0.320, 0.635) | 71.00 | 47.60 | 17.20 |
| C5 | HT-C | (0.312, 0.639) | 38.60 | 31.70 | 8.57 |

Based on the results in Tables 13 and 14, in comparison with the commercial hole transport materials for the first or second hole transport layer, adopting Compounds 1 to 3, 5, 7 to 9 as the hole transport material for the first or second hole transport layer can improve the current efficiency, luminous efficacy, external quantum efficiency of the green OLEDs.

Performance of Red OLED Devices

To evaluate the performance of OLED devices, the red OLED devices were measured by PR650 as photometer and Keithley 2400 as power supply. Color coordinates (x,y) were determined according to the CIE chromaticity scale (Commission Internationale de L'Eclairage, 1931). For the red OLED devices, the data were collected at 1000 nits. The results were shown in Tables 15 and 16.

To determine whether the novel compound of the present invention is suitable as a hole transport material of HTL-1 and exhibits an improved performance in red OLEDs, the difference between Examples 21 and 22 and Comparative Example 6 was only the material of HT-1. The materials of HT-1, and data of CIE, current efficiency, luminous efficacy, and external quantum efficiency of red OLEDs of Examples 21 and 22 and Comparative Example 6 were listed in Table 15. In red OLEDs of Examples 21 and 22 and Comparative Example 6, HI of HIL-2 was HI-A as shown in Table 7, and HT-2 of HTL-2 was HT-B as shown in Table 7.

TABLE 15 materials of HT-1, CIEs, current efficiencies, luminous efficacy, and external quantum efficiency of OLED devices of Examples 21 to 22 and Comparative Example 6.

| Example No. | Material of HT-1 | CIE(x, y) | Current Efficiency (cd/A) | Luminous Efficacy (lm/W) | External Quantum Efficiency (%) |
|---|---|---|---|---|---|
| E21 | Compound 1 | (0.660, 0.339) | 26.50 | 22.75 | 17.98 |
| E22 | Compound 8 | (0.664, 0.334) | 26.50 | 22.59 | 17.96 |
| C6 | NPB | (0.661, 0.337) | 26.30 | 22.50 | 17.94 |

Similarly, to determine whether the novel compound of the present invention is suitable as a hole transport material of HTL-2 and exhibits an improved performance in red OLEDs, the difference between the red OLEDs of Examples 23 to 25 and Comparative Example 7 was only the material of HT-2. The materials of HT-2, and data of CIE, current efficiency, luminous efficacy, and external quantum efficiency of the red OLEDs of Examples 23 to 25 and Comparative Example 7 were listed in Table 16. In the red OLEDs of Examples 23 to 25 and Comparative Example 7, HI of HIL-2 was HI-A as shown in Table 7, and HT-1 of HTL-1 was HT-A as shown in Table 7.

TABLE 16 materials of HT-2, CIEs, current efficiencies, luminous efficacy, and external quantum efficiency of OLED devices of Examples 23 to 25 and Comparative Example 7.

| Example No. | Material of HT-2 | CIE(x, y) | Current Efficiency (cd/A) | Luminous Efficacy (lm/W) | External Quantum Efficiency (%) |
|---|---|---|---|---|---|
| E23 | Compound 3 | (0.661, 0.338) | 23.20 | 20.20 | 16.11 |
| E24 | Compound 5 | (0.659, 0.339) | 23.30 | 18.50 | 15.91 |
| E25 | Compound 6 | (0.630, 0.329) | 12.90 | 9.12 | 9.43 |
| C7 | HT-C | (0.635, 0.354) | 6.88 | 3.36 | 4.50 |

Based on the results in Tables 15 and 16, in comparison with the commercial hole transport materials for the first or second hole transport layer, adopting Compounds 1, 3, 5, 6, 8 as the hole transport material for the first or second hole transport layer can improve the current efficiency, luminous efficacy, external quantum efficiency of the red OLEDs.

Performance of OLED Devices

To evaluate the performance of OLED devices, the OLED devices were measured by PR650 as photometer and Keithley 2400 as power supply. Color coordinates (x,y) were determined according to the CIE chromaticity scale (Commission Internationale de L'Eclairage, 1931). For the blue and red OLED devices, the data were collected at 1000 nits, and for the green OLED device, the data was collected at 3000 nits. The results were shown in Table 17.

To determine whether the novel compound of the present invention is suitable as a hole injection material of HIL and exhibits an improved performance in any color OLEDs, the difference between the first blue OLEDs of Examples 26 and 27 and Comparative Example 8, the difference between the green OLEDs of Example 28 and Comparative Example 9, and the difference between the red OLEDs of Examples 29 and Comparative Example 10 were the material of HIL-2. The materials of HI of HIL-2, colors and data of CIE, current efficiency, luminous efficacy, and external quantum efficiency of said OLEDs of Examples 26 to 29 and Comparative Examples 8 to 10 were listed in Table 17. In said OLEDs, HT-1 of HTL-1 was HT-A as shown in Table 7, and HT-2 of HTL-2 was HT-B as shown in Table 7.

TABLE 17 materials of HI, colors and CIEs, current efficiencies, luminous efficacy, and external quantum efficiency of OLED devices of Examples 26 to 29 and Comparative Examples 8 to 10.

| Example No. | Material of HI | Color CIE(x, y) | Current Efficiency (cd/A) | Luminous Efficacy (lm/W) | External Quantum Efficiency (%) |
|---|---|---|---|---|---|
| E26 | Compound 1 | B(0.131, 0.145) | 9.34 | 6.46 | 6.26 |
| E27 | Compound 2 | B(0.130, 0.147) | 9.48 | 7.14 | 5.85 |
| C8 | m-MTDATA | B(0.14, 0.187) | 4.59 | 2.11 | 2.90 |
| E28 | Compound 1 | G(0.312, 0.641) | 73.60 | 66.70 | 16.17 |
| C9 | m-MTDATA | G(0.325, 0.631) | 55.50 | 41.30 | 13.60 |
| E29 | Compound 1 | R(0.654, 0.343) | 30.90 | 18.80 | 20.87 |
| C10 | m-MTDATA | R(0.656, 0.341) | 20.40 | 12.57 | 13.61 |

Based on the results in Table 17, in comparison with the commercial hole injection layer material for the second hole injection layer, adopting Compounds 1 and 2 as the hole injection material for the second hole transport layer can improve the current efficiency, luminous efficacy, external quantum efficiency of the blue, green, and red OLEDs.

It demonstrated that the novel compound of the present invention is suitable as a hole transport material or hole injection material for OLEDs of any color, and allows the OLEDs using the same to have improved current efficiency, luminous efficacy and external quantum efficiency.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by the following Formula (I'):

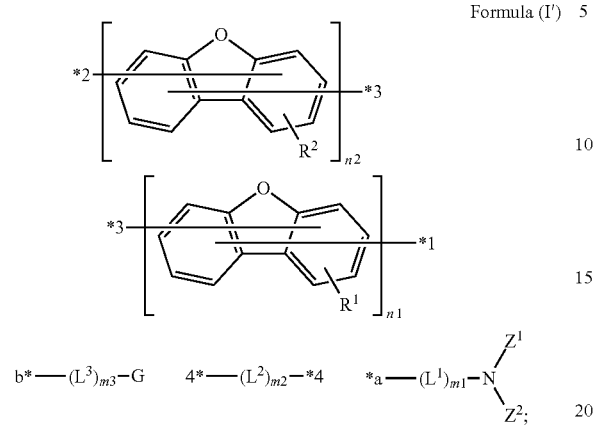

Formula (I')

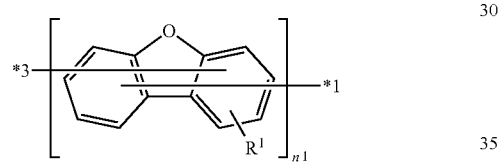

wherein n1 is an integer from 1 to 3, and n2 is an integer from 0 to 2, and the sum of n1 and n2 is 2 or 3;

wherein when n2 is an integer 1 or 2, *1 is bonded to *a, *2 is bonded to *b, and two *3s are bonded to two *4s;

wherein when n2 is an integer 0, *1 is bonded to *a, *3 of the group of

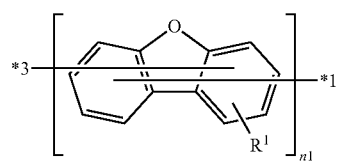

is bonded to one of *4s, and the other of *4s is bonded to *b;

m1, m2 and m3 are each independently an integer 0 or 1, and m1, m2 and m3 are the same or different;

$L^1$, $L^2$ and $L^3$ are each independently an arylene group having 6 to 60 ring carbon atoms, and $L^1$, $L^2$ and $L^3$ are the same or different;

$R^1$ and $R^2$ are each independently selected from the group consisting of: a hydrogen atom, a deuterium atom, an alkyl group having 1 to 12 carbon atoms, and an aryl group having 6 to 30 ring carbon atoms, and $R^1$ and $R^2$ are the same or different;

G is selected from the group consisting of: a hydrogen atom, a deuterium atom, —N($Z^3$)($Z^4$) group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms; and $Z^1$ and $Z^2$ are each independently selected from the group consisting of: an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms, or $Z^1$ and $Z^2$ are joined together to form a heteroaryl ring;

$Z^3$ and $Z^4$ are each independently selected from the group consisting of: an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, and a heteroaryl group having 3 to 60 ring carbon atoms, or $Z^3$ and $Z^4$ are joined together to form a heteroaryl ring;

wherein the group of

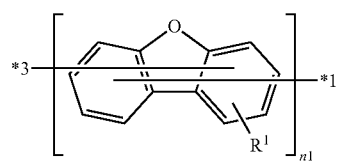

in Formula (I') is represented by

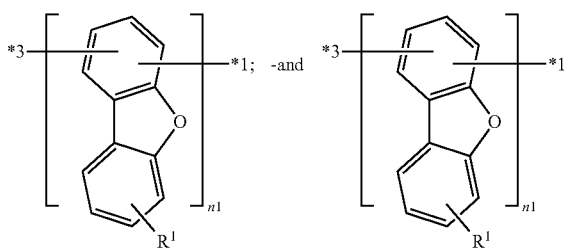

is represented by any one of the following formulae:

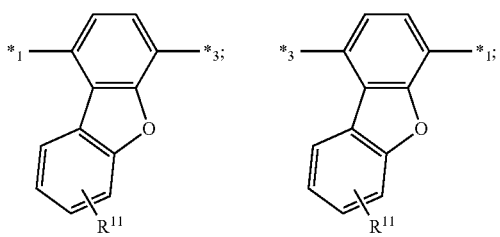

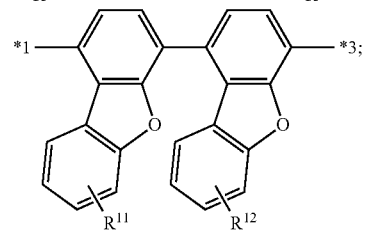

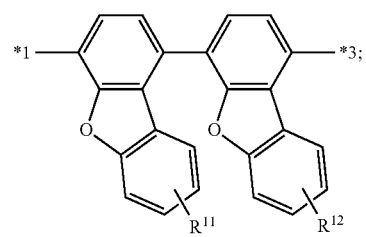

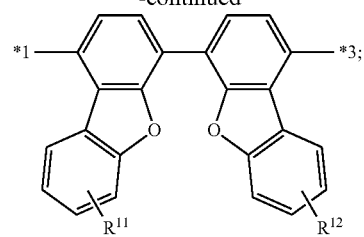
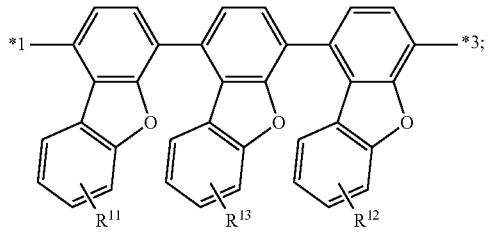
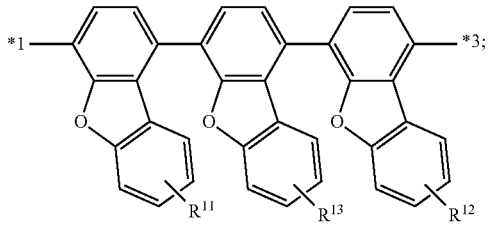
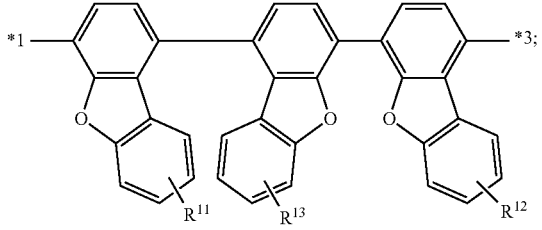
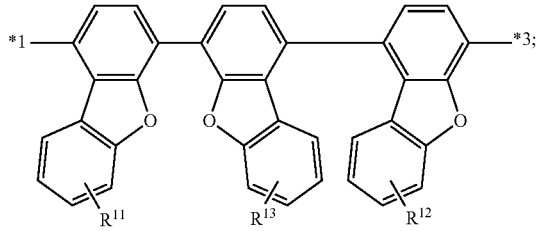
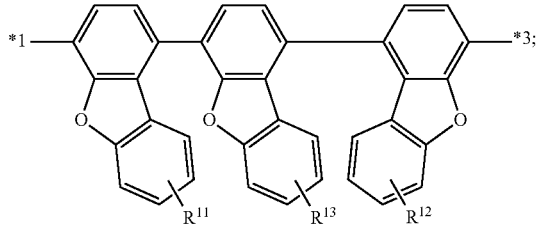
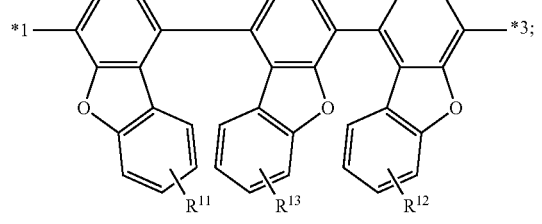
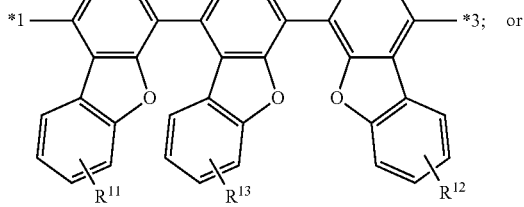
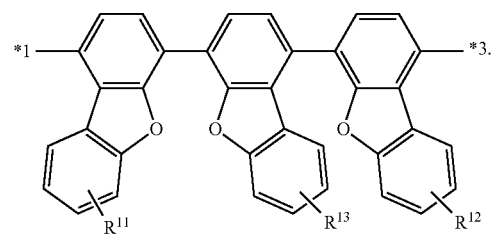
wherein $R^{11}$ to $R^{13}$ are each independently selected from the group consisting of: a hydrogen atom, a deuterium atom, an alkyl group having 1 to 12 carbon atoms, and an aryl group having 6 to 30 ring carbon atoms, and $R^{11}$ to $R^{13}$ are the same or different;
wherein the group of
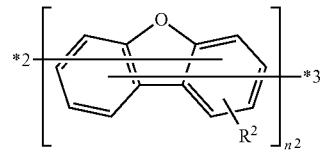
in Formula (I') is represented by
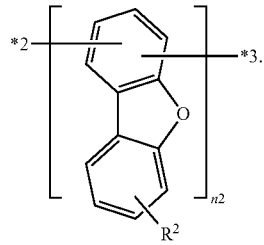
2. The compound as claimed in claim 1, wherein the group of
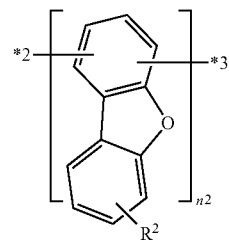

is represented by any one of the following formulae:
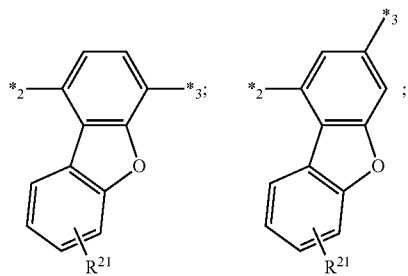
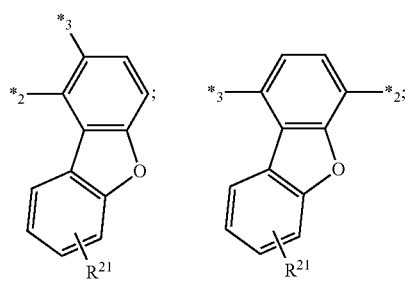
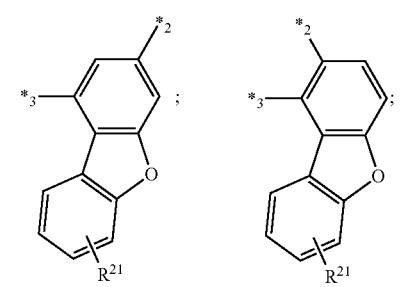
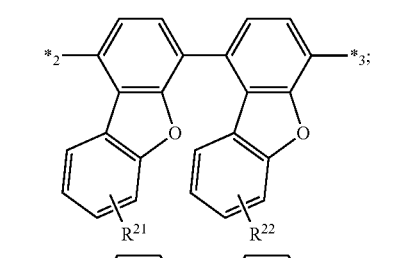
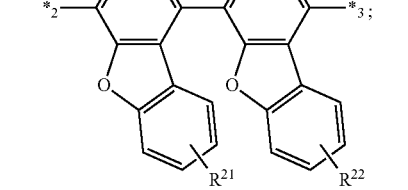
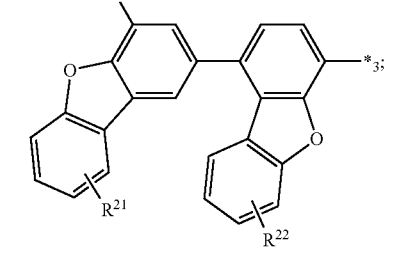
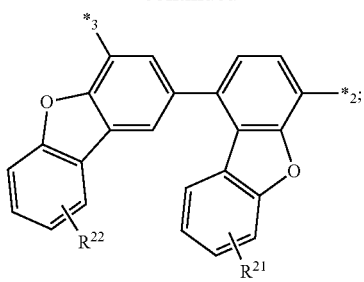
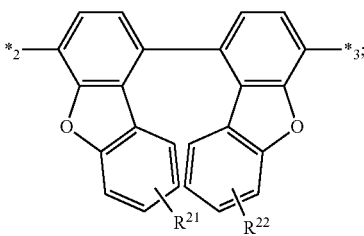
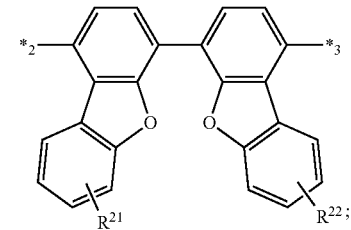
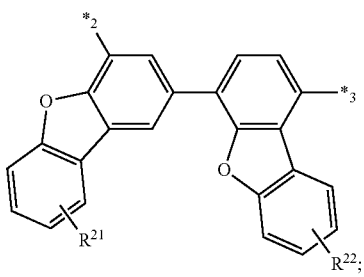
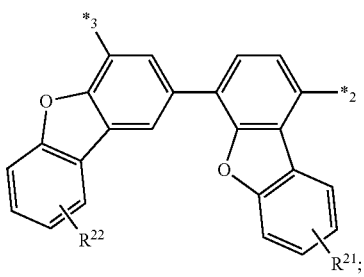
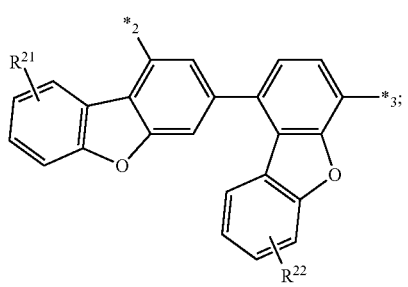

-continued

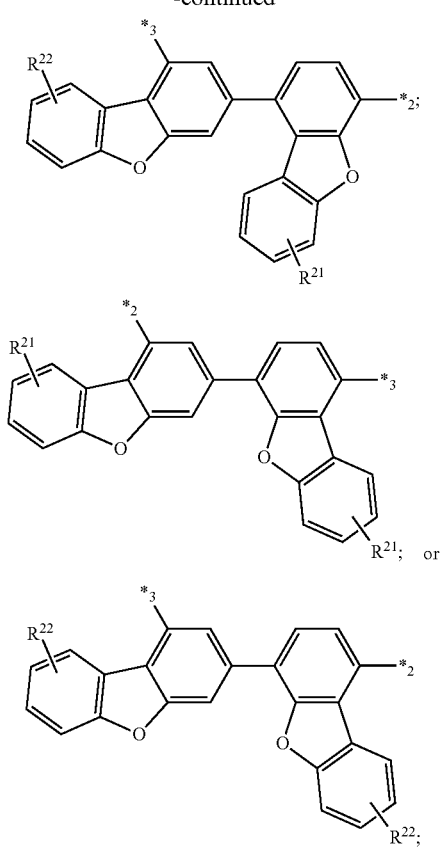

wherein R²¹ and R²² are each independently selected from the group consisting of: a hydrogen atom, a deuterium atom, an alkyl group having 1 to 12 carbon atoms, and an aryl group having 6 to 30 ring carbon atoms, and R²¹ and R²² are the same or different.

3. The compound as claimed in claim 1, wherein the heteroaryl group having 3 to 60 ring carbon atoms represented by G in Formula (I') is represented by any one of the following formulae:

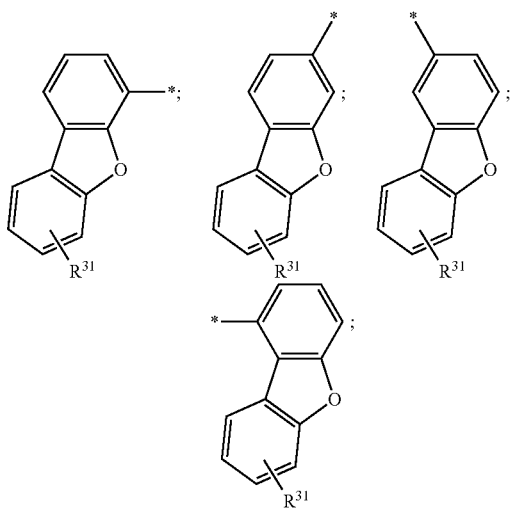

wherein R³¹ is selected from the group consisting of: a hydrogen atom, a deuterium atom, an alkyl group having 1 to 12 carbon atoms, and an aryl group having 6 to 30 ring carbon atoms.

4. The compound as claimed in claim 1, wherein $Z^1$ to $Z^2$ are each independently the aryl group having 6 to 60 ring carbon atoms.

5. The compound as claimed in claim 1, wherein the aryl groups having 6 to 60 ring carbon atoms represented by G and $Z^1$ to $Z^4$ are each independently selected from the group consisting of: a phenyl group, a biphenylyl group, a terphenylyl group, a quaterphenylyl group, a quinquephenylyl group, a naphthyl group, an acenaphthelenyl group, an anthryl group, a benzanthryl group, an aceanthryl group, a phenanthryl group, a benzophenanthryl group, a phenalenyl group, a fluorenyl group, a benzofluorenyl group, a dibenzofluorenyl group, a picenyl group, a pentacenyl group, a pyrenyl group, a benzopyrenyl group, a chrysenyl group, a benzochrysenyl group, a fluoranthenyl group, a benzofluoranthenyl group, a tetracenyl group, a perylenyl group, a coronyl group, a dibenzanthryl group, a naphthylphenyl group, an indacenyl group, a triphenylenyl group, a benzotriphenylenyl group, and any isomeric group thereof.

6. The compound as claimed in claim 1, wherein the aryl groups having 6 to 60 ring carbon atoms represented by G and $Z^1$ to $Z^4$ in Formula (I') are each independently selected from the group consisting of:

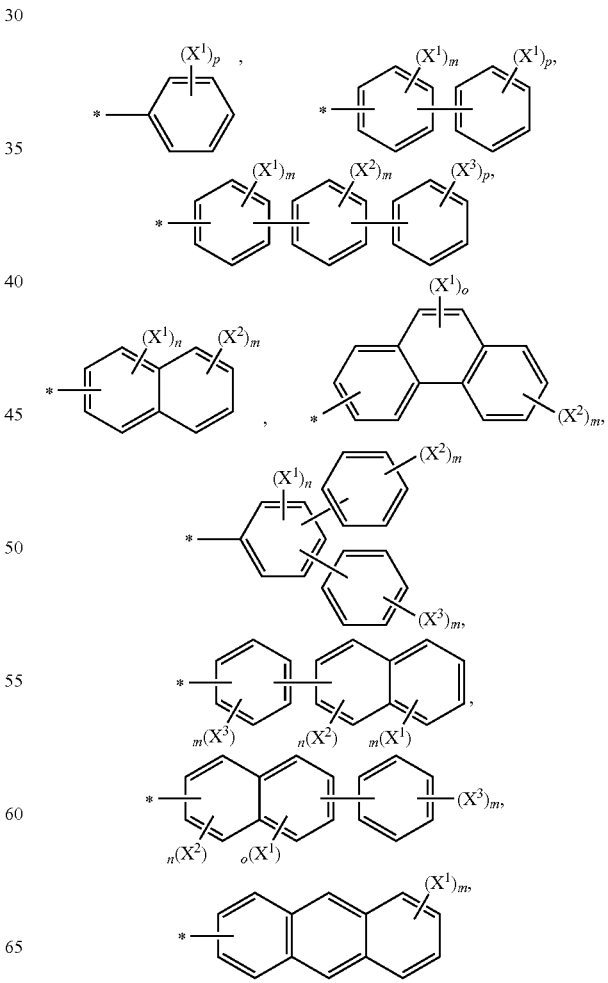

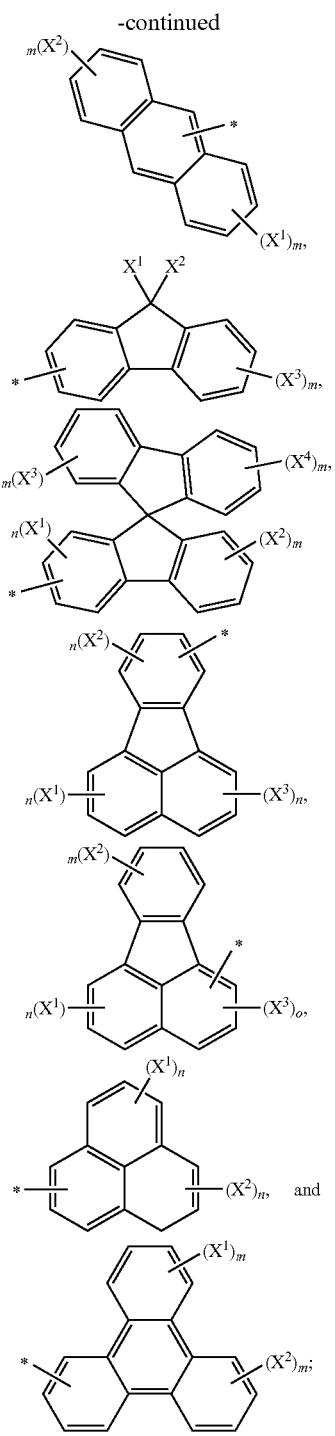

wherein m is an integer from 1 to 4, n is an integer from 1 to 3, o is an integer 1 or 2, and p is an integer from 1 to 5;

$X^1$ to $X^4$ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

7. The compound as claimed in claim 1, wherein the arylene groups having 6 to 60 ring carbon atoms represented by $L^1$, $L^2$ and $L^3$ in Formula (I') are each independently selected from the group consisting of:

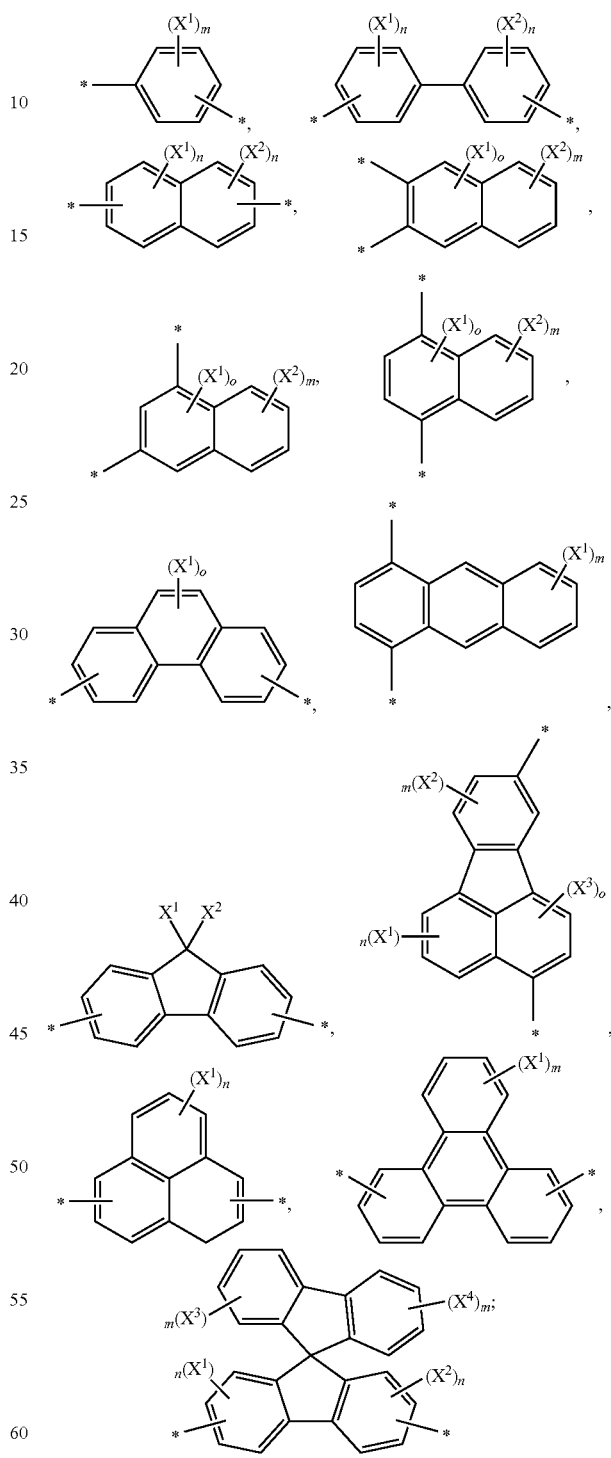

wherein m is an integer from 1 to 4, n is an integer from 1 to 3, and o is an integer 1 or 2;

$X^1$ to $X^4$ are each independently selected from the group consisting of: a hydrogen atom, a deuterium atom, a halo group, a cyano group, a nitro group, an alkyl group having 1 to 12 carbon atoms, an alkenyl group having 2 to 12 carbon atoms, an alkynyl group having 2 to 12 carbon atoms, an alkoxy group having 1 to 12 carbon atoms, an aryl group having 6 to 30 ring carbon atoms, a heteroaryl group having 3 to 30 ring carbon atoms, and an aryloxy group having 6 to 30 ring carbon atoms.

8. The compound as claimed in claim 1, wherein the —N($Z^1$)($Z^2$) group in Formula (I') is selected from the group consisting of:

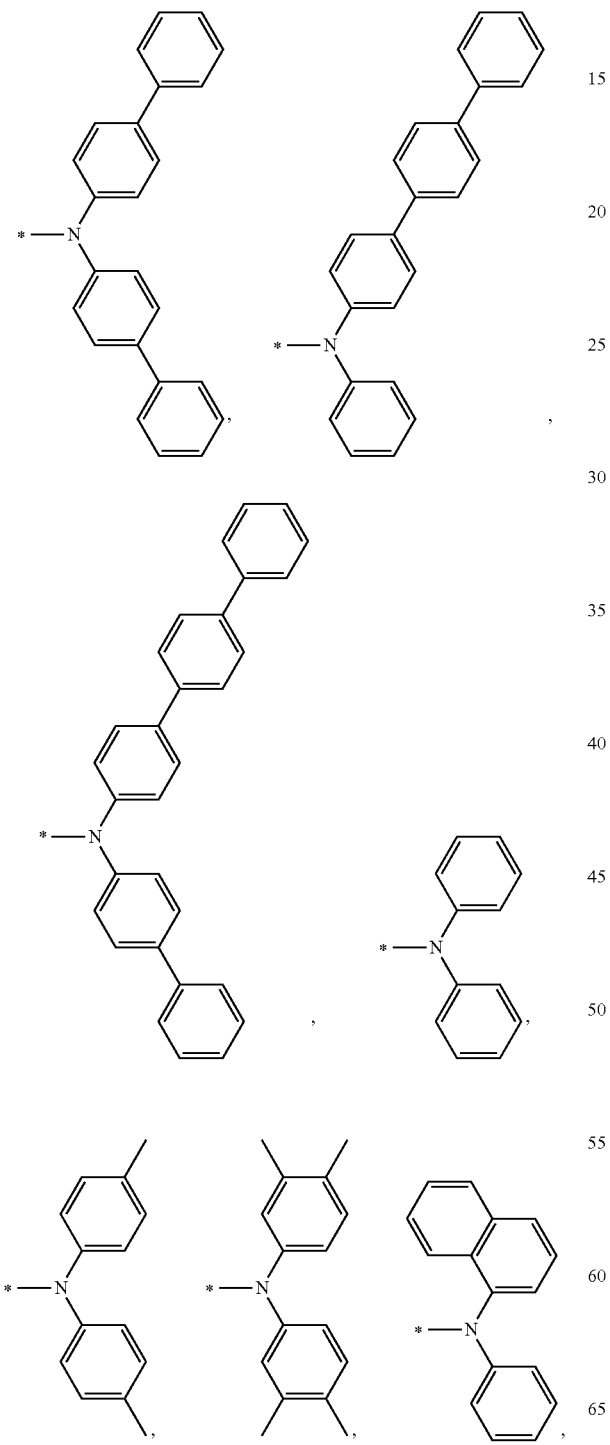

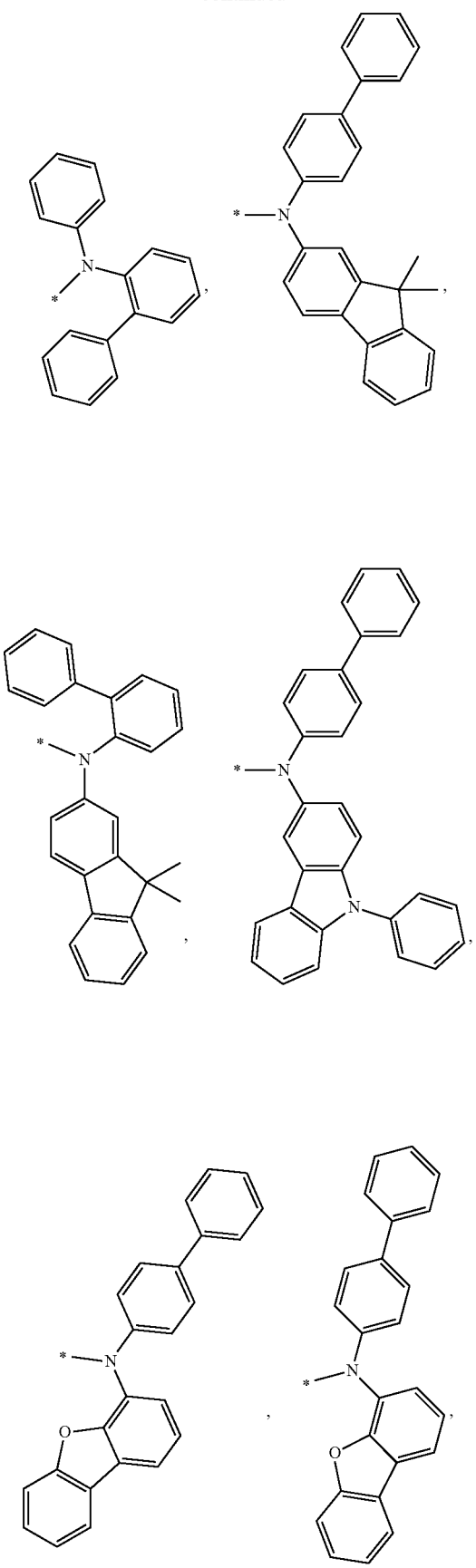

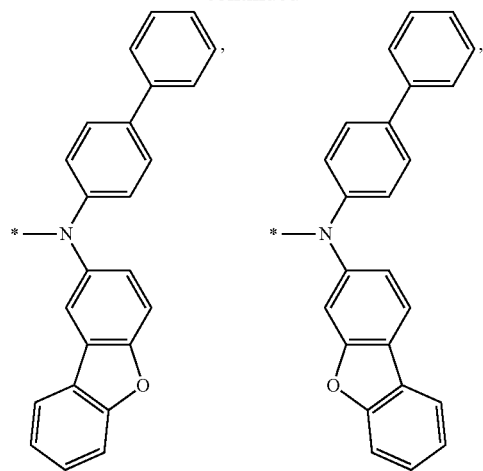
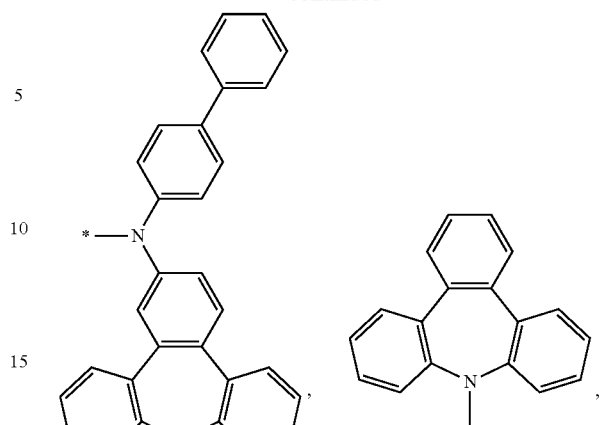
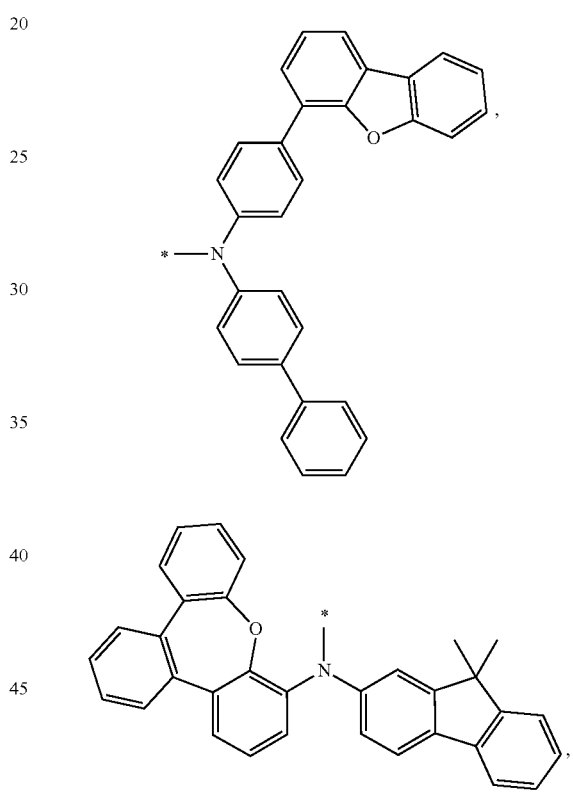
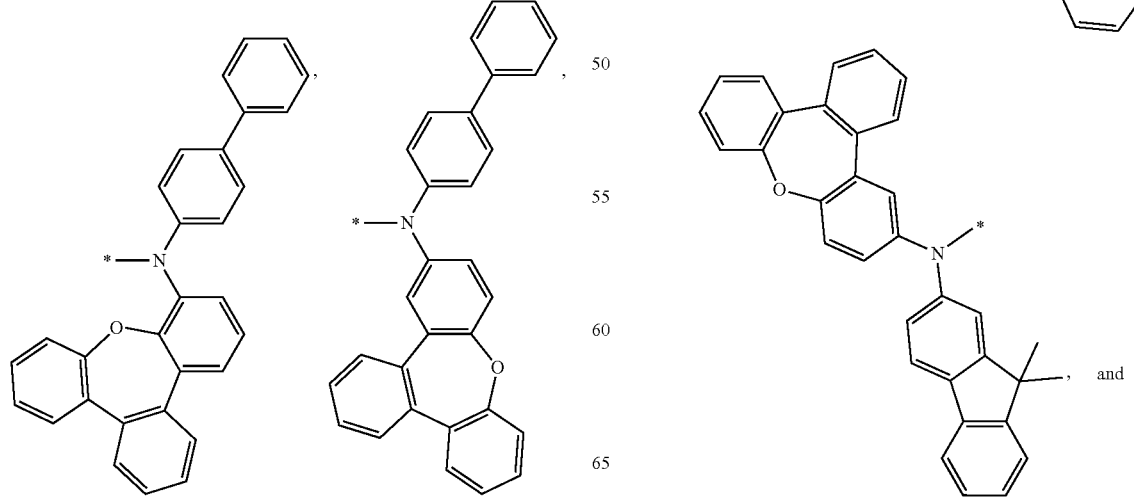

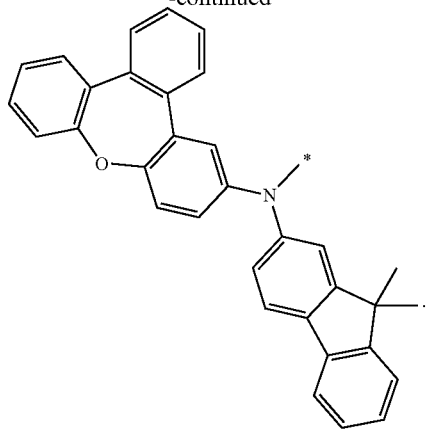

9. The compound as claimed in claim 1, wherein $Z^1$ and $Z^2$ are joined together to form a heteroaryl ring.

10. The compound as claimed in claim 1, wherein G is —N($Z^3$)($Z^4$) group, and $Z^3$ and $Z^4$ are joined together to form a heteroaryl ring.

11. The compound as claimed in claim 1, wherein the compound is represented by the following Formula (I″):

Formula (I″)

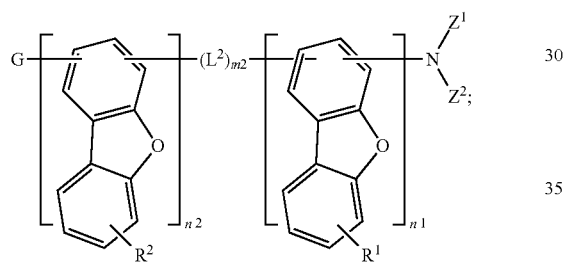

G is selected from the group consisting of: the hydrogen atom, the deuterium atom, the alkyl group having 1 to 40 carbon atoms, the alkenyl group having 2 to 40 carbon atoms, the alkynyl group having 2 to 40 carbon atoms, and the aryl group having 6 to 60 ring carbon atoms.

12. The compound as claimed in claim 1, wherein the compound is selected from the group consisting of:

Compound 1

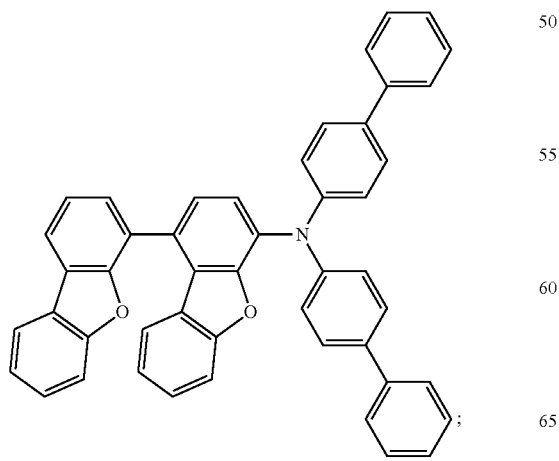

Compound 2

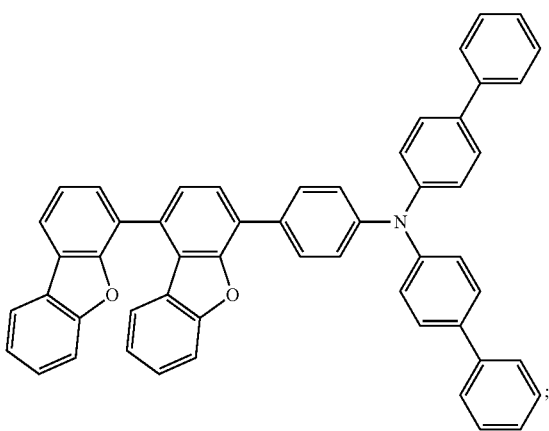

Compound 3

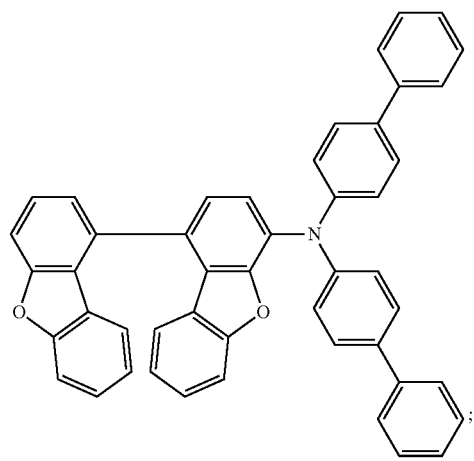

Compound 4

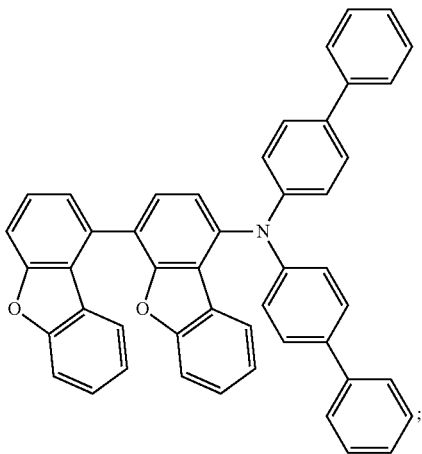

Compound 5

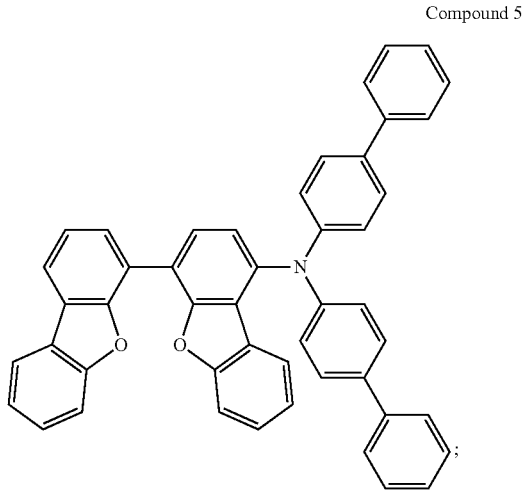

Compound 6

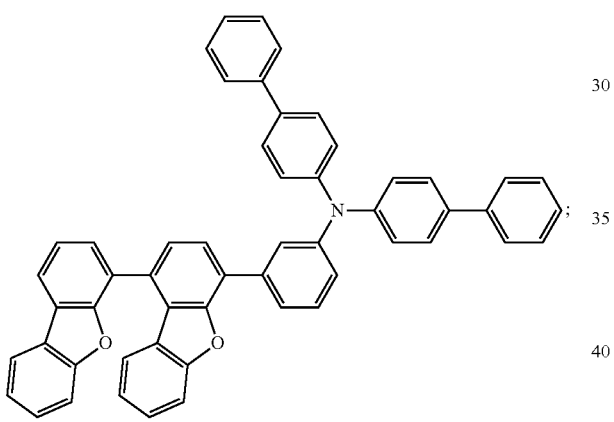

Compound 7

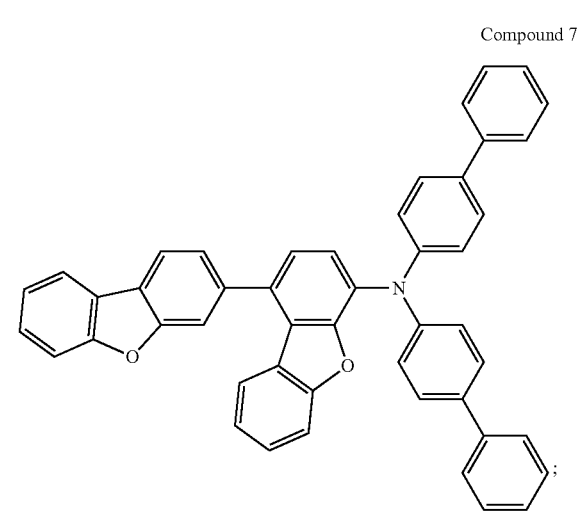

Compound 8

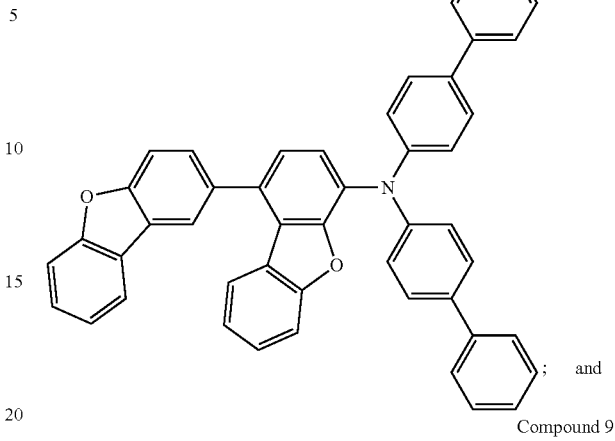

; and

Compound 9

13. An organic electronic device, comprising a first electrode, a second electrode, and an organic layer disposed between the first electrode and the second electrode, wherein the organic layer comprises the compound as claimed in claim 1.

14. The organic electronic device as claimed in claim 13, wherein the organic electronic device is an organic light emitting device.

15. The organic electronic device as claimed in claim 14, wherein the organic light emitting device comprises:
   a hole injection layer formed on the first electrode;
   a hole transport layer formed on the hole injection layer, wherein the hole transport layer comprises the compound as claimed in claim 1;
   an emission layer formed on the hole transport layer;
   an electron transport layer formed on the emission layer; and
   an electron injection layer formed between the electron transport layer and the second electrode.

16. The organic electronic device as claimed in claim 14, wherein the organic light emitting device comprises:
   a hole injection layer formed on the first electrode, wherein the hole injection layer comprises the compound as claimed in claim 1;

a hole transport layer formed on the hole injection layer;
an emission layer formed on the hole transport layer;
an electron transport layer formed on the emission layer; and
an electron injection layer formed between the electron transport layer and the second electrode.

\* \* \* \* \*